(12) United States Patent
Felden

(10) Patent No.: US 7,115,366 B1
(45) Date of Patent: Oct. 3, 2006

(54) EUBACTERIAL TMRNA SEQUENCES AND USES THEREOF

(75) Inventor: Brice Felden, Le Lou du Lac (FR)

(73) Assignee: University of Utah Research Foundation, Salt Lake City, UT (US)

(*) Notice: Subject to any disclaimer, the term of this patent is extended or adjusted under 35 U.S.C. 154(b) by 0 days.

(21) Appl. No.: 09/958,206

(22) PCT Filed: Apr. 6, 2000

(86) PCT No.: PCT/US00/08988

§ 371 (c)(1),
(2), (4) Date: Feb. 20, 2002

(87) PCT Pub. No.: WO00/59918

PCT Pub. Date: Oct. 12, 2000

Related U.S. Application Data

(60) Provisional application No. 60/128,058, filed on Apr. 7, 1999.

(51) Int. Cl.
*C12Q 1/68* (2006.01)
*C07H 21/04* (2006.01)
*C07H 21/00* (2006.01)

(52) U.S. Cl. .................. 435/6; 536/23.1; 536/23.7
(58) Field of Classification Search .............. 435/6, 435/325, 375; 514/44; 536/23.1, 23.7
See application file for complete search history.

(56) References Cited

OTHER PUBLICATIONS

Williams et al. The tmRNA Website. Nucleic Acid Research. 1998, vol. 26, No. 1, pp. 163-165. http:www.wi.mit.edu/bartel/tmRNA/home.*
B. Felden et al., "Eubacterial tmRNAs: everywhere except the alpha-Proteobacteria?" Biochimica et Biophysica Acta 1446:145-148, 1999.
N. Nameki et al., "Three of four pseudoknots in tmRNA are interchangeable and are substitutable with single-stranded RNAs," FEBS Lett 470(3):345-349, Mar. 31, 2000.
N.Nameki et al., "Functional and structural analysis of a pseudoknot upstream of the tag-encoded sequence in *E. coli* tmRNA," J. Mol. Biol 286(3):733-744, Feb. 26, 1999.
W. Schönhuber et al., "Utilization of tmRNA squences for bacterial identification," MBC Microbiology 2001, 1:20 (online, 8 pages).
K.P. Williams et al., "Phylogenetic analysis of tmRNA secondary structure," RNA 2:1306-1310, 1996.
C. Zwieb et al., "Survey and Summary, Comparative sequence analysis of tmRNA," Nucleic Acids Research 27(10):2063-2071, 1999.

* cited by examiner

*Primary Examiner*—Janet L. Epps-Ford
(74) *Attorney, Agent, or Firm*—Rothwell Figg Ernst & Manbeck

(57) ABSTRACT

The present invention is directed to eubacterial tmDNA sequences and the corresponding tmRNA sequences. The present invention is further directed to alignments of eubacterial tmDNA sequences and the use of the sequences and sequence alignments for the development of antibacterial drugs. The present invention is also directed to the use of the sequences for the development of diagnostic assays.

6 Claims, 24 Drawing Sheets

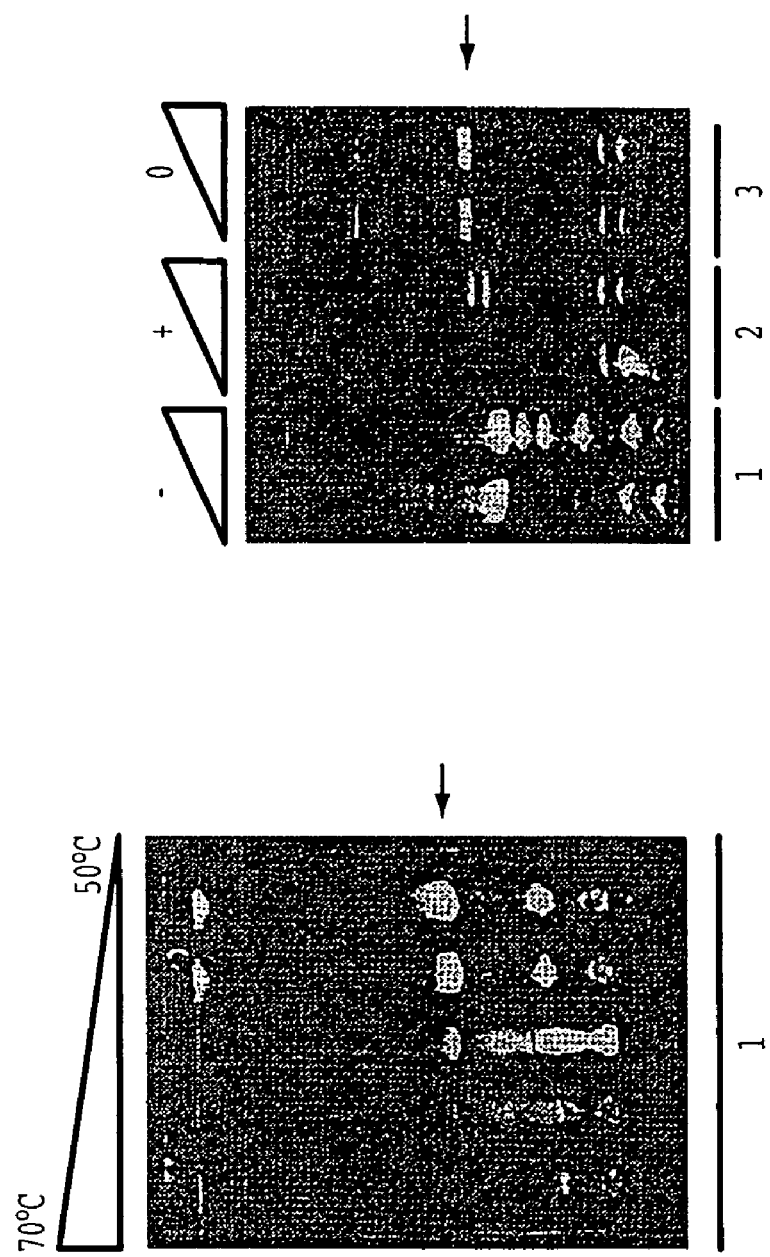

```
                                 ┌─CODING SEQUENCE                                                H4
                                 │                                                          ┌────────────┐
Tab.saccha  AUAAAC│gcaaacgauaau-------------uuagcuuacgcugcuUAA│UUA-CAAGCAGC---
C.acetobut  ******│************-------------*******************│***********---
C.stercora  AUAAAC│gcaaacaacgauaacuac--------gcuuuagcugcugcgUAA│GUAACACGCAGCC--
C.perfrige  AUAAAC│gcagaagauaau-------------uuugcauuagcagcuUAA│UUUAGCGCUGCU---
C.lentocel  GUAAAC│gcugaagauaau-------------uuagcaaucgcugccUAA│UUA-AGGC-GC----
Hlb.mobili  UUAAUU│gccgaagauaac-------------uacgcuuuagcugcuUUA│UUGCAGUCUAA----
Hsp.gestii  UUAAUU│gccgaagauaac-------------uacgcuuuagcugcuUAA│UUGCAGUCUAA----
Bb.brevis   UUAACU│ggcaacaaacaa-------------cuuucucucgcugcuUAA│UAACCAGUGAG----
B.subtilis  AUAACU│ggcaaaacuaacaguuuuaaccaaaacguagcauuagcugcCUAA│UAAGCGCAGCGA---
B.badius    AUAACU│ggcaaaaaagau-------------uuagcuuuagcugccUAA│UAUAGGUUCAGCU--
B.megateri  AUAACU│ggcaaaucuaacaauaac--------uucgcuuuagcugcaUAA│UAGUAGCUUAGC---
B.thermole  AUAACU│ggcaaacaaaac-------------uacgcuuuagcugccUAA│UUGCUGCAGCUA---
Eco.fecium  AUAACU│gcuaaaaacgaaaacaacucu-----uacgcuuuagcugccUAA│AAA-CAGUUAGCGUA
Eco.faecal  AUAACU│gcuaaaaacgaaaacaauucu-----uucgcuuuagcugccUAA│AAACCAGUCUAGCGAA
Stc.pyogen  AUAACU│gcaaaaaauacaaacucu--------uacgcuuuagcugccUAA│AAACCAGUCUAGCGU-
Stc.pneumo  AUAACU│gcaaaaaauaacacuucu--------uacgcucuagcugccUAA│AAACCAGUCAGGCGU-
Stc.gordon  AUAACU│gcaaaaaauaauacuucu--------uacgcuuuagcugccUAA│AAACCAGUCGGGCGU-
Stc.mutans  AUAACU│gcaaaaaauacaaauucu--------uacgcaguagcugccUAA│AAACCAGCCUGUGU-
Stp.epider  AUAACU│gacaaaucaaacaauaau--------uucgcaguagcugcgUAA│UAGCCACUGC-----
Stp.aureus  AUAACU│ggcaaaucaaacaauaau--------uucgcaguagcugccUAA│UCGCA-CU-CUGC--
L.acidophi  AUAACU│gcaaauaacaaaaauucu--------uacgcauuagcugcuUAA│UUUAGCGCAUGCGU- Tab.saccha  CGUUCAA-CCUU-UGAU-UCCCAC--AUCA-AAGGAUUGGGCGUCG--AUUUAGUGGGG
C.acetobut  *********-*********--*AAUCUGGCGUCG----AGAGCGGGG
C.stercora  CGUCGG-C-CCCGGGGUUCCUGC---GCCUCGGGAUACCGGCGUCA---UCAAGGCAGG
C.perfrige  CAUCCUU--CCU-CAAUUGCCCACG-GUUG-AGAGUAAGGGUGUCAUUUAAAAGUGGGG
C.lentocel  AGUCCU---CCU-AGGUCUUCCGCA-GCCU-AGAUC-AGGGCUUCG---ACUCGCGGAU
Hlb.mobili  CCUCUU-C-UCC-UC-UGUGCUCUCGGUGA-GGAUGUAAGGGGUCA-UUUAAGAGAGCU
Hsp.gestii  CCUCUU-C-UCC-UC-UGUGCUCUCGGUGA-GGAUGUAAGGGGUCA-UUUAAGAGAGCU
Bb.brevis   GCUCUC-CCACU-GCAUCGGCCCGU-GUGC-CGUGGAUAGGGCUCAACUUUUAACGGGCU
B.subtilis  GCUCUUC--CUG-ACAU-UGCCUAU-GUGU-CUGU-GAAGAGCACA-UCCAAGUAGGCU
B.badius    GCUCCU--CCCG-CUAU-CGUCCAU-GUAGUCGGGUAAGGGGUCCAAACUUAGUGGACU
B.megateri  GUUCCU--CCCU-CCAU-CGCCCAU-GUGGUAGGGUAAGGGACUCACUUUAAGUGGGCU
B.thermole  GCUCCUC--CCG-CCAU-CGCCCGC-GUGG-CGUUCGAGGGGCUCAUAUGGAGCGGGCU
Eco.fecium  GAUCCU--CUCG-GCAU-CGCCCAU-GUGCUCGAGUAAGGGUCUCAAAUUUAGUGGGAU
Eco.faecal  GAUCCU--CCCG-GCAU-CGCCCAU-GUGCUCGGGUCAGGGUCCUAAUCGAAGUGGGAU
Stc.pyogen  GACUUCU--ACA-AGAU-UGCUUGU-GUCC-UGUU-AGAAGUC-UCAAAAUAGCAAGCU
Stc.pneumo  GACCC--GAUUU-GGAU-UGCUCGU-GUUC-AAUGA-CAGGUCUUAUUAUUAGCGAGAU
Stc.gordon  GACCC--GAUUC-GGAU-UGCUUGU-GUCU-GAUGA-CAGGUCUUAUUAUUAGCAAGCU
Stc.mutans  GAUCAAU--AAC-AAAU-UGCUUGU-GUUU-GUUG-AUUGGUCUUAUUGUUAACAAGCU
Stp.epider  AUCGCC-UAACA-GCAU-CUCCUAC-GUGC-UGUUAACGCGAUUCAACCCUAGUAGGAU
Stp.aureus  AUCGCC-UAACA-GCAU-UUCCUAU-GUGC-UGUUAACGCGAUUCAACCUUAAUAGGAU
L.acidophi  UGCUCU-UUGUC-GGUU-UACUCGU-GGCU-GACAC-UGAGUAUCA-ACUUAGCGAGUU
                                └────────────────────────────────────┘
                                              PK2
```

FIG. 3B

```
                   H1              H5              H2                    PK1
          (5')═══        ══════════        ══════            ════════════════
Aqf.aeolic  GGGGGCGGAAAGGA-UUCGACGGGGACAGGCGG-UCCCGAGGAGCAGGCCGGG--UGGCU------CCCGU-AA-----CAGCC
Tt.maritim  GGGGGCGA-ACGGU-UUCGACGGGGAUGGAGU--CCCCUGGGAAGCGAGCCGAGGUCCCCACCU---CCUCGU-AAAAAAGGUGGG
Tt.neapoli  GGGGGCGGAAAGGA-UUCGACGGGGAUGGAGU--CCCCUGGGAAGCGAGCCGAGGUCCCCACCU---CCUCGU-AAAAAAGGUGGG
T.thermoph  GGGGGUGAAACGGU-CUCGACGGGGGUCGCCGA-GGGCGUGGCUGCGCGCCGAGG--UGCGGGUGG-CCUCGU-AAA-AACCCGCA
D.radiodur  GGGGGUGACCCGGU-UUCGACAGGGGAACUGA--AGGUGAUGUUGCGUGUCGAGG--UGCCGUUGG-CCUCGU-AAACAAACGGCA
D.proteoly  GGGGGCGAAAGGA-UUCGACGGGGAACGGA--AAGCGCUGCUGCGUGCCGAGG--AGCCGUUGG-CCUCGU-AAACAAACGGCA
Tmc.roseum  *************-*****CAGGGCCGUAGGU-GCGAGGAU-UGCAGGUCGAGG-UCGCCCACGA-ACUCGU-AAAAAG-GGGCA
Ctb.proteo  GGGGGCGAAAGGA-UUCGACGGGGAGUCGGA--GCCUUGAGCUGCAGGCAGGGU-UGGCUGCCAC-ACCUUA-AAAAGGGUAGCA
Her.aurant  GGGGGCGAAAGGA-UUCGACGGGGAGGGCCA--AUCGUAAGUGGCAAGCCGAGA---CGCUGAG--CCUCGUUAAAUCGCAACG
Tdb.commun  GGGGGCGAAAGGA-UUCGACGGGGAUAGGUA--GGAUAAACAGCAGGCCGUG-UCGCACCCAA-CCACGUUAAAUAGGGUGCA
Ver.spinos  GGGNNNNAUUUGGAAUUCGCCGAAUGCUAGA---AGUGGAGGCUGCAUGCCGCGGAUGAUUCGUUGGCCGCUUUACCAAUUCGGAU
Dcg.thermo  GGGGGCGAAAGGA-UUCGACGGGGAGUACAAGGAUCAAAAGCUGCAAGCCGAGG--UGCCGUUA--CCUCGU-AAAACAACGGCA
                                         CODING SEQUENCE┐
Aqf.aeolic  GCU-----AAAACA┌gcucccgaagcugaa---------cucgcucucgcugccUAA┐UUAAACGGCAGCG
Tt.maritim  ACAAAGA-AUAAGU│gccaacgaaccu-----------guugcuguugccgccUAA│U-AGAUAAGCGGC
Tt.neapoli  AACACGA-AUAAGU│gccaacgaaccu-----------guugcuguugccgccUAA│U-AGAUAGGCGGC
T.thermoph  ACGGC---AUAACU│gccaacaccaac-----------uacgcucucgcgccUAA│---UGACCGCGA
D.radiodur  AAGCCAU-UUAACU│ggcaaccagaac-----------uacgcucucgcugcuUAA│------GUGAGA
D.proteoly  AAGCCA--UUAACU│ggcgaaaauaac-----------uacgcucucgcugcuUAA│------GUGAGA
Tmc.roseum  GCCAA---GUAACU│ggcgagcgcgaa-----------cucgcucuggcugcgUAA│-UUCACGCAGCCA
Ctb.proteo  AGGCAAAAUAAAU│gccgaaccagaa-----------uuugcacuagcugcuUAA│--UGUAAGCAGCC
Her.aurant  CCA-----UUAACU│ggcaaaaacacuuuccgcgcuccuguagcgcuugcugcCUAA│UUAAGGCAACACG
Tdb.commun  AAAAC---ACAACU│gccaacgaauacgcc--------uacgcuuggcagccUAA│--GCGUGCUGCCA
Ver.spinos  CAAACAA-CUAAAU│gcggacucuaacgag--------cuugcccucgccgcuUAA│---UUGACGGUGA
Dcg.thermo  AAAA----AGAAGU│gccaacacaaau-----------uuagcauuagcugcuUAA│---UUUUAGCAGCU
                                                                         ══╗  HH4
Aqf.aeolic  CGUCC--C-CGGU-AGGUUUGCGGGUGGCCU-ACCG-G--AGGGCGUCAGAGACACCCGCU  │
Tt.maritim  CGUCCU-C--UCC-GAAGUUGGCUGGGCUUC-GGAA-G--AGGGCGUGAGAGAUCCAGCCU  │
Tt.neapoli  CGUCCU-C--UCC-GGAGUUGGCUGGGCUCC-GGAA-G--AGGGCGUGAGGGAUCCAGCCU  │
T.thermoph  CCUCGC-C-CGGU-AGCCCUGCCGGG-GGCUCACCG-GAAGCGGGGACACA-AACCCGGCU  │
D.radiodur  UGACGACC-GUGC-AGCCCGGCCUUU-GGCG-UCGC-GG-AAGUCACUAAAAAAGAAGGCU  │
D.proteoly  CAGUGACC-ACGU-AGCCCCGCCUUU-GGCG-ACGU-GU-GAACUGAGACAAAAGAAGGCU  ╠═PK2
Tmc.roseum  CGUCUG-C-CCGG-ACCCUUCCCUGGUGGGU-UCGGAG--CGGGCGCCGCAAGACCGGGGU  │
Ctb.proteo  -GCUC--U-CCAA-ACUGAGGCUGCAUAAGU-UUGG-A--AGAGCGUCAACCCAUGCAGCG  │
Her.aurant  -UCUCU-A-CUAG-CCUCAGCCCGAU--GGG-CUUG-U--AGCGGCGACACUUAGUCGGGU  │
Tdb.commun  -CGCAC-C-UUUA-GACCUUGCCUGUGGGUC-UAAA-G--GUGUG-UGACC-UAACAGGCU  │
Ver.spinos  -CGUUC-C-UCCA-GUGA-AGUCUGU-GAAU-UGGA-G--GAGCG-ACUAC-UUACAGGCU  │
Dcg.thermo  ACGCUC-U-UCUA-ACCCGGGCUGGCAGGGU-UAGA-A--GGGUGUCAUAAUGAGCCAGCU ═╝
                                                                    PK2
```

FIG. 4A

```
Aqf.aeolic  CG-GGCUACUCGGU--CGCACGGG-GCUGAGUAGCUGACACCUAACCCGUGCU  ⎫
Tt.maritim  A--CCGAUUCAG--UUCGCCUUCCGGCCUGAAUCGGGAAAACUCAGGAAGGCU  ⎪
Tt.neapoli  A--CCGAUCUGGGCUCCGCCUUCCGGCCCGGAUCGGGAAGGUUCAGGAAGGCU  ⎪
T.thermoph  A--GCCCGGGGC--CACGCCCUCU--AACCCCGGGCGAAGCUUGAAGGGGCU  ⎪
D.radiodur  A--GCCC-AGGC--GAUUCUCCAU--AGCCGACGGCGAAACU-UUAUGGAGCU  ⎪
D.proteoly  A--GCUU-AGGU--GAGGUUCCAU--AGCCAAAAGUGAAACC-AAAUGGAAAU  ⎪
Tmc.roseum  GCCCCUGGCCCA--AGCGCCGGUG---CGGGCCAGGUCAAGCGUGAUCCGGCU  ⎬ PK3
Ctb.proteo  GC-UCUUAAGCAG--UGGCACCAG--CUGUUUAAGGGUGAAAAGAGUGGUGCU  ⎪
Her.aurant  CGCUCCCCUAGUU--AUGUCUGUG--GGCUAGGGG--CUAAGAUUAACAGGCU  ⎪
Tdb.commun  UU-GGGAGGCUUAA-UCGGUGGGG-UUAAGCCUCCCGAGAUUACAUCCCACCU  ⎪
Ver.spinos  G--GCCAAAAGAGC-GGGCGACCG-GC-CCCAAGGCGAGAUCUACAGGCCGCU  ⎪
Dcg.thermo  GCCCCUUCCG-----ACUCCCCUA-----AGGAAGGGAAAGA-UGUAGGGGAU  ⎭
                             ════                ═══════

Aqf.aeolic  A--CCCUC-GGGGAGCUUGCCCGUGGGCGACCC-GAGGG--GAAAUCC-UGAACACGGGC  ⎫
Tt.maritim  G-UGGGAGAGGACACCCUGCCCGUGGGAGGUCC-CUCCC--GAGAGCG-AAAACACGGGC  ⎪
Tt.neapoli  G-UGGGAAGCGACACCCUGCCCGUGGGGGGUC-CUUCCC--GAGACAC-GAAACACGGGC  ⎪
T.thermoph  C-GCUCCUGGCC--GCCCGUCCGCGGGCCAAGCCAGGAG--GACACGC-GAAACGCGGAC  ⎪
D.radiodur  A-CGGCCUGCGAGAACCUGCCCACUGGUGAGCGCCGGCCC-GACAAUC-AAACAGUGGGA  ⎪
D.proteoly  A-AGGCGGACGGCAGCCUGUUUGCUGGCAGCCCAGGCCC--GACAAUU-UAAGAGCAGAC  ⎪
Tmc.roseum  C-GGCUGACCGGGAUCCUGUCGGUGGGAGCCUGG-CAGC--GACAGUA--GAACACCGAC  ⎬ PK4
Ctb.proteo  G--GGCAGUGCGGUU-GGGCU-UCCUGGGCUGCACUGUC--GACACUU-CACAGGAGGGC  ⎪
Her.aurant  G-GUCGUGGC-CCGCUUUGUCUAUCGGGUGGUGCACCGAU-AAGAUUU-AAUCAAUAGAC  ⎪
Tdb.commun  G--GUAGGGUUGCUUGGUGCCUGUGACAAGCA-CCCUAC--GAGAUUU--UCCCACAGGC  ⎪
Ver.spinos  G--GAUGGACGGCAUCCUGGCAGUAGGAGGCUGGACAUC--GACAUCA--AAUNAUUGCC  ⎪
Dcg.thermo  AGGUGCUUACAGAAUCCUGCGGGAGGGAGUCUGUAAGUGCCGAAAAGUUAAAACUCCCGC  ⎭
                                  ════                      ════

Aqf.aeolic  UAAGCC-UGUAGAGCCUCGGAUGUGGCCGCCGUCCUCGGACGCGGGUUCGAUUCCCGCCGCCUCCACCA
Tt.maritim  UGCGCU-CGGAGAAGCCCAGGGG---CCUCCAUCUUCGACGGGGGUUCGAAUCCCCCGCCUCCACCA
Tt.neapoli  UGCGCU-CGGAGAAGCCCAGGGG---CCUCCAUCUUCGACGGGGGUUCGAUUCCCGCCGCCUCCA***
T.thermoph  UACGCG-CGUAGAGGCcacgccc---cggcgaccuucggacggggguucgauuccccaccuccacca
D.radiodur  UACACA-CGUAGACGCA-CGCUG---GACGGACCUUUGGACGGCGGUUCGACUCCGCCCACCUCCACCA
D.proteoly  UACGCA-CGUAGAUGCA-CGCUG---GAUGGACCUUUGGACGGCGGUUCGAUUCCCGCCGCCU-CACCA
Tmc.roseum  UAAGCC-UGUAGCAUAUCCUCGG---CUGAACGCUCUGGACGGGGGUUCAACUCCCGCCAGCUCCACCA
Ctb.proteo  UAAGCC-UGUAGACGCGAAAGGU---GGCGGCUCGUCGGACGCGGGUUCGAUUCCCGCCGCCUCCACCA
Her.aurant  UACGCU-UGUAGAUGCUUGCGGU----UUAACUUUUUGGACGCGGGUUCGAUUCCCGCCGCCUCCACCA
Tdb.commun  UAAGCC-UGUAGCGGUUUAAUCU---GAACUAUCUCCGGACGCGGGUUCGAUUCCCGCCGCCUCCACCA
Ver.spinos  UGAGCA-UGGAGACGCUUUCAUA-----AAGGNGUUCGGACAGGG************************
Dcg.thermo  UAAGCU-UGUAGAGGCUUUUGAU---UCUUGCUCUCUGGACGCGGGUUCGAUUCCCGCCGCCUCCACCA (3')
                 ═══              ═════            ═══════       ════
                  H2               H5              H6           H1
                                                  ────────────────
                                                  +RNA-LIKE DOMAIN H1-H6
```

FIG. 4B

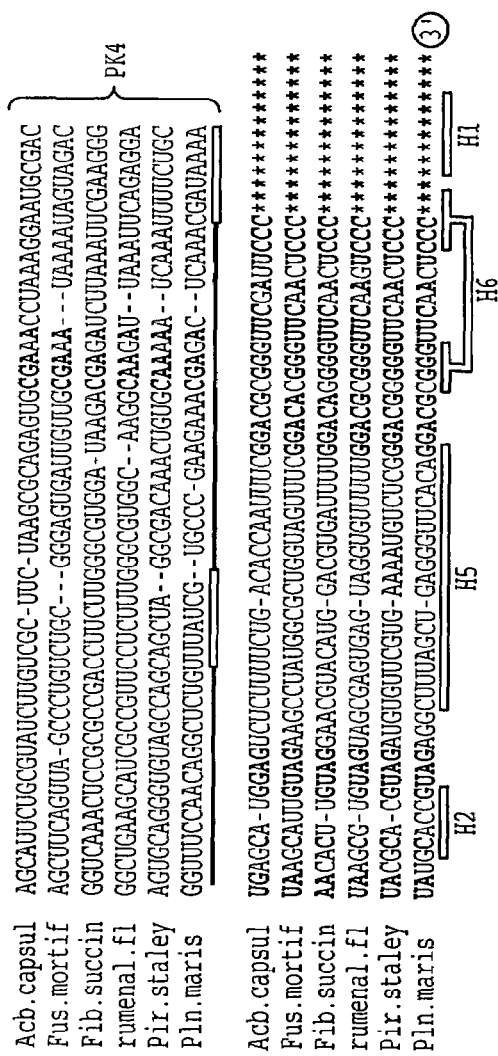

FIG. 7D

| | | | |
|---|---|---|---|
| Alc.faecal | GCAGUGUUAU-UUACAAAGAAU | -C-GAAUCGGUCUGCGCCACGAAGUCCGGUUCUAAAA-CUUAGUGGAU | |
| Alc.eutrop | GCGAGGUCAU-UUACGUCAGAU | -A-AGCUCCGGAAGGGUCACGAAGCCGGGGACGAAAA-CCUAGUGACU | |
| Ral.picket | GCGAGGUCAU-UUACGUCAGAU | -A-AGCUUUAGGUGAGUCACGGGCCUAGAGACGAAAA-CUUAGUGAAU | |
| Nis.gonorr | GCAACGUCAUCUUACAUUGACU | -G-GUUUCCAGCCGGGUUACUUGGCAGGAAAUAAGACUUAAGGUAACU | |
| Nis.meninS | GCAACGUCAUCUUACAUUGACU | -G-GUUUCCUGCCGGGUUAUUUGGCAGGAAAUGAGAUUUAAGGUAACU | |
| Chb.violac | GUAGUGUCACUCUACAUCUGCU | -A-GUGCUGUUCCGGGUUACUUGGUUCAGUGCGAAAUAAUAGGUAACU | PK3 |
| Nms.cryoto | GCAGAGUCAU-UAG-CAAGGAU | -C-GCGUUCUGUAGGGUCACUUUACAGAACGUUAAACAAUAGGUGACU | |
| Mtb.glycog | GCAGCGUCAU-UAAGAGAGGAU | -C-GUGCGAUAUUGGGUUACUUAAAUAUCGUAUUAAAUCCAAGGUAACU | |
| Ps.testost | GCAAGGGAAU-UUUCAUUAGCU | -G-GCUGGAUACCGGGCUUCUUGGUAUUUGGCGAGAUUUUAGGAAGCU | |
| Vx.paradox | GCAAGGAUAA-CUACAUGGGCU | -G-GCUCCGAUCCGGGUACCUUGGGUCGGGGCGAGAAAAUAGGGUACU | |
| Hph.paller | GCAAGGUAAU-UUACAUCGGCU | -G-GUUCUGCGUCGGGCACCUUGGCGCAGGAUGAGAUUCAAGGAUGCU | |
| Brd.pertus | GCAGCGACAU-UCACAAGGAAU | -C-GGCCACCGCUGGGGUCACA-CGGCGUUGGUUUAAA-UUACGUGAAU | |
| | PK2 | | |

| | |
|---|---|
| Alc.faecal | CGCCAAGG-AAAGGCCUGUCA-AUUGGCAUAGUCCAAGGUUAAAACUUAAAAUUAAU-UGAC |
| Alc.eutrop | CGCCGUCG-UAGAGCGUGUUC-GUCCGCGAUG-CGCCGGUUAAAU---CAAA-UGACAGAAC |
| Ral.picket | CGCCGUCG-UAGAGCGUGUUC-GUCCGCGAUG-CGGCGGUUAAAU---CAAA-UGACAGAAC |
| Nis.gonorr | GGUUUCCA-AAAGGCCUGUUG-GUCGGCAUGA-UGGAAAUAAGAUUUUCAAAUAGACACAAC |
| Nis.meninS | GGUUUCCA-AAAGGCCUGUUG-GUCGGCAUGA-UGGAAAUAAGAUUUUCAAAUAGACACAAC |
| Chb.violac | CGCCAAAGUCCA-GCCUGUCC-GUCGGCGUGG-CAGAGGUUAAAUC--CAAA-UGACACGAC |
| Nms.cryoto | CGCCUGCC-AUCAGCCCGCCA-GCUGGCGGUU-GUCAGGUUAAAU---UAAA-GAGCAUGGC |
| Mtb.glycog | CGCCUGCU-GUUUGCUUGCUC-GUUGGUGAGC-AUCAGGUUAAAU---CAAA-CAACACAGC |
| Ps.testost | GGCUACCCAAGCAGCGUGUGC-CUGCGGGGUUUGGGUGGCGAGAUU--UAAA-ACAGAGCAC |
| Vx.paradox | GGCGUCCGGUUUAGCGUGUGA-CUGCGCGACUCCGGAAGCGAGACU--CAAA-ACAGAUCAC |
| Hph.paller | GGCUUCCCGUUUAGCGUGCCA-CUGCGCGACUCGGGCGGCGAGACC--CAAA-UCAGACGGC |
| Brd.pertus | CGCCCUGG-UCCGGCCCGUCG-AUCGGCUAAGUCCAGGGUUAAAUC--CAAAUAGAU-CGAC |

PK4

| | |
|---|---|
| Alc.faecal | UACACAUGUAGAACUGUCUGUGGACGGCUUGCGGACGGGGGUUCGAUUCCC********** |
| Alc.eutrop | UAAGUAUGUAGAACUCUCUGUGGAGGGCUUACGGACGCGGGUUCGAUUCCCGCCGGCUCCACCA |
| Ral.picket | UAAGUAUGUAGAACUCUCUGUGGAGGGCUUGCGGACGCGGGUUCGAUUCCC********** |
| Nis.gonorr | UAAGUAUGUAGAACGCUUUGUAGAGGACUUUCGGACGGGGGUUCGAUUCCCCCCGCCUCCACCA |
| Nis.meninS | UAAGUAUGUAGAACGCUUUGUAGAGGACUUUCGGACGGGGGUUCGAUUCCCCCCGCCUCCACCA |
| Chb.violac | UAAGUAUGUAGAACUCACUGUAGAGGACUUUCGGACGCGGGUUCAACUCCC********** |
| Nms.cryoto | UAAGUAUGUAGAACUGUCUGUAGAGGACUUGCGGACGCGGGUUCAACUCCC********** |
| Mtb.glycog | UAAGUAUGUAGAACUGUCUGUGGAGGGCUUGCGGACGCGGGGUUCGAUUCCC********** |
| Ps.testost | UAAACAUGUAGAUCUGUCCGGCGAAGGCUUACGGACGCGGGUUCAAUUCCCGCCGGCUCCA*** |
| Vx.paradox | UAAACAUGUAGAACUGCGCGAUGAAGGCUUGCGGACGGGGGUUCAACUCCC********** |
| Hph.paller | UACACAUGUAGAACUGCUCGAAAAAGGCUUGCGGACGGGGGUUCAACUCUCC********** |
| Brd.pertus | UAAGCAUGUAGAACUGGUUGCGGAGGGCUUGCGGACGGGGGUUCAAUUCCCCCCGGCUCCACCA (3') |
| | H2    H5    H6  H1 |

FIG. 9B

```
                          H1                          H5                H2
             ⑤          ├─────┤          ├────────────────────────┤
Leg.pneumo   ****************************CGUGGGUUGCAAAACCGGAAGUGCAUGC
Chr.vinosu   ****************************CGUGGGUCGCGAAACCUAAGGUGCAUGC
Dcb.nodosu   ****************************************CUCGAGGUGCAUGU
Ps.aerugin   GGGGCCGAUU-AGGAUUCGACGCCGGUAACAAAACUUGAGGGGCAUGC
Ps.fluores   ****************************CGCCGGUUGCGAACCUUUAGGUGCAUGC
Mar.hydroc   ****************************CGCCGGUGACGAACCCUUGGGUGCAUGC
Shw.putref   GGGGGCGAUUCUGGAUUCGACAGGAUUCACGAAACCCUGGGAGCAUGC
Psm.halopl   ****************************CGGAAUUCAAGAAGCCCGAGGUGCAUGU
Ae.salmoni   ****************************CAAGAUUCACGAAACCCAAGGUGCAUGC
S.typhimur   GGGGCUGAUUCUGGAUUCGACGGGAUUUGCGAAACCCAAGGUGCAUGC
E.coli       GGGGCUGAUUCUGGAUUCGACGGGAUUUGCGAAACCCAAGGUGCAUGC
Yer.pestis   GGGGCUGAUUCUGGAUUCGACGGGAUUCGCGAAACCCAAGGUGCAUGC
V.cholerae   GGGGCUGAUUCAGGAUUCGACGGGAAUUUUGCAGUCUGAGGUGCAUGC
H.influenz   GGGGCUGAUUCUGGAUUCGACGGGAUUAGCGAAGCCCAAGGUGCACGU
H.actinomy   GGGGCUGAUUCUGGAUUCGACGGGAUUAGCGAAGCCCGAAGUGCACGU
                                         PK1
                        ├────────────────────────────────┤
Leg.pneumo   CGAG-AAGGAGAUC-UCUCGUAAAUA-AGA-CUCAAUUA-AAU
Chr.vinosu   CGAG-GUGCGGUUGACCUCGUAAAAC--CCUCCGCAAA--CUU
Dcb.nodosu   CGAG-AAUGAGAGAAUCUCGUUAAAU--ACUUUCAAAA--CUU
Ps.aerugin   CGAGCUGGUAGCAGAACUCGUAAAUUCGCUGCUGCAAA--CUU
Ps.fluores   CGAGUUGGUAACAGAACUCGUAAAUCCACUGUUGCAACUUUCU
Mar.hydroc   CGAGAUGGCAGCGAAUCUCGUAAAUCCAAAGCUGCAAC--GUA
Shw.putref   CGAG-GGGCGGUUGGCCUCGUAAA----AAGCCGCAAA--GUU
Psm.halopl   CGAG-GUGCGGUUUGCCUCGUAAAA---AAGCCGCAAUU-UAA
Ae.salmoni   CGAG-GUGCGGUAGGCCUCGUUAAC---AAACCGCAAA--AAA
S.typhimur   CGAG-GGGCGGUUGGCCUCGUAAA----AAGCCGCAAA--AAA
E.coli       CGAG-GGGCGGUUGGCCUCGUAAA----AAGCCGCAAA---AA
Yer.pestis   CGAG-GUGCGGUG-GCCUCGUAAA----AAACCGCAAA-AAAA
V.cholerae   CGAG-GUGCGGUAGGCCUCGUUAAC---AAACCGCAAA--AAA
H.influenz   CGAG-GUGCGGUAGGCCUCGUAAAU---AAACCGCAAA--AAA
H.actinomy   CGAG-GUGCGGUAGGCCUCGUAAAU---AAACCGCAAA--AAA
                                                         CODING SEQUENCE
                                                              ↓
Leg.pneumo   A-UAAAU│gcaaacgaugaaaacuuugcuggugggaagcuaucgcugccUAA│-----UAAGCACUUU
Chr.vinosu   A-UAGUU│gccaacgacgacaacuac-----------gcucucgcugcuUAA│-----UCCCAGCGGG
Dcb.nodosu   A-UAGUU│gcaaacgacgacaacuac-----------gcuuuagcggcuUAA│-----UUCCCGCUUU
Ps.aerugin   A-UAGUU│gccaacgacgacaacuac-----------gcucuagcugcuUAA│------UGCGGCUAG
Ps.fluores   A-UAGUU│gccaaugacgaaaccuac---ggggaauacgcucucgcugcgUAA│-------GCAGCCUU
Mar.hydroc   A-UAGUC│gcaaacgacgaaaacuac-----------gcacuggcggcgUAA│---GCCGUU-CCAGU
Shw.putref   A-UAGUU│gcaaacgacgauaacuac-----------gcucuagccgcuUAA│------UGCCGCUAG
Psm.halopl   AGUAAUC│gcaaacgacgauaacuac-----------ucucuagcagcuUAG│------GCUGGCUAG
Ae.salmoni   A-UAGUC│gcaaacgacgaaaacuac-----------gcacuagcagcuUAA│UAACCUGCAUAGAGC
S.typhimur   A-UAGUC│gcaaacgacgaaaccuac-----------gcuuuagcagcuUAA│UAACCUGCUUAGAGC
E.coli       A-UAGUC│gcaaacgacgaaaacuac-----------gcuuuagcagcuUAA│UAACCUGCUUAGAGC
Yer.pestis   A-UAGUU│gcaaacgacgaaaacuac-----------gcacuagcagcuUAA│UAACCUGCUUAGAGC
V.cholerae   A-UAGUC│gcaaacgacgaaaacuac-----------gcacuagcagcuUAA│UACCCUGCUCAGAGC
H.influenz   A-UACUC│gcaaacgacgaacaauac-----------gcuuuagcagcuUAA│UAACCUGCAUUUAGC
H.actinomy   A-UAGUC│gcaaacgacgaacaauac-----------gcuuuagcagcuUAA│UAACCUGCCUUUAGC
                                                                  H4
```

FIG. 10A

```
Leg.pneumo    AGUUAAACCAUCACUGUGUACUGGCCAAUAAACCCAGUAUC
Chr.vinosu
Dcb.nodosu
Ps.aerugin
Ps.fluores    AGCCCUUCCCUCCUGGUACCUUCGGGUCCAG
Mar.hydroc
Shw.putref
Psm.halopl
Ae.salmoni
S.typhimur
E.coli
Yer.pestis
V.cholerae
H.influenz
H.actinomy Leg.pneumo    CCGUUCG-ACCGAGCCC--GCUUAUC-GGUAUCGAA------UCAACGGUCAU-AAGAGAU-AAGCU
Chr.vinosu    CCUCUGA-CCGUCACUU--GCCUGUGGGCGGCGAUU------CCAGGGGUAAC-CUCACAC-AGGAU
Dcb.nodosu    CGCUUAC-CUAGAUUU---GUCUGUGGGUUUACC--------GUAAGCGACAU--UAACAC-AGAAU
Ps.aerugin    CAGUCGC-UAGGGGAU---GCCUGUAAACCCGAAA-------CGACUGUCAG-AUAGAAC-AGGAU
Ps.fluores    CAAUCAU-CAGGGGAU---GUCUGUAAACCCAAAG-------UGAUUGUCAU-AUAGAAC-AGAAU
Mar.hydroc    CGUCCUG-GCUGAGGC---GCCUAUAACUCAGUAGCAACAUCCCAGGACGUCAU-CGCUUAU-AGGCU
Shw.putref    CCAUCUA-CCACACGCUUUGCACAUGGGCAGUGGAUU------UGAUGGUCAU-CUCACAUCGUGCU
Psm.halopl    CGCUCCU-UCCAUGUAU--UCUUGUG-GACUGGAUUUU-----GGAGUGUCACCCUAACAC-CUGAU
Ae.salmoni    CCUUCUA-CCCUAGCUU--GCCUGUGUCCUAGGGAAUC-----GGAAGGUCAU-CCUUCAC-AGGAU
S.typhimur    CCUCUCU-CCCUAGCCUCCGCUCUUAGGACGGGGAUCA----AGAGAGGUCAAACCCAAAA-GAGAU
E.coli        CCUCUCU-CCCUAGCCUCCGCUCUUAGGACGGGGAUCA----AGAGAGGUCAAACCCAAAA-GAGAU
Yer.pestis    CCUCUCU-CCCUAGCCUCCGCUCUUAGGACGGGGAUCA----AGAGAGGUCAAACCUAAAA-GAGCU
V.cholerae    CCUUCCU-CCCUAGCUUCCGCUUGUAAGACGGGGAAAUC---AGGAAGGUCAAACCAAAUC-AAGCU
H.influenz    CUUCGCG-CUCCAGCUUCCGCUCGUAAGACGGGGAUAA----CGCGGAGUCAAACCAAAAC-GAGAU
H.actinomy    CUUCGCU-CCCCAGCUUCCGCUCGUAAGACGGGGAUAA----AGCGGAGUCAAACCAAAAC-GAGAU
                                                          PK2
```

FIG. 10B

```
                        PK3
             ┌────────────────────────────────────────────────┐
Leg.pneumo   -AGCG-UCCU-AAUCU--AUCCC-GGGUU-AUGG-CGCGAAA-CU-CA--GGGAAU
Chr.vinosu   -CGUG-GUGA-CGGGA--GUCCG-GACCU-GAUC-CACUAAAACC-UA-ACGGAAU
Dcb.nodosu   -CGCU-GGUU-AACG--CGUCCGC-UGUU-AAUC-GGUUAAA-UU-AA-GCGGAAU
Ps.aerugin   -CGCC-GCCA-AGUU--CGCUGUA-GACG-UAAC-GGCUAAAACU-CA-UACAGCU
Ps.fluores   -CGCC-GUGC-AGUA--CGUUGUG-GACG-AAGC-GGCUAAAACU-UA-CACAACU
Mar.hydroc   GCUCC-GUUC-ACCAG-AGCUCA-CUGGU-GUUC-GGCUAAG-AU-UA-AAGAGCU
Shw.putref   -AGCGAGGGA-ACCC--UGUCUGG-GGGU-GAAC-CGCGAAACAG-UA-CCGGACU
Psm.halopl   -CGCGACGGA-AACCC-UGGCCG-GGGUU-GAAG-CGUUAAAACU-AA-GCGCCCU
Ae.salmoni   -CGUG-UGGA-AGUCC-UGCUCG-GGGCG-GAAG-CAUUAAAACC-AA-UCGAGCU
S.typhimur   -CGCG-CGGA-UGCCC-UGCCUG-GGGUU-GAAG-CGUUAAAACG-AA-UCAGGCU
E.coli       -CGCG-UGGA-AGCCC-UGCCUG-GGGUU-GAAG-CGUUAAAACUUAA-UCAGGCU
Yer.pestis   -CGUG-UGGA-AACCU-UGCCUG-GGGUG-GAAG-CAUUAAAACU-AA-UCAGGAU
V.cholerae   -GGCG-UGGA-UUCCCCCACCUGA-GGGAUGAAG-CGCGAGAUCU-AAUUCAGGUU
H.influenz   -CGUG-UGGA-AGCCACCGUUUGA-GGAUCGAAG-CACUAAAUUG-AA-UCAAACU
H.actinomy   -CGUG-UGGA-AGCCACCGUUUGA-GGAUCGAAG-CAUUAAAUUA-AA-UCAAAGU ┌────────────────────────────────────────────────────┐
Leg.pneumo   CGCUGUGUAU-CAUCCUGCCC-GUCGGAGGAGCCACAGUUAAAUUCAAAAGACAAGGC--  ┐
Chr.vinosu   CGCCGACUGAUCGCCCUGCCC-UUCGGGCGGCAGAAGGCUAAAAACAAUAGAGUGGGC--  │
Dcb.nodosu   CGCUUGUAAA-AUGCCUGAGC-GUUGGCUGUUUAUGAGUUAAACCUAAAUUAACUGCUC--  │
Ps.aerugin   CGCUCCAAGC--ACCCUGCCA-CUCGGGCGGCGCGGAGUUAA-CUCAGUAGAGCUGGC--   │
Ps.fluores   CGCCCAAAGC--ACCCUGCCC-GUCGGGUCGCUGAGGGUUAA-CUUAAUAGACACGGC--   │
Mar.hydroc   CGCCUCUUGC--ACCCUGACC-UUCGGGUCGCUUGAGGUUAA-AUCAAUAGAA-GGACAC   │
Shw.putref   CACCGUGUGG-GAUCCUGUCU-UUCGGAGUUCAAACGGUUAA-ACAAUA-GAA-AGAC--   │
Psm.halopl   CGCCUUUAUC-UACCGUGUUU-GUCCGGGAUUUAAAGGUUAA-UUAAAU-GACAAUAC--   ├─PK4
Ae.salmoni   AGUCAAUUCG-UGGCGUGUCU-CUCCGCAGCGGGUUGGCGAA-UGUAAA-GAG-UGAC--   │
S.typhimur   AGUCUGGUAG-UGGCGUGUCC-GUCCGCAGGUGCCAGGCGAA-UGUAAA-GAC-UGAC--   │
E.coli       AGUUUGUUAG-UGGCGUGUCC-GUCCGCAGCUGGCAAGCGAA-UGUAAA-GAC-UGAC--   │
Yer.pestis   AGUUUGUCAG-UAGCGUGUCC-AUCCGCAGCUGGCCGGCGAA-UGUAAU-GAUUGGAC--   │
V.cholerae   AGCCAUUCGU-UAGCGUGUCG-GUUCGCAGGCG-GUGGUGAA-AUUAAA-GAU-CGAC--   │
H.influenz   AGCUUAAGUU-UAGCGUGUCU-GUCCGCA-UGCUUAAGUGAA-AUUAAA-GACGAGAC--   │
H.actinomy   AGCUUAAUUG-UCGCGUGUCC-GUCAGCA-GGAUUAAGUGAA-UUUAAA-GACCGGAC--   ┘

Leg.pneumo   UAUGCAUGUAGAGCUAAAGGCAGAGGACUUGCGGACGCGG*********************
Chr.vinosu   UAAGCAUGUAGGACCGAGGGCAGAGGGCUUGCGGACGCGG*********************
Dcb.nodosu   UAAACAUGUAGUACCAAAAGUUAAGGAUUCGCGGACGGGGGUUCAAAUCCCCCCGCCUCCACCA
Ps.aerugin   UAAGCAUGUAGAACCGAUAGCGGAGAGCUGGCGGACGGGGGUUCAAAUCCCCCCGGCUCCACCA
Ps.fluores   UACGCAUGUAGUACCGACAGCAGAGUACUGGCGGACGGGG*********************
Mar.hydroc   UAAGCAUGUAGACCUCAAGGCCUAGUGCUGGCGGACGCGG*********************
Shw.putref   UAAGCAUGUAGCGCCUUGGAUGUAGGUUUUCUGGACGCGGGUUCAAGUCCCGCCGCCUCCACCA
Psm.halopl   UAAACAUGUAGUACCGACGGUCGAGGCUUUUCGGACGGGG*********************
Ae.salmoni   UAAGCAUGUAGUACCGAGGAUGUAGUAAUUUUGGACGGGG*********************
S.typhimur   UAAGCAUGUAGUACCGAGGAUGUAGGAAUUUCGGACGCGGGUUCAACUCCCGCCAGCUCCACCA
E.coli       UAAGCAUGUAGUACCGAGGAUGUAGGAAUUUCGGACGCGGGUUCAACUCCCGCCAGCUCCACCA
Yer.pestis   UAAGCAUGUAGUGCCGACGGUGUAGUAAUUUCGGACGGGGGUUCAAAUCCCCCCAGCUCCACCA
V.cholerae   UAAGCAUGUAGUACCAAAGAUGAAUGGUUUUCGGACGGGGGUUCAACUCCCCCCAGCUCCACCA
H.influenz   UAAACGUGUAGUACUGAAGGUAGAGUAAUUUCGGACGGGGGUUCAACUCCCCCCAGCUCCACCA
H.actinomy   UAAACGUGUAGUGCUAACGGCAGAGGGAAUUUCGGACGGGGGUUCAACUCCCCCCAGCUCCACCA (3')
             ═════════  ════════════════════  ═══════════════════  ══════
                H2            H5                  H6          H1
```

FIG. 10C

SEQUENCE LISTING

```
<160> NUMBER OF SEQ ID NOS: 175

<210> SEQ ID NO 1
<211> LENGTH: 21
<212> TYPE: DNA
<213> ORGANISM: Artificial
<220> FEATURE:
<223> OTHER INFORMATION: PCR primer

<400> SEQUENCE: 1
ggggctgatt ctggattcga c                                              21

<210> SEQ ID NO 2
<211> LENGTH: 21
<212> TYPE: DNA
<213> ORGANISM: Artificial
<220> FEATURE:
<223> OTHER INFORMATION: PCR primer

<400> SEQUENCE: 2
tggagctggc gggagttgaa c                                              21

<210> SEQ ID NO 3
<211> LENGTH: 21
<212> TYPE: DNA
<213> ORGANISM: Artificial
<220> FEATURE:
<223> OTHER INFORMATION: PCR primer

<400> SEQUENCE: 3
gggggcggaa aggattcgac g                                              21

<210> SEQ ID NO 4
<211> LENGTH: 21
<212> TYPE: DNA
<213> ORGANISM: Artificial
<220> FEATURE:
<223> OTHER INFORMATION: PCR primer

<400> SEQUENCE: 4
tggaggcggc gggaatcgaa c                                              21
```

<210> SEQ ID NO 5
<211> LENGTH: 21
<212> TYPE: DNA
<213> ORGANISM: Artificial
<220> FEATURE:
<223> OTHER INFORMATION: PCR primer

<400> SEQUENCE: 5
ggggatgtca tggttttgac a         21

<210> SEQ ID NO 6
<211> LENGTH: 21
<212> TYPE: DNA
<213> ORGANISM: Artificial
<220> FEATURE:
<223> OTHER INFORMATION: PCR primer

<400> SEQUENCE: 6
tggagatggc gggaatcgaa c         21

<210> SEQ ID NO 7
<211> LENGTH: 21
<212> TYPE: DNA
<213> ORGANISM: Artificial
<220> FEATURE:
<223> OTHER INFORMATION: PCR primer

<400> SEQUENCE: 7
ggggatgaca ggctatcgac a         21

<210> SEQ ID NO 8
<211> LENGTH: 21
<212> TYPE: DNA
<213> ORGANISM: Artificial
<220> FEATURE:
<223> OTHER INFORMATION: PCR primer

<400> SEQUENCE: 8
tggagatggc gggacttgaa c         21

<210> SEQ ID NO 9
<211> LENGTH: 352
<212> TYPE: DNA
<213> ORGANISM: Acidobacterium capsulatum

<400> SEQUENCE: 9
gggggcggaa aggattcgac ggggttgact gcggcaaaga ggcatgccgg ggggtgggca    60
cccgtaatcg ctcgcaaaac aatacttgcc aacaacaatc tggcactcgc agcttaatta   120
aataagttgc cgtcctctga ggcttcgcct gtgggccgag gcaggacgtc atacagcagg   180
ctggttcctt cggctgggtc tgggccgcgg ggatgagatc cacggactag cattctgcgt   240
atcttgtcgc ttctaagcgc agagtgcgaa acctaaagga atgcgactga gcatggagtc   300
tcttttctga caccaatttc ggacgcgggt tcgattcccg ccgcctccac ca            352

<210> SEQ ID NO 10
<211> LENGTH: 353
<212> TYPE: DNA
<213> ORGANISM: Coprothermobacter proteolyticus

<400> SEQUENCE: 10
gggggcggaa aggattcgac ggggagtcgg agccttgagc tgcaggcagg gttggctgcc    60

-continued

```
acaccttaaa aagggtagca aggcaaaaat aaatgccgaa ccagaatttg cactagctgc    120
ttaatgtaag cagccgctct ccaaactgag gctgcataag tttggaagag cgtcaaccca    180
tgcagcggct cttaagcagt ggcaccagct gtttaagggt gaaaagagtg gtgctgggca    240
gtgcggttgg gcttcctggg ctgcactgtc gagacttcac aggagggcta agcctgtaga    300
cgcgaaaggt ggcggctcgt cggacgcggg ttcgattccc gccgcctcca cca           353
```

<210> SEQ ID NO 11
<211> LENGTH: 399
<212> TYPE: DNA
<213> ORGANISM: Bacteroides thetaiotaomicron

<400> SEQUENCE: 11

```
ggggctgatt ctggattcga cagcgggcag aaatggtagg taagcatgca gtgggtcggt     60
aatttccact taaatctcag ttatcaaaac tttatctggc gaaactaatt acgctcttgc    120
tgcttaatcg aatcacagta gattagctta atccaggcac taggtgccag gacgagacat    180
cactcggaag ctgttgctcc gaagcattcc ggttcagtgg tgcagtaaca tcggggatag    240
tcagaagcgg cctcgcgttt tgatgaaac tttagaggat aaggcaggaa ttgatggctt    300
tggttctgct cctgcacgaa aatttaggca agataagca tgtagaaagc ttatgatttc    360
ctcgtttgga cgagggttca actcccgcca gctccacca                            399
```

<210> SEQ ID NO 12
<211> LENGTH: 352
<212> TYPE: DNA
<213> ORGANISM: Dictyoglomus thermophilum

<400> SEQUENCE: 12

```
ggggctgatt ctggattcga cagggagtac aaggatcaaa agctgcaagc cgaggtgccg     60
ttacctcgta aaacaacggc aaaaaagaag tgccaacaca aatttagcat tagctgctta    120
atttagcagc tacgctcttc taacccgggc tggcagggtt agaagggtgt cataatgagc    180
cagctgcccc ttccgactcc cctaaggaag ggaaagatgt aggggatagg tgcttacaga    240
atcctgcggg agggagtctg taagtgccga aaagttaaaa ctcccgctaa gcttgtagag    300
gcttttgatt cttgctctct ggacgcgggt tcaactcccg ccagctccac ca            352
```

<210> SEQ ID NO 13
<211> LENGTH: 313
<212> TYPE: DNA
<213> ORGANISM: Artificial
<220> FEATURE:
<223> OTHER INFORMATION: sequence isolated from rumenal fluid

<400> SEQUENCE: 13

```
acgcccttgt ctcagacgag ggcactcgtt aaaagtctg aaaagaataa ctgcagaacc      60
tgtagctatg gctgcttaat ttaagggcaa cccttggatc cgcctccatc ccgaaggggt    120
ggcatccgag tcgcaaatcg ggataggatg gatcttggca acgaggagta catccgaaat    180
ttgtcgctgc tggctgaagc atcgccgttc ctctttgggc gtggcaaggc aagattaaat    240
tcagaggata agcgtgtagt agcgagtgag taggtgtttt tggacgcggg ttcaagtccc    300
gccatctcca cca                                                        313
```

<210> SEQ ID NO 14
<211> LENGTH: 350
<212> TYPE: DNA
<213> ORGANISM: Artificial

```
<220> FEATURE:
<223> OTHER INFORMATION: sequence isolated from sludge

<400> SEQUENCE: 14
ggggatgtca tggttttgac agggaaccag gaggtgtgag atgcatgccg gagacgctgt      60
ccgctccgtt atcaagcagc aaacaaaact aattgcaaac acaattact ccttagcagc      120 gtaagcagct aacgttcaac ctctccggac cgccggagg ggatttgggc gtcgaaacag      180
cgcggacgct ccggatagga cgcccataat atccggctaa gaccatgggt ctggctctcg      240
cgggtctgat tgtcttccac cgcgcgggcc gcgatcaaag acaactaagc atgtaggttc      300
ttgcatggcc tgttctttgg acgcgggttc gattcccgcc atctccacca               350

<210> SEQ ID NO 15
<211> LENGTH: 359
<212> TYPE: DNA
<213> ORGANISM: Fibrobacter succinogenes

<400> SEQUENCE: 15
ggggctgatt ctggattcga cagggttacc gaagtgttag ttgcaagtcg aggtctcaga      60
cgagggctac tcgttaaaaa gtctgaaaaa aataagtgc tgacgaaaac tacgcactcg      120
ctgcctaatt aacggcaacg ccgggcctca ttccgctccc atcggggtgt acgtccggac      180
gcaatatggg atagggaagt gtcatgcctg ggggcatctc ccgagatttt ctaggctggt      240
caaactccgc gccgaccttc ttgggcgtgg ataagacgag atcttaaatt cgaagggaac      300
acttgtagga acgtacatgg acgtgatttt ggacagggt tcaactcccg ccagctcca       359

<210> SEQ ID NO 16
<211> LENGTH: 350
<212> TYPE: DNA
<213> ORGANISM: Fusobacterium mortiferum

<400> SEQUENCE: 16
ggggctgatt ctggattcga cggggttatg aggttatagg tagcatgcca ggatgaccgc      60
tgtgagaggt caaacacatcg tttagatgga acagaaatt acgctttagc tgcttaatta      120
gtcagctcac ctctggtttc tctcttctgt aggagaatcc aaccgaggtg ttaccaatat      180
acagattacc tttagtgatt tctctaagct caaagggaca tttttagagaa tagcttcagt      240 tagccctgtc tgcgggagtg attgttgcga aataaaatag tagactaagc attgtagaag      300
cctatggcgc tggtagtttc ggacacgggt tcaactcccg ccagctccaa               350

<210> SEQ ID NO 17
<211> LENGTH: 377
<212> TYPE: DNA
<213> ORGANISM: Corynebacterium xerosis

<400> SEQUENCE: 17
ggggctgatt ctggattcga cttcgtacat tgagccaggg gaagcgtgcc ggtgaaggct      60
ggagaccacc gcaagcgtcg cagcaaccaa ttaagcgccg agaactctca gcgcgactac      120
gccctcgctg cctaagcagc gaccgcgtgt ctgtcagacc gggtaggcct ctgatccgga      180
ccctggcatc gtttagtggg gctcgctcgc cgacttggtc gcaagggtcg gcggggacac      240
tcacttgcga ctgggcccgt catccggtca tgttcgactg aaccgagggg ccgagcagag      300
accacgcgcg aactgcgcac ggagaagccc tggcgaggtg acggaggacc cgggttcaac      360
tcccgccagc tccacca                                                    377
```

<210> SEQ ID NO 18
<211> LENGTH: 372
<212> TYPE: DNA
<213> ORGANISM: Micrococcus luteus
<220> FEATURE:
<221> NAME/KEY: misc_feature
<222> LOCATION: (1)..(372)
<223> OTHER INFORMATION: n is an unknown base

<400> SEQUENCE: 18

```
ggggctattc tggattcgac ggtgtgtgtc gcgtcgggag aagcgggccg aggatgcaga      60
gtcatctcgt caaacgctct ctgcaaacca ataagtgccg aatccaagcg cactgacttc     120
gctctcgctg cctgatcagt gatcgagtcc gtcaccccga ggtcgctgtc gcctcggatc     180
gtggcgtcag ctagatagcc actgggcgta accctcgccg ggggtcgtga cgccgacatc     240
aatccggctg ggtccgggtt ggccgcccgt ctgcgggacg gccaggaccg agcaacaccc     300
acagcagact gcgcccggag aagacctggc aacacctcat cggacgcggg ttcaactccc     360
gcantcccac ca                                                         372
```

<210> SEQ ID NO 19
<211> LENGTH: 372
<212> TYPE: DNA
<213> ORGANISM: Mycobacterium smegmatis

<400> SEQUENCE: 19

```
tcatctcggc ttgttcgcgt gaccgggaga tccgagtaga gacatagcga actgcgcacg      60
gagaggggct gattcctgga ttcgacttcg agcatcgaat ccagggaagc gtgccggtgc     120
aggcaagaga ccaccgtaag cgtcgttgca accaattaag cgccgattcc aatcagcgcg     180
actacgccct cgctgcctaa gcgacggctg gtctgtcaga ccgggagtgc cctcggcccg     240
gatcctggca tcagctagag ggacccaccc acgggttcgg tcgcgggacc tgtggggaca     300
tcaaacagcg actgggatcg agcctcgagg acatgccgta ggacccgggt tcaactcccg     360
ccagctccac ca                                                         372
```

<210> SEQ ID NO 20
<211> LENGTH: 355
<212> TYPE: DNA
<213> ORGANISM: Bacillus badius

<400> SEQUENCE: 20

```
gggggtgatt ctggattcga cagggatagt tcgagcttgg gctgcgagcc ggagggccgt      60
cttcgtacca acgcaaacgc ctaaatataa ctggcaaaaa agatttagct ttagctgcct     120
aatataggtt cagctgctcc tcccgctatc gtccatgtag tcgggtaagg ggtccaaact     180
tagtggacta cgccggagtt ctccgcctgg ggacaaagga agagatcaat caggctagct     240
gcccggacgc ccgtcgatag gcaaaaggaa cagtgaaccc caaatatatc gactacgctc     300
gtagacgttc aagtggcgtt atctttggac gtgggttcaa ctcccgccag ctcca         355
```

<210> SEQ ID NO 21
<211> LENGTH: 357
<212> TYPE: DNA
<213> ORGANISM: Bacillus brevis

<400> SEQUENCE: 21

```
gggggcggaa aggattcgac ggggatggta gagcatgaga agcgagccgg ggggttgcgg      60
acctcgtcac caacgcaaac gccattaact ggcaacaaac aactttctct cgctgcttaa     120
```

```
taaccagtga ggctctccca ctgcatcggc ccgtgtgccg tggatagggc tcaactttaa      180
cgggctacgc cggaggcttc cgcctggagc caaaggaaga agaccaatca ggctaggtgc      240
caggtcagcg cgtcactccg cgaatctgtc accgaaactc taaacgagtg actgcgctcg      300
gagatgctca tgtatcgctg ttttcggacg ggggttcgat tcccgccgcc tcaccca        357

<210> SEQ ID NO 22
<211> LENGTH: 354
<212> TYPE: DNA
<213> ORGANISM: Bacillus thermoleovorans

<400> SEQUENCE: 22
gggggcggaa aggattcgac gggggtaggt cgagcttaag cggcgagccg agggggacgt      60
cctcgtaaaa acgtcaccta agataactg gcaaacaaaa ctacgcttta gctgcctaat      120
tgctgcagct agctcctccc gccatcgccc gcgtggcgtt cgaggggctc atatggagcg      180
ggctacgccc aaatccgccg cctgaggatg agggaagaga cgaatcaggc tagccgccgg      240
gaggcctgtc ggtaggcgga acggacggcg aagcgaaata taccgactac gctcgtagat      300
gcttaagtgg cgatgcctct ggacgtgggt tcgattcccg ccgcctcccc acca           354

<210> SEQ ID NO 23
<211> LENGTH: 384
<212> TYPE: DNA
<213> ORGANISM: Clostridium innocuum

<400> SEQUENCE: 23
gggggcggaa aggattcgac ggggatatgt ctggtacaga ctgcagtcga gtggttacgt      60
aataaccaat taaattttaaa cggaaaaact aaattagcta acctctttgg tggaaaccag      120
agaatggctt cgctgcctta ataaccgata taggttcgca gccgcctctg catgcttctt      180
ccttgaccat gtggatgtgc gcgtaagacg caagggataa ggaatctggt ttgcctgaga      240
tcagattcac gaaaattctt caggcacatt catcagcgga tgttcatgac ctgctgatgt      300
cttaatcttc atggactaaa ctgtagaggt ctgtacgtgg ggctgttct ggacaggagt      360 tcgattcccg ccgcctcacc acca                                             384

<210> SEQ ID NO 24
<211> LENGTH: 349
<212> TYPE: DNA
<213> ORGANISM: Clostridium lentocellum

<400> SEQUENCE: 24
gggggcggaa aggattcgac gggggtcaca tctactgggg cagccatccg tagaacgccg      60
gagtctacgt taaaagctgg cacttaaagt aaacgctgaa gataatttag caatcgctgc      120
ctaattaagg cgcagtcctc ctaggtcttc cgcagcctag atcagggctt cgactcgcgg      180
atccttcacc tggcaaagct ttgagccaac gtgaacacta tgaagctact aaaatctaga      240
gcctgtcttt gggcgctaga tggagggaat gtcaaaacaa agaatatgat ggtagagacc      300
acgctatatg ggctttcgga caggggttcg attcccgccg ccttcacca                 349

<210> SEQ ID NO 25
<211> LENGTH: 358
<212> TYPE: DNA
<213> ORGANISM: Clostridium perfringens

<400> SEQUENCE: 25
```

```
ggggctgatt ctggattcga cgggggtaag atgggtttga taagcgagtc gagggaagca      60
tggtgcctcg ataataaagt atgcattaaa gataaacgca aagataatt ttgcattagc      120 agcttaattt agcgctgctc atccttcctc aattgcccac ggttgagagt aagggtgtca     180
tttaaaagtg gggaaccgag cctagcaaag ctttgagcta ggaacggaat ttatgaagct     240
taccaaagag gaagtttgtc tgtggacgtt ctctgaggga atttaaaac acaagactac      300 actcgtagaa agtcttactg gtctgctttc ggacacgggt tcaactcccg ccactcca      358

<210> SEQ ID NO 26
<211> LENGTH: 362
<212> TYPE: DNA
<213> ORGANISM: Clostridium stercorarium

<400> SEQUENCE: 26
gggggcggaa aggattcgac ggggttattg aagcaagagt agcgggtaga ggattctcgt      60
tggcctcttt aaaaaacgag agctaaaaat aaacgcaaac aacgataact acgctttagc    120
tgctgcgtaa gtaacacgca gcccgtcggc cccggggttc ctgcgcctcg ggataccggc    180
gtcatcaagg cagggaacca gccggatcag gcttcaggtc cggtgggatt taatgaagct    240
accgacttat aaagcctgtc tctgggcgtt ataagaaggg aatgtcaaaa cagagactgc    300
acccggagaa gctcttgtgg atatggttcc ggacacgagt tcgattcccg ccgcctccac    360
ca                                                                   362

<210> SEQ ID NO 27
<211> LENGTH: 369
<212> TYPE: DNA
<213> ORGANISM: Enterococcus faecium
<220> FEATURE:
<221> NAME/KEY: misc_feature
<222> LOCATION: (1)..(369)
<223> OTHER INFORMATION: n is an unknown base

<400> SEQUENCE: 27
ggggctgatt atggattcga caggatngtt gagcttgaat tgcgtttcgt aggttacggc      60
tacgttaaaa cgttacagtt aaatataact gctaaaaacg aaacaattc tttcgcttta     120 gctgcctaaa aaccagctag cgaagatcct cccggcatcg cccatgtgct cgggtcaggg    180
tcctaatcga agtgggatac gctaaatttt tccgtctgta aaatttagag gagcttacca    240
gactagcaat acaagaatgc ctgtcactcg gcacgctgta aagcgaacct ttaaatgagt    300
gtctatgaac gtagagattt aagtgggaat atgttttgga cgcgggttca actcccgcca    360
gctccacca                                                            369

<210> SEQ ID NO 28
<211> LENGTH: 353
<212> TYPE: DNA
<213> ORGANISM: Heliobacillus mobilis

<400> SEQUENCE: 28
ggggctgatt ctggattcga cggggaacgt gtttgcttgg gatgcgagcc gggttgccgc      60
caggaccgta aaagggcgg aaggctttaa ttgccgaaga taactacgct ttagctgctt     120
aattgcagtc taacctcttc tcctctgtgc tctcggtgag gatgtaaggg gtcatttaag    180
agagctggct tcgaccaatt ctcggaggtc caagcgagat ttatcgagat agcctgacca    240
acgctctgtc tgccgtgcgg aaggaaggcg aaatctaaaa cgacagacta cgctcgtagt    300
gtcctttgtg ggcatttctt cggacgcggg ttcaactccc gccagctcca cca            353
```

<210> SEQ ID NO 29
<211> LENGTH: 353
<212> TYPE: DNA
<213> ORGANISM: Heliospirillum gestii

<400> SEQUENCE: 29

```
ggggctgatt ctggattcga cggggaacgt gtttgcttag dacgcgagcc gggttgccgc    60
caggaccgta aaagggcgg aaggctttaa ttgccgaaga taactacgct ttagctgctt   120
aattgcagtc taacctcttc tcctctgtgc tctcggtgag gatgtaaggg gtcatttaag   180
agagctggct cgaaccaatt ctcggaggtt cgggtaagac ttatcgagat agcctgacca   240
acgctctgtc tgccgtgcgg aaggatggcg aaatctaaaa cgacagaata cgctcgtagt   300
gtcctttgtg ggcatttctt cggacgcggg ttcaactccc gccagctcca cca           353
```

<210> SEQ ID NO 30
<211> LENGTH: 368
<212> TYPE: DNA
<213> ORGANISM: Lactobacillus acidophilus

<400> SEQUENCE: 30

```
ggggctgatt ctggattcga caggcgtaga cccgcattga ctgcggttcg taggttacgt    60
ctacgtaaaa acgttacagt taaatataac tgcaaataac aaaaattctt acgcattagc   120
tgcttaattt agcgcatgcg ttgctctttg tcggtttact cgtggctgac actgagtatc   180
aacttagcga gttacgttta actacctcac ctgaatagtt gaaagagtc ttagcaggtt    240
agctagtcca tactagccct gttatatggc gttttggact agtgaagttc aagtaatata   300
actatgatcg tagaggtcag tgacgagatg cgtttggaca gcgggttcaa ctcccgccag   360
ctccacca                                                            368
```

<210> SEQ ID NO 31
<211> LENGTH: 360
<212> TYPE: DNA
<213> ORGANISM: Staphylococcus epidermidis

<400> SEQUENCE: 31

```
ggggctgatt ctgcattcga cagggtccc cgagcttatt aagcgtgtgg agggttggct     60
ccgtcatcaa cacatttcgg ttaaatataa ctgacaaatc aaacaataat ttcgcagtag   120
ctgcgtaata gccactgcat cgcctaacag catctcctac gtgctgttaa cgcgattcaa   180
ccctagtagg atatgctaaa cactgccgct tgaagtctgt ttagatgaaa tataatcaag   240
ctagtatcat gttggttgtt tattgcttag catgatgcga aaattatcaa taaactacac   300
acgtagaaag atttgtatca ggacctctgg acgcgggttc aactcccgcc agctccacca   360
```

<210> SEQ ID NO 32
<211> LENGTH: 368
<212> TYPE: DNA
<213> ORGANISM: Streptococcus faecium

<400> SEQUENCE: 32

```
ggggctgatt ctggattcga caggcacagt ttgagcttga attgcgtttc gtaggttacg    60
tctacgttaa aacgttacag ttaaatataa ctgctaaaaa cgaaacaac tcttacgctt    120
tagctgccta aaaacagtta gcgtagatcc tctcggcatc gcccatgtgc tcgagtaagg   180
gtctcaaatt tagtgggata cgtgacaact ttccgtctgt aagttgttaa agagatcatc   240
```

```
agactagcga tacagaatgc ctgtcactcg gcaagctgta aagcgaaacc acaaatgagt    300
tgactatgaa cgtagatttt taagtggcga tgtgtttgga cgcgggttca actcccgccg    360
ttccacca                                                              368
```

<210> SEQ ID NO 33
<211> LENGTH: 328
<212> TYPE: DNA
<213> ORGANISM: Thermoanaerobacterium saccharolyticum

<400> SEQUENCE: 33

```
ggggtagtag aggtaaaagt agcgagccga ggttccatct gctcgtaaaa cggtggactt     60
aaatataaac gcaaacgata atttagctta cgctgcttaa ttacaagcag ccgttcaacc    120
tttgattccc acatcaaagg attgggcgtc gatttagtgg ggaactgatt tatcaaagct    180
ttgagataaa tcggatttta tgaagctacc aaagcagtta tcctgtcact gggagaactg    240
cagagggaat gtcaaaacag tgactgcgct cggagaagct tttactgtga caccttcgga    300
ccggggttca actcccgcca gcccacca                                       328
```

<210> SEQ ID NO 34
<211> LENGTH: 379
<212> TYPE: DNA
<213> ORGANISM: Mycoplasma fermentans

<400> SEQUENCE: 34

```
ggggctgatt ctggattcga catgcattgg gtgatactaa tatcagtagt ttggcagact     60
ataatgcatc taggctttat aatcgcagaa gataaaaaag cagaagaagt taatatttct    120
tcacttatga ttgcacaaaa aatgcaatca caatcaaacc ttgctttcgc ttagttaaaa    180
gtgacaagtg gttttaaagt tgacattttc ctatatattt taaaatcggc ttttaaggag    240
aacaggagtc tgaaagggtt ccaaaaatct atattgtttg catttcggta gtatagatta    300
attagaaatg ataaactgta aaagtattg gtattgactt ggtgtgtgga ctcgggttca    360
actcccgcca gctccacca                                                  379
```

<210> SEQ ID NO 35
<211> LENGTH: 373
<212> TYPE: DNA
<213> ORGANISM: Mycoplasma hyorhinis

<400> SEQUENCE: 35

```
ggggctgatt ctggattcga catacataaa aggatataaa ttgcagtggt cttgtaaacc     60
ataagacaat ttctttacta agcggaaaag aaaacaaaaa agaagattat tcattattaa    120
tgaatgcttc aactcaatca aatctagctt ttgcatttta aaaaactagt agaccaattt    180
gcttctcacg aattgtaatc tttatattag agaatagtta aaaatctgat cactttttaa    240
tgaatttata gatcacaggc ttttttaatc tttttgttat tttagataaa gagtcttct    300 aaaaataact aaactgtagg aatttatatt taattatgcg tggacccggg ttcaactccc    360
gccagctcca cca                                                       373
```

<210> SEQ ID NO 36
<211> LENGTH: 399
<212> TYPE: DNA
<213> ORGANISM: Mycoplasma pirum

<400> SEQUENCE: 36

```
ggggagtcat ggttttgaca tgaatgatgg acccatagag gcagtggggt atgccccta     60
```

```
tagctcaagg tttaaattaa ccgacaaaac tgacgaaaac gttgccgttg atacaaattt    120
attaatcaac caacaagctc aatttaacta cgcatttgca tagtataaaa aaataaattg    180
tgctactcat tgtaattagg ttactaaatt actttgtttt atatagtcct gtaactagtt    240
ctagtgatgt ctataaacta gaatgagatt tatagactta tttgttggcg gttgtgccat    300
agcctaaatc aacaaagaca atttatttat ggtactaaac tgtagattct atgatgaaat    360
tatttgtgga aacgggttcg attcccgcca tctccacca                           399

<210> SEQ ID NO 37
<211> LENGTH: 385
<212> TYPE: DNA
<213> ORGANISM: Mycoplasma salivarium

<400> SEQUENCE: 37
ggggctgatt ctggattcga caggcattcg attcattatg ttgcagtggt ttgcaaacca    60
taaggcacta ggcttttta acgcaaaag accaaaaaac agaagatcaa gcagttgatc     120
tagcatttat gaataattca caaatgcaat caaatctagt tttcgcttag taaaattagt    180
caatttatta tggtgctcaa cataataaat ggtagtatga gcttaatatc atatgatttt    240 agtaatatg ataggatttg taactaaact atgttataga aatttgtaaa ttatatatat     300
gacataggaa atttaattta ctaaactgta gatgcataat gttgaagatg tgtggaccgg    360
ggttcaactc ccgccagctc cacca                                          385

<210> SEQ ID NO 38
<211> LENGTH: 362
<212> TYPE: DNA
<213> ORGANISM: Herpetosiphon aurantiacus

<400> SEQUENCE: 38
gggggcggaa aggattcgac ggggagggcc aatcgtaagt ggcaagccga gacgctgagc    60
ctcgttaaat cggcaacgcc attaactggc aaaaacactt tccgcgctcc tgtagcgctt    120
gctgcctaat taaggcaaca cgtctctact agcctcagcc cgatgggctt gtagcggcga    180
cacttagtcg ggtcgctccc ctagttatgt ctgtgggcta ggggctaaga ttaacaggct    240
ggtcgtggcc cgctttgtct atcgggtggt gcaccgataa gatttaatca atagactacg    300
cttgtagatg cttgcggttt aacttttttgg acgcgggttc gattcccgcc gcctcaccac    360
ca                                                                    362

<210> SEQ ID NO 39
<211> LENGTH: 355
<212> TYPE: DNA
<213> ORGANISM: Thermomicrobium roseum

<400> SEQUENCE: 39
ggggctgatt ctggattcga cagggccgta ggtgcgagga ttgcaggtcg aggtcgccca    60
cgaactcgta aaaggggca gccaagtaac tggcgagcgc gaactcgctc tggctgcgta    120
attcacgcag ccacgtctgc ccggacccctt cctggtggg ttcggagcgg gcgccgcaag    180 accgggtgc ccctggccca agcgccggtc cgggccaggt caagcgtgat ccggctcggc     240
tgaccgggat cctgtcggtg ggagcctggc agcgacagta gaacaccgac taagcctgta    300
gcatatcctc ggctgaacgc tctggacgcg ggttcaactc ccgccagctc cacca          355

<210> SEQ ID NO 40
```

```
<211> LENGTH: 405
<212> TYPE: DNA
<213> ORGANISM: Chlorobium limicola

<400> SEQUENCE: 40
ggggctgatt ctggattcga caggatacgt gtgagatgtc gttgcactcc gagtttcagc      60
atggacggac tcgttaaaca agtctatgta ccattagatg cagacgatta ttcgtatgca     120
atggctgcct gattagcaca agttaactca gacgccatcg tcctgcggtg aatgcgctta     180
ctctgaagcc gccggatggc ataacccgcg cttgagccta cgggttcgcg caagtaagct     240
ccgtacattc atgcccgagg ggctgtgcgg gtaatttctc gggataaggg gacgaacgct     300
gctggcggtg taatcggccc acgaaaaccc aatcaccaga gatgagtgtg gtgactgcat     360
cgagcagtgt tttggacgcg ggttcaactc ccgccagctc cacca                     405

<210> SEQ ID NO 41
<211> LENGTH: 362
<212> TYPE: DNA
<213> ORGANISM: Pirellula staleyi

<400> SEQUENCE: 41
ggggctgatt ctggattcga ccggatagcc tgaagcgaat acggcgtgcc gtggttgatc      60
agatggccac gtaaaaagct gatcacaaac ttaactgccg agagcaatct cgcacttgct     120
gcctaactaa acggtagctt ccgactgagg gctttagccg gagaggccca aaagttggtc     180
accaaatccg gaccgcctcg tgccatgatc gaaacgcacg aggtcaaaaa agtttcgatc     240
tagtgcaggg tgtagccagc agctaggcga caaactgtgc aaaaatcaaa ttttctgcta     300
cgcacgtaga tgtgttcgtg aaaatgtctc gggacggggg ttcaactccc gccactccac     360
ca                                                                   362

<210> SEQ ID NO 42
<211> LENGTH: 346
<212> TYPE: DNA
<213> ORGANISM: Planctomyces limnophilus
<220> FEATURE:
<221> NAME/KEY: misc_feature
<222> LOCATION: (1)..(346)
<223> OTHER INFORMATION: n is an unknown base

<400> SEQUENCE: 42
ggggctgatt ctggattcga caacctctca agaggagcgt ggccactatg ggactcgatt      60
atgttgaatt cgtcatggat cttgaagaga ccttcgacat caaactggat gacaaacatt     120
tttcagcagt caaaacacca cgcgatttgg caatcattat tcgggatcaa ttagctgctg     180
aaggcagaat ctgggatgaa tcgaatgctt ttcgcaaaat ctcgaatttg aattggacga     240
tgttgcccga gttccggatg tggactcaaa tcaaaagctc tctaccagtt tcttttcacc     300
gactgcgtcc cagcacccgt ctcgttcaac tcccgccant ccacca                   346

<210> SEQ ID NO 43
<211> LENGTH: 362
<212> TYPE: DNA
<213> ORGANISM: Planctomyces maris

<400> SEQUENCE: 43
ggggctgatt ctggattcga ctggttcacc gtatgttaag gtggcggtgc cgtggttgat      60
cagttggcca cgtaaaaagc tgatcacaat ctaattgcaa acaagcaatt ttcaatggct     120
gcttaataaa agcaaccccg gcttaggaat ctctgtctga ggagtccgac agctggtcac     180
```

-continued

```
aaaatcagac tggtatcaga tcaatgtccg ctccgtctga tacgagattc gtggtggact      240
ggtttccaac aggctctgtt tatcgtgccc gaagaaacga gactcaaacg ataaaatatg      300
caccgtagag gctttagctg agggttcaca ggacgcgggt tcaactcccg ccagctccac      360
ca                                                                    362

<210> SEQ ID NO 44
<211> LENGTH: 360
<212> TYPE: DNA
<213> ORGANISM: Alcaligenes eutrophus

<400> SEQUENCE: 44
ggggttgatt ctggattcga cgtgggttac aaagcagtgg agggcatacc gaggacccgt      60
cacctcgtta atcaatggga atgcaataac tgctaacgac gaacgttacg cactggccgc      120
ttaattgcgg ccgtcctcgc actggctcgc tgacgggcta gggtcgcaag accacgcgag      180
gtcatttacg tcagataagc tccggaaggg tcacgaagcc ggggacgaaa acctagtgac      240
tcgccgtcgt agagcgtgtt cgtccgcgat gcgccggtta aatcaaatga cagaactaag      300
tatgtagaac tctctgtgga gggcttacgg acgcgggttc aactcccgcc agctccacca      360

<210> SEQ ID NO 45
<211> LENGTH: 362
<212> TYPE: DNA
<213> ORGANISM: Alcaligenes faecalis

<400> SEQUENCE: 45
gggggcggaa aggattcgac gggggtcaag aagcagcaca gggcgtgtcg agcaccagta      60
cgctcgtaaa tccactggaa aactataaac gccaacgacg agcgtttcgc tctagccgct      120
taaggctggg ccactgcact aatttgtctt tgggttaggt agggcaacct acagcagtgt      180
tatttacaaa gaatcgaatc ggtctgcgcc acgaagtccg gttctaaaac ttagtggatc      240
gccaaggaaa ggcctgtcaa ttggcatagt ccaaggttaa aacttaaaat taattgacta      300
cacatgtaga actgtctgtg gacggcttgc ggacgggggt tcgattcccg ccgcctccac      360
ca                                                                    362

<210> SEQ ID NO 46
<211> LENGTH: 366
<212> TYPE: DNA
<213> ORGANISM: Chromobacterium violaceum

<400> SEQUENCE: 46
ggggctgatt ctggattcga cgggggttgc gaagcagatg agggcatacc gggatttcag      60
tcaccccgta aaacgctgaa tttatatagt cgcaaacgac gaaacttacg ctctggcagc      120
ctaacggccg gccagacact acaacggttc gcagatgggc cggggcgtc aaaaccctgt      180 agtgtcactc tacatctgct agtgctgttc cgggttactt ggttcagtgc gaaataatag      240
gtaactcgcc aaagtccagc ctgtccgtcg gcgtggcaga ggttaaatcc aaatgacacg      300
actaagtatg tagaactcac tgtagaggac tttcggacgc gggttcaact cccgccagct      360
ccacca                                                                366

<210> SEQ ID NO 47
<211> LENGTH: 378
<212> TYPE: DNA
<213> ORGANISM: Hydrogenophaga palleroni
```

-continued

```
<400> SEQUENCE: 47
ggggctgatt ctggattcga cgtgggttcg gacgcgcagc agggcatgtc gaggttctgt      60
cacctcgtaa atcagcagaa aaaaaccaac tgcaaacgac gaacgtttcg cactcgccgc     120
ttaaacaccg gtgagccttg caacagcagg ccgatgggct gggcaagggg gtcgcaagac     180
ctcccggctg caaggtaatt tacatcggct ggttctgcgt cggcaccttg gcgcaggat     240 gagattcaag gatgctggct tcccgtttag cgtgccactg cgcgactcgg gcggcgagac     300
ccaaatcaga cggctacaca tgtagaactg ctcgaaaaag gcttgcggac ggggggttcaa    360 ctcccgccag ctccacca                                                   378

<210> SEQ ID NO 48
<211> LENGTH: 365
<212> TYPE: DNA
<213> ORGANISM: Methylobacillus glycogenes

<400> SEQUENCE: 48
gggggcggaa aggattcgac gggggttgca aagcagcgca gggcataccg aggcctagtc      60
acctcgtaaa taaactagaa caagtatagt cgcaaacgac gaaacttacg ctctagccgc     120
ttaatcccgg ctggacgctg caccgaaggg cctctcggtc gggtggggta acccacagca     180
gcgtcattaa gagaggatcg tgcgatattg gttacttaa tatcgtatta aatccaaggt      240
aactcgcctg ctgtttgctt gctcgttggt gagcatcagg ttaaatcaaa caacacagct     300
aagtatgtag aactgtctgt ggagggcttg cggacggggg ttcgattccc gccgcctcac     360
cacca                                                                 365

<210> SEQ ID NO 49
<211> LENGTH: 362
<212> TYPE: DNA
<213> ORGANISM: Nitrosomonas cryotolerans

<400> SEQUENCE: 49
ggggctgatt ctggattcga cgtgggttgc aaagcagcgc agggcatacc gaggaccaga      60
atacctcgta aatacatctg gaaaaaaata gtcgcaaacg acgaaaacta cgctttagcc     120
gcttaatacg gctagcctct gcaccgatgg gccttaacgt cgggtctggc aacagacagc     180
agagtcatta gcaaggatcg cgttctgtag ggtcactttta cagaacgtta aacaataggt     240
gactcgcctg ccatcagccc gccagctggc ggttgtcagg ttaaattaaa gagcatggct     300
aagtatgtag aactgtctgt agaggacttg cggacgcggg ttcaactccc gccagtccac     360
ca                                                                    362

<210> SEQ ID NO 50
<211> LENGTH: 378
<212> TYPE: DNA
<213> ORGANISM: Pseudomonas testosteroni

<400> SEQUENCE: 50
ggggctgatt ctggattcga cgtgggttcg ggaccggtgc ggtgcatgtc gagcttgagt      60
gacgctcgta atctccatt caaaaaacta actgcaaacg acgaacgttt cgcactcgcc     120
gcttaatccg gtgagccttg caacagcacg ctagtgggct gggcaagggg gtagcaatac     180
ctcccggctg caagggaatt ttcattagct ggctggatac cgggcttctt ggtatttggc     240
gagattttag gaagctggct acccaagcag cgtgtgcctg cggggtttgg gtggcgagat     300
ttaaaacaga gcactaaaca tgtagatctg tccggcgaag gcttacggac gcggggttcaa   360
```

```
ctcccgccag ctccacca                                              378
```

<210> SEQ ID NO 51
<211> LENGTH: 360
<212> TYPE: DNA
<213> ORGANISM: Ralstonia pickettii

<400> SEQUENCE: 51

```
gggggcggaa aggattcgac gggggttgcg aagcagcgga gggcataccg aggacccgtc   60
acctcgttaa tcaatgggaa tgcaataact gctaacgacg aacgttacgc actggcagcc  120
taagggccgc cgtcctcgca ctggctcgct gacgggctag ggtcgcaaga ccagcgaggt  180
catttacgtc agataagctt taggtgagtc acgggcctag agacgaaaac ttagtgaatc  240
gccgtcgtag agcgtgttcg tccgcgatgc ggcggttaaa tcaaatgaca gaactaagta  300
tgtagaactc tctgtggagg gcttgcggac gcgggttcga ttcccgccgc ctcaccacca  360
```

<210> SEQ ID NO 52
<211> LENGTH: 386
<212> TYPE: DNA
<213> ORGANISM: Variovorax paradoxus

<400> SEQUENCE: 52

```
ggggctgatt ctggattcga cgtgggttcg gagtcgcagc ggggcatgtc gagctgaatg   60
cgctcgtaaa acagattcaa acaaactaac tgcaaacgac gaacgtttcg cactcgctgc  120
ttaattgcca gtgagccttg caacagttgg ccgatgggct gggcaagggg gtctggagca  180
atcctgacct cccggctgca aggataacta catgggctgg ctccgatccg ggtaccttgg  240
gtcggggcga gaaaataggg tactggcgtc cggtttagcg tgtgactgcg cgactccgga  300
agcgagactc aaaacagatc actaaacatg tagaactgcg cgatgaaggc ttgcggacgg  360
gggttcaact cccgccagct ccacca                                      386
```

<210> SEQ ID NO 53
<211> LENGTH: 346
<212> TYPE: DNA
<213> ORGANISM: Bdellovibrio bacteriovirus

<400> SEQUENCE: 53

```
ggggcggaa aggattcgac gggggtgctg aagcataagg agcataccgg ggcggatgag    60
gacctcgtta aaaacgtcca ctttgtaatt ggcaacgatt acgcacttgc agcttaatta  120
agcagcacga tcaaccttgt ggtggttccg cacttggatt gatcgtcatt tagggacctc  180
ggcgtgttgg gttttctcca gcagacatgc ttaaatttac tgggggagag gtcttaggga  240
ttttgtctgt ggaagcccga ggaccaatct aaaacactga ctaagtatgt agcgccttat  300
cgtggatcat ttgcggacgg gggttcgatt cccgccgcct ccacca                346
```

<210> SEQ ID NO 54
<211> LENGTH: 366
<212> TYPE: DNA
<213> ORGANISM: Myxococcus xanthus

<400> SEQUENCE: 54

```
gggggcggaa aggattcgac gggggcattg aagttcgaga cgcgtgccga gcttgtcagg   60
tagctcgtaa attcaacccg gcaaagacac aaaagccaac gacaacgttg agctcgcgct  120
ggctgcctaa aaacagccca tagtgcgcgg tcccccgcc ctcggcctgt gggggttggga  180
```

-continued

```
cagaccgtca taatgcaggc tggctgccga gggtgcctgg acccgaggtg gcgagatctt   240
cccaggaccg gctctgagta tcccgtccgt gggagcctca gggacgtagc aaatcgcgga   300
ctacgcacgt agggtcgaag agcggacggc tttcggacgc gggttcgatt cccgccgcct   360
ccacca                                                              366
```

<210> SEQ ID NO 55
<211> LENGTH: 380
<212> TYPE: DNA
<213> ORGANISM: Sulfurospirillum deleyianum

<400> SEQUENCE: 55

```
ggggctgatt ctggattcga caggagtagt tttagcttat ggctgcatgt cgggagtgag    60
ggtcttccgt tacacaacct tcaaacaata actgctaaca acagtaacta tcgtcctgct   120
tacgcgctag ctgcgtaagt ttaacaaata atggactgct ctcccctttg atgctatctt   180
aggaggtctt ggagagtatc atagatttga tagctatatt acatgaacgc ctttacatgt   240
aatgaagtta aaggctcgtt ttgcgtagtt ttctgattgt tgtacgaagc aaaattaaac   300
actatcaaca atatctaagc atgtagacgt cataggtggc tatttttgga ctgcgggttc   360
aactcccgcc agctccacca                                               380
```

<210> SEQ ID NO 56
<211> LENGTH: 359
<212> TYPE: DNA
<213> ORGANISM: Chromatium vinosum

<400> SEQUENCE: 56

```
ggggctgatt ctggattcga cgtgggtcgc gaaacctaag gtgcatgccg aggtgcggtt    60
gacctcgtaa aaccctccgc aaacttatag ttgccaacga cgacaactac gctctcgctg   120
cttaatccca gcgggcctct gaccgtcact tgcctgtggg cggcggattc caggggtaac   180
ctcacacagg atcgtggtga cgggagtccg gacctgatcc actaaaacct aacggaatcg   240
ccgactgatc gccctgccct tcgggcggca gaaggctaaa aacaatagag tgggctaagc   300
atgtaggacc gagggcagag ggcttgcgga cgcgggttca actcccgcca gctccacca   359
```

<210> SEQ ID NO 57
<211> LENGTH: 395
<212> TYPE: DNA
<213> ORGANISM: Pseudomonas fluorescens

<400> SEQUENCE: 57

```
ggggctgatt ctggattcga cgccggttgc gaaccttag gtgcatgccg agttggtaac    60
agaactcgta aatccactgt tgcaactttc tatagttgcc aatgacgaaa cctacgggga   120
atacgctctc gctgcgtaag cagccttagc ccttccctcc tggtaccttc gggtccagca   180
atcatcaggg gatgtctgta aacccaaagt gattgtcata tagaacagaa tcgccgtgca   240
gtacgttgtg gacgaagcgg ctaaaactta cacaactcgc ccaaagcacc ctgcccgtcg   300
ggtcgctgag ggttaactta atagacacgg ctacgcatgt agtaccgaca gcagagtact   360
ggcggacgcg ggttcaactc ccgccagctc cacca                              395
```

<210> SEQ ID NO 58
<211> LENGTH: 362
<212> TYPE: DNA
<213> ORGANISM: Borrelia afzelii

<400> SEQUENCE: 58

-continued

```
gggctgatt  ctggattcga  ctgaaaatgc  taatattgta  agttgcaagc  agagggaatc      60
tcttaaaact  tctaaaataa  atgcaaaaaa  taataacttt  acaagttcaa  accttgtaat    120
ggctgcttaa  gttagcagag  agttttgttg  aatttggctt  tgagattcac  ttatactctt    180
ttagacatcg  aagcttgctt  aaaaatgttt  tcaagttgat  ttttagggac  ttttatactt    240
gagagcaatt  tggcggtttg  ctagtatttc  caaaccatat  tgcttagtaa  aatactagat    300
aagcttgtag  aagcttatag  tattgttttt  aggacgcggg  ttcaactccc  gccagtccac    360
ca                                                                        362
```

<210> SEQ ID NO 59
<211> LENGTH: 363
<212> TYPE: DNA
<213> ORGANISM: Borrelia crocidurae

<400> SEQUENCE: 59

```
gggctgatt  ctggattcga  ctaagaactt  tagtagcata  aatggcaagc  agagtgaatc      60
tcttaaaact  tctttaataa  atgcaaaaaa  taataacttt  acaagttcag  atcttgtaat    120
ggctgcttaa  tttagcagag  agttttgttg  gattttgctt  tgaggttcaa  cttatactct    180
ttaagacatc  aaagtatgcc  taaaaatgtt  tcaagttgat  ttttagggac  ctttaaactt    240
gagagtaatt  tggtggtttg  cttgttttcc  aagccttatt  gcttttttcta  aaaattagct    300 aagcttgtag  atatttatga  tattattttt  aggacgcggg  ttcaactccc  gccagttcca    360
cca                                                                       363
```

<210> SEQ ID NO 60
<211> LENGTH: 365
<212> TYPE: DNA
<213> ORGANISM: Borrelia hermsii

<400> SEQUENCE: 60

```
gggctgatt  ctggattcga  ctaaaaactt  tagtagcata  aattgcaagc  agagggaatc      60
tcttaaaact  tctttaataa  atgcaagaaa  taataacttt  acaagttcaa  atcttgtaat    120
ggctgcttaa  attagcagag  agttctgctg  gattttgctt  tgaggttcag  cttatactct    180
tttaagacat  caaagcttgc  ttaaaaatat  ttcaagttga  ttttttaggga  cttttaaatt    240 tgagagtaat  ttggcggttt  gctagttttt  ccaaaccttta  ttacttaaag  aaaacactag    300
ctaagcttgt  agatatttat  gatattattt  ttaggacgcg  ggttcaactc  cgccagctc    360 cacca                                                                     365
```

<210> SEQ ID NO 61
<211> LENGTH: 363
<212> TYPE: DNA
<213> ORGANISM: Borrelia garinii

<400> SEQUENCE: 61

```
gggctgatt  ctggattcga  ctgaaaatgc  gaatattgta  agttgcaggc  agagggaatc      60
tcttaaaact  tctaaaataa  atgcaaaaaa  taataacttt  acaagctcaa  accttgtaat    120
ggctgcttaa  gttagcaggg  agtttcgttg  aatttggctt  tgaggttcac  ttatactctt    180
ttcgatatcg  aagcttgctt  aaaaatgttt  tcaagttaat  ttttagggac  ttttgtactt    240
gagagcaatt  tggcggtttg  ctagtatttc  caaaccatat  tgcttaagta  aaatgctaga    300
taagcttgta  gaagcttata  atattgttttt  taggacgcgg  gttcaactcc  cgccagtcca    360
```

```
                                                                 -continued cca                                                                         363

<210> SEQ ID NO 62
<211> LENGTH: 357
<212> TYPE: DNA
<213> ORGANISM: Thermodesulfobacterium commune

<400> SEQUENCE: 62
gggggcggaa aggattcgac ggggataggt aggattaaac agcaggccgt ggtcgcaccc            60
aaccacgtta aatagggtgc aaaaacacaa ctgccaacga atacgcctac gctttggcag          120
cctaagcgtg ctgccacgca cctttagacc ttgcctgtgg gtctaaaggt gtgtgaccta          180
acaggctttg ggaggcttaa tcggtggggt taagcctccc gagattacat cccacctggt          240
agggttgctt ggtgcctgtg acaagcaccc tacgagattt tcccacaggc taagcctgta          300
gcggtttaat ctgaactatc tccggacgcg ggttcgattc ccgccgcctc cccacca            357

<210> SEQ ID NO 63
<211> LENGTH: 358
<212> TYPE: DNA
<213> ORGANISM: Thermotoga neapolitana
<220> FEATURE:
<221> NAME/KEY: misc_feature
<222> LOCATION: (1)..(358)
<223> OTHER INFORMATION: n is an unknown base

<400> SEQUENCE: 63
gggggcggaa aggattcgac ggggatggag tcccctggga agcgagccga ggtccccacc            60
tcctcgtaaa aaaggtggga acacgaataa gtgccaacga acctgttgct gttgccgcct          120
aatagatagg cggccgtcct ctccggagtt ggctgggctc cggaagaggg cgtgagggat          180
ccagcctacc gatctgggct ccgccttccg gcccggatcg ggaaggttca ggaaggctgt          240
gggaagcgac accctgcccg tgggggggtcc ttcccgagac acgaaacacg ggctgcgctc          300
ggagaagccc aggggcctcc atcttcngac gcgggttcga ttcccgccac ctccacca           358

<210> SEQ ID NO 64
<211> LENGTH: 347
<212> TYPE: DNA
<213> ORGANISM: Deinococcus proteolyticus

<400> SEQUENCE: 64
gggggcggaa aggattcgac ggggggaacgg aaagcgctgc tgcgtgccga ggagccgttg           60
gcctcgtaaa caaacggcaa agccattaac tggcgaaaat aactacgctc tcgctgctta          120
agtgagacag tgaccacgta gccccgcctt tggcgacgtg tgaactgaga caaaagaagg          180
ctagcttagg tgaggttcca tagccaaaag tgaaaccaaa tggaaataag gcggacggca          240 gcctgttttgc tggcagccca ggcccgacaa tttaagagca gactacgcac gtagatgcac          300
gctggatgga cctttggacg cgggttcgat tcccgccagc tccacca                       347

<210> SEQ ID NO 65
<211> LENGTH: 352
<212> TYPE: DNA
<213> ORGANISM: Prosthecobacter fusiformis

<400> SEQUENCE: 65
ggggctgatt ctggattcga cggggagtac aaggatcaaa agctgcaagc cgaggtgccg            60
ttacctcgta aaacaacggc aaaaaagaag tgccaacaca aatttagcat tagctgctta          120
atttagcagc tacgctcttc taacccgggc tggcagggtt agaagggtgt cataatgagc          180
```

```
cagctgcccc ttccgactcc cctaaggaag ggaaagatgt aggggatagg tgcttacaga      240
atcctgcggg agggagtctg taagtgccga aaagttaaaa ctcccgctaa gcttgtagag      300
gcttttgatt cttgctctct ggacgcgggt tcaactcccg ccagctccac ca              352
```

<210> SEQ ID NO 66
<211> LENGTH: 329
<212> TYPE: DNA
<213> ORGANISM: Verrucomicrobium spinosum
<220> FEATURE:
<221> NAME/KEY: misc_feature
<222> LOCATION: (1)..(329)
<223> OTHER INFORMATION: n is an unknown base

<400> SEQUENCE: 66

```
gggnnnnatt tggaattcgc cgaatgctag aagtggaggc tgcatgccgc ggatgattcg       60
ttggccgctt taccaattcg gatcaaacaa ctaaatgcgg actctaacga gcttgccctc      120
gccgcttaat tgacggtgac gttcctccag tgaagtctgt gaattggagg agcgactact      180
tacaggctgg ccaaaagagc gggcgaccgg ccccaaggcg agatctacag gccgctggat      240
ggacggcatc ctggcagtag gaggctggac atcgagatca aatnattgcc tgagcatgga      300
gacgctttca taaaggngtt cggacaggg                                         329
```

<210> SEQ ID NO 67
<211> LENGTH: 318
<212> TYPE: RNA
<213> ORGANISM: Thermoanaerobacterium saccharolyticum

<400> SEQUENCE: 67

```
cggggguagu agagguaaaa guagcgagcc gagguuccau cugcucguaa aacgguggac       60
uuaaauauaa acgcaaacga uaauuuagcu uacgcugcuu aauuacaagc agccguucaa      120
ccuuugauuc ccacaucaaa ggauugggcg ucgauuuagu ggggaacuga uuuaucaaag      180
cuuugagaua aaucggauuu uaugaagcua ccaaagcagu uauccugucA cugggagaac      240
ugcagaggga augucaaaac agugacgcg cucggagaag cuuuuacugu gacaccuucg      300 gaccggdgguu caacucccc                                                   318
```

<210> SEQ ID NO 68
<211> LENGTH: 187
<212> TYPE: RNA
<213> ORGANISM: Clostridium acetobutylicum

<400> SEQUENCE: 68

```
aaucuggcgu cgagagcggg gaaacgagcc uuacaaagcu uugaguaagg aacggaauuu       60
augaagcuac ugaagugaaa agcuuguuug uaggcguuuc auggagggaa uguuaaaaua      120
caaacugcac ucggagaugc uuaaaugaaa ccauuuucgg acagggguuc gauuccccuc      180
gccucca                                                                 187
```

<210> SEQ ID NO 69
<211> LENGTH: 335
<212> TYPE: RNA
<213> ORGANISM: Clostridium stercorarium

<400> SEQUENCE: 69

```
cggggguauu gaagcaagag uagcgdgguag aggauucucg uuggcccucuu uaaaaaacga      60 gagcuaaaaa uaaacgcaaa caacgauaac uacgcuuuag cugcugcgua aguaacacgc      120
```

```
agcccgucgg ccccggggu ccugcgccuc gggauaccgg cgucaucaag gcagggaacc      180
agccggauca ggcuucaggu ccggguggau uaaugaagc uaccgacuua uaaagccugu      240
cucugggcgu uauaagaagg gaaugucaaa acagagacac caaugcaccc ggagaagcuc     300
uuguggauau gguccggac acgaguucga uuccc                                 335

<210> SEQ ID NO 70
<211> LENGTH: 336
<212> TYPE: RNA
<213> ORGANISM: Clostridium perfringens

<400> SEQUENCE: 70
cggggguaag auggguuuga uaagcgaguc gagggaagca uggugccucg auaauaaagu     60
augcauuaaa gauaaacgca gaagauaauu uugcauuagc agcuuaauuu agcgcugcuc   120
auccuuccuc aauugcccac gguugagagu aagggugucu uuuaaaagug gggaaccgag   180
ccuagcaaag cuuugagcua ggaacggauu uuaugaagcu agaggaagu uugucugugg    240 acguucucug agggaauuuu aaaacacaag acacuaaaau cuaguacacu cguagaaagu    300
cuuacugguc ugcuuucgga cacgguuca acuccc                              336

<210> SEQ ID NO 71
<211> LENGTH: 305
<212> TYPE: RNA
<213> ORGANISM: Clostridium lentocellum

<400> SEQUENCE: 71
cgggggucac aucuacuggg gcagccaucc guagaacgcc ggagucuacg uuaaaagcug     60
gcacuuaaag uaaacgcuga agauaauuua gcaaucgcug ccuaauuaag gcgcaguccu   120
ccuaggucuu ccgcagccua gaucagggcu ucgacucgcg gauccuucac cuggcaaagc   180
uuugagccaa cgugaacacu augaagcuag ccugucuuug ggcgcuagau ggagggaaug   240
ucaaaacaaa gaauaugaug guagagacca cgcuauaugg gcuuucggac aggggucga    300 uuccc                                                               305

<210> SEQ ID NO 72
<211> LENGTH: 319
<212> TYPE: RNA
<213> ORGANISM: Heliobacillus mobilis

<400> SEQUENCE: 72
cggggaacgu guuugcuugg gaugcgagcc ggguugccgc caggaccgua aaagggcgg      60 aaggcuuuaa uugccgaaga uaacuacgcu uuagcugcuu uauugcaguc uaaccucuuc   120
uccucugugc ucucggugag gauguaaggg gucauuuaag agagcuggcu ucgaccaauu   180
cucggagguc caagcgagau uuaucgagau agccugacca acgcucuguc ugccgugcgg   240
aaggaaggcg aaaucuaaaa cgacagauac gcucguagug uccuuugugg gcauucuuc   300 ggacgcgggu ucaacuccc                                                319

<210> SEQ ID NO 73
<211> LENGTH: 321
<212> TYPE: RNA
<213> ORGANISM: Heliospirillum gestii

<400> SEQUENCE: 73
cggggaacgu guuugcuuag gacgcgagcc ggguugccgc caggaccgua aaagggcgg      60 aaggcuuuaa uugccgaaga uaacuacgcu uuagcugcuu aauugcaguc uaaccucuuc   120
```

```
uccucugugc ucucggugag gauguaaggg gucauuuaag agagcuggcu cgaaccaauu    180
cucggagguu cggguaagac uuaucgagau cagccugacc aacgcucugu cugccgugcg    240
gaaggauggc gaaaucuaaa acgacagaau acgcucguag uguccuugu gggcauuucu     300 ucggacgcgg guucaacucc c                                              321
```

<210> SEQ ID NO 74
<211> LENGTH: 325
<212> TYPE: RNA
<213> ORGANISM: Brevibacillus brevis

<400> SEQUENCE: 74

```
cggggauggu agagcaugag aagcgagccg gggggguugcg gaccucguca ccaacgcaaa    60
cgccauuaac uggcaacaaa caacuuucuc ucgcugcuua auaaccagug aggcucuccc    120
acugcaucgg cccgugugcc guggauaggg cucaacuuua acgggcuacg ccggaggcuu    180
ccgccuggag ccaaaggaag aagaccaauc aggcuaggug ccaggucagc gcgucacucc    240
gcgaaucugu caccgaaacu cuaaacgagu gacugcgcuc ggagaugcuc auguaucgcu    300 guuucggac ggggguucga uuccc                                           325
```

<210> SEQ ID NO 75
<211> LENGTH: 360
<212> TYPE: RNA
<213> ORGANISM: Bacillus subtilis

<400> SEQUENCE: 75

```
ggggacguua cggauucgac agggauggau cgagcuugag cugcgagccg agaggcgauc    60
ucguaaacac gcacuaaaau auaacuggca aaacuaacag uuuuaaccaa aacguagcau   120
uagcugccua auaagcgcag cgagcucuuc cugacauugc cuaugugucu gugaagagca    180
cauccaagua ggcuacgcuu gcguucccgu cugagaacgu aagaagagau gaacagacua   240
gcucucggaa ggcccgcccg caggcaagaa gaugagugaa accauaaaua ugcaggcuac    300
gcucguagac gcuuaaguaa ucgauguuuc uggacguggg uucgacuccc accgucucca   360
```

<210> SEQ ID NO 76
<211> LENGTH: 325
<212> TYPE: RNA
<213> ORGANISM: Bacillus badius

<400> SEQUENCE: 76

```
cagggauagu ucgagcuugg gcugcgagcc ggagggccgu cuucguacca acgcaaacgc    60
cuaaauauaa cuggcaaaaa agauuuagcu uuagcugccu aauauaggu cagcugcucc    120 ucccgcuauc guccauguag ucggguaagg gguccaaacu uaguggacua cgccggaguu    180
cuccgccugg ggacaaagga agagaucaau caggcuagcu gcccggacgc ccgucgauag    240
gcaaaaggaa cagugaaccc caaauauauc gacuacgcuc guagacguuc aaguggcguu    300
aucuuuggac gugggguucaa cuccc                                         325
```

<210> SEQ ID NO 77
<211> LENGTH: 341
<212> TYPE: RNA
<213> ORGANISM: Bacillus megaterium

<400> SEQUENCE: 77

```
ggggacguua cggauucgac aggguaguuc gagcuuaggu ugcgagucga ggagauggcc    60
```

-continued

| ucguuaaaac aucaacgcca auaauaacug gcaaaucuaa caauaacuuc gcuuuagcug | 120 |
| cauaauagua gcuuagcguu ccucccucca ucgcccaugu gguaggguaa gggacucacu | 180 |
| uuaagugggc uacgccggag uucgccgucu gaggacgaag gaagagaaua aucagacuag | 240 |
| cgacugggac gccuguuggu aggcagaaca gcucgcgaau gaucaauaug ccaacagccg | 300 |
| uacacucgua gacgcuuaag uggccauauu ucuggacgug g | 341 |

<210> SEQ ID NO 78
<211> LENGTH: 315
<212> TYPE: RNA
<213> ORGANISM: Bacillus thermoleovorans

<400> SEQUENCE: 78

| cgggggguagg ucgagcuuaa gcggcgagcc gaggggacg uccucguaaa acgucaccu | 60 |
| aaagauaacu ggcaaacaaa acuacgcuuu agcugccuaa uugcugcagc uagcuccucc | 120 |
| cgccaucgcc cgcguggcgu ucgaggggcu cauauggagc gggcuacgcc caaauccgcc | 180 |
| gccugaggau gagggaagag acgaaucagg uccgggagg ccugucggua ggcggaacgg | 240 |
| acggcgaagc gaaauauacc gacuacgcuc guagaugcuu aaguggcgau gccucuggac | 300 |
| guggguucga uuccc | 315 |

<210> SEQ ID NO 79
<211> LENGTH: 335
<212> TYPE: RNA
<213> ORGANISM: Enterococcus faecium

<400> SEQUENCE: 79

| caggcacagu uugagcuuga auugcguuuc guagguuacg ucuacguuaa aacguuacag | 60 |
| uuaaauauaa cugcuaaaaa cgaaaacaac ucuuacgcuu uagcugccua aaaacaguua | 120 |
| gcguagaucc ucucggcauc gcccaugugc ucgaguaagg gucucaaauu uagugggaua | 180 |
| cgugacaacu uuccgucugu aaguuguuaa agagaucauc agacuagcga uacagaaugc | 240 |
| cugucacucg gcaagcugua aagcgaaacc acaaaugagu ugauaugaac guagauuuuu | 300 |
| aaguggcgau guguuuggac gcggguucaa cuccc | 335 |

<210> SEQ ID NO 80
<211> LENGTH: 364
<212> TYPE: RNA
<213> ORGANISM: Enterococcus faecalis

<400> SEQUENCE: 80

| gggggcguua cggauucgac aggcauaguu gagcuugaau ugcguuucgu agguuacggc | 60 |
| uacguuaaaa cguuacaguu aaauauaacu gcuaaaaacg aaaacaauuc uuucgcuuua | 120 |
| gcugccuaaa aaccagcuag cgaagauccu cccggcaucg cccaugugcu cggucaggg | 180 |
| uccuaaucga agugggauac gcuaaauuuu ccgucugua aauuuagag gagcuuacca | 240 |
| gacucagcaa uacagaaugc cugucacucg gcacgcugua aagcgaaccu uuaaaugagu | 300 |
| guuaugaacg uagagauuua aguggcaaua uguuuggacg cggguucgac ucccgccguc | 360 |
| ucca | 364 |

<210> SEQ ID NO 81
<211> LENGTH: 346
<212> TYPE: RNA
<213> ORGANISM: Streptococcus pyogenes

<400> SEQUENCE: 81

-continued

```
ggggucguua cggauucgac aggcauuaug aggcauguuu ugcgucccau cggcagaugu    60
aaauugccag uuaaauauaa cugcaaaaaa uacaaacucu uacgcuuuag cugccuaaaa   120
accagcuagc gugacuucua caagauugcu ugugccugu uagaagcucu aaaauagcaa   180
gcuacgguua cgaaauuguc uaguuucgug acaagagauu gauagacucc gcaaacuaau   240
ggcuugaguu augugucuuu aguuuguuaa augaagacau aaccuaugga cguagacaaa   300
uauguuggca gguguuugga cgugggguucg acucccacca gcucca              346
```

<210> SEQ ID NO 82
<211> LENGTH: 344
<212> TYPE: RNA
<213> ORGANISM: Streptococcus pneumoniae

<400> SEQUENCE: 82

```
ggggucguua cggauucgac aggcauuaug aggcauauuu ugcgacucgu guggcgacgu    60
aaacgcucag uuaaauauaa cugcaaaaaa uaacacuucu uacgcucuag cugccuaaaa   120
accagcaggc ugacccgau uuggauugcu cguguucaau gacaggucuu auuauuagcg   180
agauacgauu aagccuuguc uagcgguuug auaagagauu gauagacucg caguuucuag   240
acuugaguua ugugucgagg ggcuguuaaa auaauacaua acuaugguug uagacaaaua   300
uguuggcagg uguuuggacg uggguucgac ucccaccggc ucca                    344
```

<210> SEQ ID NO 83
<211> LENGTH: 364
<212> TYPE: RNA
<213> ORGANISM: Streptococcus gordonii

<400> SEQUENCE: 83

```
ggggucguua cggauucgac aggcauuaug aggcauauuu ugcgacucau cuagcggaug    60
uaaaacgcca guuaaauaua acugcaaaaa auaauacuuc uuacgcuuua gcugccuaaa   120
aaccagcggg cgugacccga uucggauugc uugugucuga ugacaggucu auuauuagc   180 aagcuacggu agaaucuugu cuagugauuu uacaagagau ugauagacua cguuagaacu   240
gagucagccg cuugauuugg gcuugaguua ugugucaaaa ucaaguuaaa acaauacaua   300
gcuaugguug uagacaaaua uguuggcaga guuuuggacg uggguucgac ucccaccggc   360
ucca                                                                 364
```

<210> SEQ ID NO 84
<211> LENGTH: 329
<212> TYPE: RNA
<213> ORGANISM: Streptococcus mutans

<400> SEQUENCE: 84

```
ggggucguua cggauucgac aggcauuaug agaccuauuu ugcgacucau cuagcggaug    60
uaaaacgcca guuaaauaua acugcaaaaa auacaaauuc uuacgcagua gcugccuaaa   120
aaccagccug ugugaucaau aacaaauugc uuguguuugu ugauuggucu auuguuaac   180 aagcugcugu ucuaaaagag uucuacugac uccgcaucgu uagaguuuga guuauguauu   240 guaacgugu uaaauaaaca cauaaccuau aguugagac aaauggguua gcagauguuu   300
ggacgugggu ucgacucccca ccggcucca                                    329
```

<210> SEQ ID NO 85
<211> LENGTH: 328
<212> TYPE: RNA

<213> ORGANISM: Staphylococcus epidermidis

<400> SEQUENCE: 85

| | | | | | |
|---|---|---|---|---|---|
| caggggucccc | cgagcuuauu | aagcgugucg | gagggguuggc | uccgucauca | acacauuucg | 60 |
| guuaaauaua | acugacaaau | caaacaauaa | uuucgcagua | gcugcguaau | agccacugca | 120 |
| ucgccuaaca | gcaucuccua | cgugcuguua | acgcgauuca | acccuaguag | gauaugcuaa | 180 |
| acacugccgc | uugaagucug | uuuagaugaa | auauaaucaa | gcaguauca | uguugguugu | 240 |
| uuauugcuua | gcaugaugcg | aaaauuauca | auaaacuaca | cacguagaaa | gauuuguauc | 300 |
| aggaccucug | gacgcggguu | caacuccc | | | | 328 |

<210> SEQ ID NO 86
<211> LENGTH: 359
<212> TYPE: RNA
<213> ORGANISM: Staphylococcus aureus

<400> SEQUENCE: 86

| | | | | | |
|---|---|---|---|---|---|
| ggggacguuc | auggauucga | caggggucccc | ccgagcucau | uaagcgugucc | ggaggguugu | 60 |
| cuucgucauc | aacacacaca | guuuauaaua | acuggcaaau | caaacaauaa | uuucgcagua | 120 |
| gcugccuaau | cgcacucugc | aucgccuaac | agcauuuccu | augugcuguu | aacgcgauuc | 180 |
| aaccuuaaua | ggauaugcua | aacacugccg | uugaagucu | guuuagaaga | acuuaauca | 240 |
| aacuagcauc | auguugguug | uuuaucacuu | ucaugaugc | gaaaccuauc | gauaaacuac | 300 |
| acacguagaa | agauguguau | caggaccuuu | ggacgcgggu | ucaaauccccg | ccgucucca | 359 |

<210> SEQ ID NO 87
<211> LENGTH: 334
<212> TYPE: RNA
<213> ORGANISM: Lactobacillus acidophilus

<400> SEQUENCE: 87

| | | | | | |
|---|---|---|---|---|---|
| caggcguaga | cccgcauuga | cugcgguucg | uagguuacgu | cuacguaaaa | acguuacagu | 60 |
| uaaauauaac | ugcaaauaac | aaaaauucuu | acgcauuagc | ugcuuaauuu | agcgcaugcg | 120 |
| uugcucuuug | ucgguuuacu | cgguggcugac | acugaguauc | aacuuagcga | guuacguuua | 180 |
| acuaccucac | cugaauaguu | gaaaagaguc | uuagcaggu | agcuagucca | uacuagcccu | 240 |
| guuauauggc | guuuuggacu | agugaaguuc | aaguaauaua | acuaugaucg | uagaggucag | 300 |
| ugacgagaug | cguuuggaca | gggguucaac | uccc | | | 334 |

<210> SEQ ID NO 88
<211> LENGTH: 347
<212> TYPE: RNA
<213> ORGANISM: Aquifex aeolicus

<400> SEQUENCE: 88

| | | | | | |
|---|---|---|---|---|---|
| gggggcggaa | aggauucgac | gggacaggc | gguccccgag | gagcaggccg | ggguggcuccc | 60 |
| guaacagccg | cuaaacagc | ucccgaagcu | gaacucgcuc | ucgcugccua | auuaaacggc | 120 |
| agcgcguccc | cgguagguuu | gcgguggcc | uaccggaggg | cgucagagac | acccgcucgg | 180 |
| gcuacucggu | cgcacggggc | ugaguagcug | acaccuaacc | cgugcuaccc | ucggggagcu | 240 |
| ugcccguggg | cgacccgagg | ggaaauccug | aacacgggcu | aagccuguag | agccucggau | 300 |
| guggccgccg | uccucggacg | cgdgguucgau | ucccgccgcc | uccacca | | 347 |

<210> SEQ ID NO 89
<211> LENGTH: 355

```
<212> TYPE: RNA
<213> ORGANISM: Thermotoga maritima

<400> SEQUENCE: 89
gggggcgaac gguuucgacg gggauggagu ccccugggaa gcgagccgag gucccaccu      60 ccucguaaaa aaggugggac aaagaauaag ugccaacgaa ccuguugcug uugccgcuua    120
auagauaagc ggccguccuc uccgaaguug gcugggcuuc ggaagagggc gugagagauc    180
cagccuaccg auucaguucg ccuuccggcc ugaaucggga aaacucagga aggcugcuggg  240 agaggacacc cugcccgugg gaguccccuc ccgagagcga aaacacggcc ugcgcucgga    300
gaagcccagg ggccuccauc uucggacggg gguucgaauc ccccgccuc cacca          355

<210> SEQ ID NO 90
<211> LENGTH: 355
<212> TYPE: RNA
<213> ORGANISM: Thermotoga neapolitana

<400> SEQUENCE: 90
gggggcggaa aggauucgac ggggauggag uccccuggga agcgagccga ggucccacc      60 uccucguaaa aaggugggga acacgaauaa gugccaacga accguuugcu guugccgccu    120
aauagauagg cggccguccu cuccggaguu ggcugggcuc cggaagaggg cgugagggau    180
ccagccuacc gaucugggcu ccgccuuccg gcccggaucg ggaaguucca ggaaggcugu    240
gggaagcgac acccugcccg ugggggguuc uucccgagac acgaaacacg ggcugcgcuc    300
ggagaagccc aggggccucc aucuucggac ggggguucga uucccgccgc cucca          355

<210> SEQ ID NO 91
<211> LENGTH: 350
<212> TYPE: RNA
<213> ORGANISM: Thermus thermophilus

<400> SEQUENCE: 91 ggggugaaa cggucucgac gggggucgcc gagggcgugg cugcgcgccg aggugcgggu      60
ggccucguaa aaacccgcaa cggcauaacu gccaacacca acuacgcucu cgcggcuuaa    120
ugaccgcgac cucgcccggu agcccugccg ggggcucacc ggaagcgggg acacaaaccc    180
ggcuagcccg gggccacgcc cucuaaccccc ggcgaagcu ugaagggggc ucgcuccugg    240 ccgcccguccc gcgggccaag ccaggaggac acgcgaaacg cggacuacgc gcguagaggc    300
cacgccccgg cgaccuucgg acggggguuc gauuccccccc accuccacca                350

<210> SEQ ID NO 92
<211> LENGTH: 349
<212> TYPE: RNA
<213> ORGANISM: Deinococcus radiodurans

<400> SEQUENCE: 92
gggggugacc cgguuucgac aggggaacug aaggugaugu ugcgugucga ggugccguug      60
gccucguaaa caaacggcaa agccauuuaa cuggcaacca gaacuacgcu ucgcugcuu      120 aagugagaug acgaccgugc agcccggccu uuggcgucgc ggaagucacu aaaaaagaag    180
gcuagcccag gcgauucccc auagccgacg gcgaaacuuu auggagcuac ggccugcgag    240
aaccugccca cugcugagcg ccggcccgac aaucaaacag ugggauacac acguagacgc    300
acgcuggacg gaccuuugga cggcgguucg acuccgccca ccuccacca                349

<210> SEQ ID NO 93
```

<211> LENGTH: 347
<212> TYPE: RNA
<213> ORGANISM: Deinococcus proteolyticus

<400> SEQUENCE: 93

```
gggggcggaa aggauucgac gggggaacgg aaagcgcugc ugcgugccga ggagccguug      60
gccucguaaa caaacggcaa agccauuaac uggcgaaaau aacuacgcuc ucgcugcuua     120
agugagagca gugaccacgu agccccgccu uuggcgacgu gugaacugag acaaaagaag    180
gcuagcuuag gugagguucc auagccaaaa gugaaaccaa auggaaauaa ggcggacggc    240
agccuguuug cuggcagccc aggcccgaca auuuaagagc agacuacgca cguagaugca    300
cgcuggaugg accuuuggac ggcgguucga uucccgccgc cucacca                  347
```

<210> SEQ ID NO 94
<211> LENGTH: 334
<212> TYPE: RNA
<213> ORGANISM: Thermomicrobium roseum

<400> SEQUENCE: 94

```
cagggccgua ggugcgagga uugcaggucg aggucgccca cgaacucgua aaaggggca      60
ccaaguaacu ggcgagcgcg aacucgcucu ggcugcguaa uucacgcagc cacgucugcc    120
cggacccuuc ccuggugggu ucggagcggg cgccgcaaga ccggggugcc ccuggcccaa    180
gcgccggugc gggccagguc aagcgugauc cggcucggcu gaccgggauc cugucggugg    240
gagccuggca gcgacaguag aacaccgacu aagccguuag cauauccucg gcugaacgcu    300
cuggacgggg guucaacucc cgccagcucc acca                                334
```

<210> SEQ ID NO 95
<211> LENGTH: 353
<212> TYPE: RNA
<213> ORGANISM: Coprothermobacter proteolyticus

<400> SEQUENCE: 95

```
gggggcggaa aggauucgac ggggagucgg agccuugagc ugcaggcagg guuggcugcc      60
acaccuuaaa aagguagca aggcaaaaau aaaugccgaa ccagaauuug cacuagcugc     120
uuaauguaag cagccgcucu ccaaacugag gcugcauaag uuuggaagag cgucaaccca    180
ugcagcggcu cuuaagcagu ggcaccagcu guuuaagggu gaaaagagug gugcugggca    240
gugcgguugg gcuuccuggg cugcacuguc gagacuucac aggagggcua agccuguaga    300
cgcgaaaggu ggcggucugu cggacgcggg uucgauuccc gccgccucca cca            353
```

<210> SEQ ID NO 96
<211> LENGTH: 360
<212> TYPE: RNA
<213> ORGANISM: Herpetosiphon aurantiacus

<400> SEQUENCE: 96

```
gggggcggaa aggauucgac gggagggcc aaucguaagu ggcaagccga gacgcugagc      60
cucguuaaau cggcaacgcc auuaacuggc aaaaacacuu uccgcgcucc uguagcgcuu    120
gcugccuaau uaaggcaaca cgucucuacu agccucagcc cgaugggcuu guagcggcga    180
cacuuagucg ggucgcuccc cuaguuaugu cuguggggcua ggggcuaaga uuaacaggcu    240
ggucguggcc cgcuuugucu aucggguggu gcaccgauaa gauuuaauca auagacuacg    300
cuuguagaug cuugcgguuu aacuuuuugg acgcggguuc gauucccgcc gccuccacca    360
```

<210> SEQ ID NO 97
<211> LENGTH: 355
<212> TYPE: RNA
<213> ORGANISM: Thermodesulfobacterium commune

<400> SEQUENCE: 97

| | | | | | | |
|---|---|---|---|---|---|---|
| gggggcggaa | aggauucgac | ggggauaggu | aggauuaaac | agcaggccgu | ggucgcaccc | 60 |
| aaccacguua | aauagggugc | aaaaacacaa | cugccaacga | auacgccuac | gcuuuggcag | 120 |
| ccuaagcgug | cugccacgca | ccuuuagacc | uugccugugg | gucuaaaggu | gugugaccua | 180 |
| acaggcuuug | ggaggcuuaa | ucggugggu | uaagccuccc | gagauuacau | cccaccuggu | 240 |
| aggguugcuu | ggugccugug | acaagcaccc | uacgagauuu | ucccacaggc | uaagccugua | 300 |
| gcgguuuaau | cugaacuauc | uccggacgcg | gguucgauuc | ccgccgccuc | cacca | 355 |

<210> SEQ ID NO 98
<211> LENGTH: 329
<212> TYPE: RNA
<213> ORGANISM: Verrucomicrobium spinosum
<220> FEATURE:
<221> NAME/KEY: misc_feature
<222> LOCATION: (1)..(329)
<223> OTHER INFORMATION: n is an unknown base

<400> SEQUENCE: 98

| | | | | | | |
|---|---|---|---|---|---|---|
| gggnnnnauu | uggaauucgc | cgaaugcuag | aaguggaggc | ugcaugccgc | ggaugauucg | 60 |
| uuggccgcuu | uaccaauucg | gaucaaacaa | cuaaaugcgg | acucuaacga | gcuugcccuc | 120 |
| gccgcuuaau | ugacggugac | guuccuccag | ugaagucugu | gaauuggagg | agcgacuacu | 180 |
| uacaggcugg | ccaaaagagc | gggcgaccgg | ccccaaggcg | agaucuacag | gccgcuggau | 240 |
| ggacggcauc | cuggcaguag | gaggcuggac | aucgagauca | aaunauugcc | ugagcaugga | 300 |
| gacgcuuuca | uaaaggnguu | cggacaggg | | | | 329 |

<210> SEQ ID NO 99
<211> LENGTH: 351
<212> TYPE: RNA
<213> ORGANISM: Dictyoglomus thermophilum

<400> SEQUENCE: 99

| | | | | | | |
|---|---|---|---|---|---|---|
| gggggcggaa | aggauucgac | ggggaguaca | aggaucaaaa | gcugcaagcc | gaggugccgu | 60 |
| uaccucguaa | aacaacggca | aaaaagaagu | gccaacacaa | auuuagcauu | agcugcuuaa | 120 |
| uuuagcagcu | acgcucuucu | aacccgggcu | ggcaggguua | aagggguguc | auaaugagcc | 180 |
| agcugccccu | uccgacuccc | cuaaggaagg | gaaagaugua | ggggauaggu | gcuuacagaa | 240 |
| uccugcggga | gggagucugu | aagugccgaa | aaguuaaaac | ucccgcuaag | cuuguagagg | 300 |
| cuuuugauuc | uugcucucug | gacgcggguu | cgauucccgc | cgccuccacc | a | 351 |

<210> SEQ ID NO 100
<211> LENGTH: 399
<212> TYPE: RNA
<213> ORGANISM: Synechocystis sp. PCC 6803

<400> SEQUENCE: 100

| | | | | | | |
|---|---|---|---|---|---|---|
| ggggccgcaa | ugguuucgac | agguuggcga | aagcuugccc | gugauacagg | ucgagaguga | 60 |
| gucuccucuc | gcaaaucaaa | ggcucaaaaa | aaaguaacug | cgaauaacau | cgucagcuuc | 120 |
| aaacggguag | ccauagcagc | cuagucugua | aaagcuacau | uuucuuguca | agaccguuu | 180 |
| acuucuuuuc | ugacuccguu | aaggauuaga | gguuaacccc | aacggaugcu | uuguuuggcu | 240 |

```
cuucucuagu uagcuaaaca aucaagacuc agacuagagc aucccaccau cagggauaau      300
cgaugguccc cguccuaggg cuagaaggac uaaaccugug aaugagcgga aaguuaauac      360
ccaguuugga cagcaguuca auucugcucg gcuccacca                            399
```

<210> SEQ ID NO 101
<211> LENGTH: 385
<212> TYPE: RNA
<213> ORGANISM: Nostoc muscorum

<400> SEQUENCE: 101

```
ggguccgucg guuucgacag guuggcgaac gcuacucugu gauucagguc gagagugagu       60
cuccucugca aaucaaggcu caaaacaaaa guaaaugcga auaacaucgu uaaauuugcu      120
cguaaggacg cucuaguagc ugccuaaaua gccucuuuca gguucgagcg ucuucgguuu      180
gacuccguua aggacugaag accaaccccc aacggaugcu cuagcaaugu ucucugguug      240
gcuugcuagc uaagauuuaa ucagagcauc uacguucgg gauaaugaac gauucccgcc      300
uugaggguca gaaaggcuaa accugugaau gagcgggggg ucaauaccca auuggacag      360 caguucgacu cugcucgauc cacca                                           385
```

<210> SEQ ID NO 102
<211> LENGTH: 393
<212> TYPE: RNA
<213> ORGANISM: Synechococcus PCC 6301

<400> SEQUENCE: 102

```
ggggcuguaa ugguuucgac guguugguga auccuucacc ugauucagg ccgagaggga       60 guccacucuc guaauccag gcucaaccaa aaguaacugc gaacaacauc guuccuuucg      120
cucguaaggc ugcuccugua gcugcuuaaa cgccacaaac uuucuggcuc gagcgucuag      180
ucguagacuc cguuaauacg ccuagacuua accccaac ggaugcugag uggcggccuc       240
agguccgucc ucucgcuaag caaaaaccug agcaucccgc caacggggau aaucguuggc      300
ucccgcacag ugggucaacc ugucuaagcc ugugaacgag cggaaaguua cuagucaaug      360
cggacagcgg uucgauuccg cucagcucca cca                                  393
```

<210> SEQ ID NO 103
<211> LENGTH: 312
<212> TYPE: RNA
<213> ORGANISM: Leptolyngbya sp. (ATCC 27894)

<400> SEQUENCE: 103

```
ggcucaaaaa aauagaugca aacaacaucg uaccuuucgc ucguaaaacu gcaccuguug       60
cagcauaaaa caccucuaau ucagguucga gcgcuuaccg ucugacaccg uuaaagauag      120
uaagcacaac cccaacgguu gcucuagaau uucgccuuug gucggcauuc uagcuaagac      180
aauaccaaag cauccuauug uccgggacaa aggacaguuc ccgcuucgag gauuagagaa      240
gcuaaaccug ugaaugauug auagagcuaa uacccaguuu ggacacgggu ucaacucccg      300
ccagcuccac ca                                                         312
```

<210> SEQ ID NO 104
<211> LENGTH: 323
<212> TYPE: RNA
<213> ORGANISM: Porphyra purpurea

<400> SEQUENCE: 104

```
ggggcugcaa gguuucuaca uugugaaaaa acaaauauau gaaaguaaaa cgagcucauu       60
```

```
atuagagcuu uuaguuaaau aaaugcagaa aauaauauua uugcuuuuuc ucgaaaauua      120
gcuguugcau aaauagucuc aauuuuugua auucgaagug auagacucuu auacacuacg      180
aauauucugu uagaguugcu cuuaauaaaa gaaaaguaaa aaaauacaaa uucuuauguu      240
uuuuaccuga auugauucaa uuuaagguua guauuuuug auuuuuacaa uggacguggg       300
uucaagcccc accagcucca cca                                              323
```

```
<210> SEQ ID NO 105
<211> LENGTH: 294
<212> TYPE: RNA
<213> ORGANISM: Cyanophora paradoxa

<400> SEQUENCE: 105
```

```
ggggcuguuu agguuucgac guuuuuucu aauuauguuu guuaagcaag ucgaggauuu       60
guucuaucuc gaaaucaag aacucucaaa auuuaaacgc aacuaauauu guacguuuua      120
accguaaagc agcuuucgcu guuuaauaau uacuuuaau uuaaaaaccu aauuuuuuua     180
ggaauuuauu uauuuauugu uuauccugcu uaaugaauua aaaaaagcua acuugugaa      240 uaaacgcaua auuuaaaaaa acggacgugg guucaaauuc caccagcucc acca           294
```

```
<210> SEQ ID NO 106
<211> LENGTH: 371
<212> TYPE: RNA
<213> ORGANISM: Odontella sinensis

<400> SEQUENCE: 106
```

```
ggggcugacu ugguuucgac auuuaaaaau uguuacagua ugaugcaggu cgaaguuucu      60
aaucuucgua aaaaaagaga aauuuauaau aaaugcuaau aauuuaauuu cuucugugut     120
uaaaaguuua ucaacuaagc aaaauaguuu aaauuuaagu uugcuguuu aguuuuuaug     180 cacauuuaau gaucuaguaa auaacuuugu ucgcuauaau uuauauuuau aacuagacuu     240
uugucuuuuu uauaguuuag aauaacuuua ucauuucaaa ccucguucca ucuaguugaa     300
cuaaaccugu gaacgaauac auaauaaaaa uuuuuagaug gacgugggguu cgacucccau     360 cagcuccacc a                                                          371
```

```
<210> SEQ ID NO 107
<211> LENGTH: 348
<212> TYPE: RNA
<213> ORGANISM: Thls. weiss*

<400> SEQUENCE: 107
```

```
ggggcugauu ugguuucgac auuuaaaacu ucuuucuaug ugucagguca aaguuuguau      60
ucuuuguaaa aaaauacuaa aauacuaaua aaugcuaaua auauaauacc guuuauuuuu     120
aaagcaguaa aaacaaaaaa agaagcaaug gcuuuaaauu uugcuguaua guucauuaac     180
uuagguuauu aaauauuuuu ucauuauaac uggacuuuuu cucaguuuau aguuuagaau     240
aaauuuaaau uuugcaaaac ucguucgaaa auuuucgggc uaaaccugua aacgcaaaua     300
cuaagaaauu uuagauggac augguuucaa uucccaucag uuccacca                  348
```

```
<210> SEQ ID NO 108
<211> LENGTH: 330
<212> TYPE: RNA
<213> ORGANISM: Guillardia theta

<400> SEQUENCE: 108
```

```
gggcugauu uggauucgac auauaaauuu gcguguuuca uuaugaagca agucaaguuu      60
aaugaucuug uaaaaaacau uaaaguacaa auaaaugcaa gcaauauagu ucauuuagu    120 ucaaaacguu uagucucuuu ugcauaagca aaaugguuua auaacuuucu aguagaaau    180 uggagaaguu uacuaagauu uauauuuacu ccauaauuau uuuaaagaug guaaaaaggu   240
gauucaucau uuguauguuu cuaaacuuug ugaaagaaua gugggcucca uuuauaauga   300
acguggguuc aaaucccacc agcuccacca                                    330
```

```
<210> SEQ ID NO 109
<211> LENGTH: 353
<212> TYPE: RNA
<213> ORGANISM: Mycoplasma hyorhinis

<400> SEQUENCE: 109
cauacauaaa aggauauaaa uugcaguggu cuuguaaacc auaagacaau uucuuuacua    60
agcggaaaag aaaacaaaaa agaagauuau ucauuauuau ugaaugcuuc aacucaauca   120
aaucuagcuu uugcauuuua aaaaacuagu agaccaauuu gcuucacacg aauuguaauc   180
uuuauauuag agaauaguua aaaaucugau cacuuuuuaa ugaauuuaua gaucacaggc   240
uuuuuuaauc uuuuuguuau uuuagauaaa gagucuucuu aaaaauaacu aaacuguagg   300
aauuuauauu uaauuaugcg uggacccggg uucaacuccc gccagcucca cca          353
```

```
<210> SEQ ID NO 110
<211> LENGTH: 411
<212> TYPE: RNA
<213> ORGANISM: Mycoplasma capricolum

<400> SEQUENCE: 110 gggauguca uggauuugac aggauaucuu uaguacauau aagcaguagu guuguagacu    60
auaaauacua cuagguuuaa aaaaacgcaa auaaaaacga agaaacuuuu gaaaugccag   120
cauuuaugau gaauaaugca ucagcuggag caaacuuuau guuugcuuaa uaacuacuag   180
uuuaguuaua guauuucacg aauuauagau auuuuaagcu uuauuuauaa ccguauuacc   240
caagcuuaau agaauauaug auugcaauaa auauauuuga aaucuaauug caaaugauau   300
uuaaccuuua guuaauuuua guuaaauauu uaauuagaa aauuaacuaa acuguagaaa    360
guauguauua auauaucuug gacgcgaguu cgauucucgc caucuccacc a            411
```

```
<210> SEQ ID NO 111
<211> LENGTH: 381
<212> TYPE: RNA
<213> ORGANISM: Mycoplasma pirum

<400> SEQUENCE: 111
caugaaugau ggacccauag aggcaguggg guaugcuccu uauagcucaa gguuuaaauu    60
aaccgacaaa acugacgaaa acguugccgu ugauacaaau uuauuaauca accaacaagc   120
ucaauuuaac uacgcauuug cauaguauaa aaaauaaau ugugcuacuc auuguaauua    180
gguuacuaaa uuacuuuguu uuauauaguc cuguaacuag uucuagugau gucuauaaac   240
uagaaugaga uuuauagacu uauuuguugg cgguugugcc auagccuaaa ucaacaaaga   300
caauuuauuu augguacuaa acuagagauu cuaugaugaa auuauuugug gaaacggguu   360
cgauucccgc caucuccacc a                                              381
```

```
<210> SEQ ID NO 112
<211> LENGTH: 387
```

-continued

```
<212> TYPE: RNA
<213> ORGANISM: Mycoplasma pneumoniae

<400> SEQUENCE: 112
ggggauguag agguuuugac auaauguuga aaggaaaaca guugcagugg gguaugcccc      60
uuacagcucu agguauaaua accgacaaaa auaacgacga aguuuggua gauccaaugu     120 ugaucgcuaa ccaacaagca aguaucaacu acgcuuucgc uuagaacaua cuaaagcuac    180
acgaauugaa ucgccauagu uugguucgug ucacaguuua uggcucgggg uuaacugguu    240
caacuuaauc cuuaaauuau gaacuuaucg uuuacuuguu ugucuuauga ucuaaaguaa    300
gcgagacauu aaaacauaag acuaaacugu agaagcuguu uuaccaaucc uuuauggaaa    360
cggguucgau ucccgucauc uccacca                                         387

<210> SEQ ID NO 113
<211> LENGTH: 388
<212> TYPE: RNA
<213> ORGANISM: Mycoplasma genitalium

<400> SEQUENCE: 113
ggggauguuu uggguuugac auaaugcuga uagacaaaca guagcauugg gguaugcccc      60
uuacagcgcu agguucaaua accgacaaag aaaauaacga aguguuggua gauccaaauu    120
ugaucauuaa ccaacaagca aguguuaacu uugcuuuugc auaaguagau acuaaagcua    180
cagcugguga auagcauag uuugcuagcu gucauaguuu augacucgag guuaaaucgu    240
ucaauuuaac cuuaaaaaau agaacuuguu guuuccauga uuguuuugug aucauuggau    300
aacaagacaa aaauccacaa aacuaaaaug uagaagcugu uuguugugc cuuuauggaa    360 acggguucga uucccgucau cuccacca                                        388

<210> SEQ ID NO 114
<211> LENGTH: 412
<212> TYPE: RNA
<213> ORGANISM: Ureaplasma urealyticum

<400> SEQUENCE: 114
ggggauguca cgguuucgac gugacacauu aauuuuuaau ugcagugggg uuagcccuu       60 aucgcuuucg aggcauuuua aaugcagaaa auaaaaaauc uucugaagua gaauuaaacc    120
cagcguuuau ggcuucagcu acuaaugcaa acuacgcuuu ugcguacuaa uuaguuauua    180
guagaaacgu ucauuaacau aauuacuauu gguugguuu ugggcuuauu uuacaauagu    240
uuuaaauuua aaauucuuau uguuguuaa auuuaaauag auuuaacaaa uaguuaguua    300 auuuaaauu uguuuuauua guauuaaacu acacuauuuu uaauaaaacu aaacuguaga    360
uauuauuaau uaugguguugc ggaaaggggu ucgauucccc ucaucuccac ca           412

<210> SEQ ID NO 115
<211> LENGTH: 365
<212> TYPE: RNA
<213> ORGANISM: Mycoplasma salivarium

<400> SEQUENCE: 115
caggcauucg auucauuaug uugcaguggu uugcaaacca uaaggcacua ggcuuuuuua      60
aacgcaaaag accaaaaaac agaagaucaa gcaguugauc uagcauuuau gaauaauuca    120
caaaugcaau caaacucuagu uuucgcuuag uaaaauuagu caauuauua uggugcucaa    180 cauaauaaau gguaguauga gcuuaauauc auaugauuuu aguuaauaug auaggauuug    240
```

| | |
|---|---|
| uacuaaacu auguuauaga aauuuguaaa uuauauauau gacauaggaa auuuaauuua | 300 |
| cuaaacugua gaugcauaau guugaagaug uguggaccgg gguucaacuc ccgccagcuc | 360 |
| cacca | 365 |

<210> SEQ ID NO 116
<211> LENGTH: 363
<212> TYPE: RNA
<213> ORGANISM: Clostridium innocuum

<400> SEQUENCE: 116

| | |
|---|---|
| cggggauaug ucugguacag acugcagucg agugguuacg uaauaaccaa uuaaauuuaa | 60 |
| acggaaaaac uaaauuagcu aaccucuuug guggaaacca gagaauggcu uucgcugcuu | 120 |
| aauaaccgau auagguucgc agccgccucu gcaugcuucu uccuugacca uggaugug | 180 |
| cgcguaagac gcaagggaua aggaaucugg uuugccugag aucagauuca cgaaaauucu | 240 |
| ucaggcacau ucaucagcgg auguucauga ccugcugaug ucuuaaucuu caugacuaa | 300 |
| acuguagagg ucuguacgug gggcuguuuc uggacaggag uucgauuccc ccgccucca | 360 |
| cca | 363 |

<210> SEQ ID NO 117
<211> LENGTH: 359
<212> TYPE: RNA
<213> ORGANISM: Mycoplasma fermentans

<400> SEQUENCE: 117

| | |
|---|---|
| caugcauugg gugauacuaa uaucaguagu uggcagacu auaaugcauc uaggcuuuau | 60 |
| aaucgcagaa gauaaaaaag cagaagaagu uaauauuucu ucacuuauga uugcacaaaa | 120 |
| aaugcaauca caaucaaacc uugcuuucgc uuaguuaaaa gugacaagug guuuaaagu | 180 |
| ugacauuuuc cuauauauuu uaaaaucggu uuuuaaggag aacaggaguc ugaaagggu | 240 |
| ccaaaaaucu auauuguuug cauuucggua guauagauua auuagaaaug auaaacugua | 300 |
| aaaaguauug guauugacuu ggugugugga cucgggguuca acuccgcca gcuccacca | 359 |

<210> SEQ ID NO 118
<211> LENGTH: 320
<212> TYPE: RNA
<213> ORGANISM: Acidobacterium capsulatum

<400> SEQUENCE: 118

| | |
|---|---|
| cggggugac ucgcggcaaag aggcaugccg gggggugggc acccguaauc gcucgcaaaa | 60 |
| caauacuugc caacaacaau cuggcacucg cagcuuaauu aaauaaguug ccguccucug | 120 |
| aggcuucgcc uguggccga ggcaggacgu cauacagcag gcugguuccu ucggcugggu | 180 |
| cugggccgcg gggaugagau ccacggacua gcauucugcg uaucuguucg cuucuaagcg | 240 |
| cagagugcga aaccuaaagg aaugcgacug agcauggagu cucuuuucug acaccaauuu | 300 |
| cggacgcggg uucgauuccc | 320 |

<210> SEQ ID NO 119
<211> LENGTH: 319
<212> TYPE: RNA
<213> ORGANISM: Fusobacterium mortiferum

<400> SEQUENCE: 119

| | |
|---|---|
| cggguuaug agguuauagg uagcaugcca ggaugaccgc ugagagggu caacacaucg | 60 |
| uuuagaugga aacagaaauu acgcuuuagc ugcuuaauua gucagcucac cucugguuuc | 120 |

```
ucucuucugu aggagaaucc aaccgaggug uuaccaauau acagauuacc uuuagugauu    180
ucucuaagcu caaagggaca uuuuagagaa uagcuucagu uagcccuguc ugcgggagug    240
auuguugcga aauaaaauag uagacuaagc auuguagaag ccuauggcgc ugguaguuuc    300
ggacacgggu ucaacuccc                                                 319

<210> SEQ ID NO 120
<211> LENGTH: 329
<212> TYPE: RNA
<213> ORGANISM: Fibrobacter succinogenes

<400> SEQUENCE: 120
cagggUuacc gaaguguuag uugcaagucg aggucucaga cgagggcuac ucguuaaaaa    60
gucugaaaaa aaauaagugc ugacgaaaac uacgcacucg cugccuaauu aacggcaacg    120
ccgggccuca uuccgcuccc aucggggugu acguccggac gcaauauggg auagggaagu    180
gucaugccug ggggcaucuc ccgagauuuu cuaggcuggu caaacuccgc ccgaccuuc     240 uugggcgugg auaagacgag aucuuaaauu cgaagggaac acuuguagga acguacaugg    300
acgugauuuu ggacaggggu ucaacuccc                                      329

<210> SEQ ID NO 121
<211> LENGTH: 300
<212> TYPE: RNA
<213> ORGANISM: Artificial
<220> FEATURE:
<223> OTHER INFORMATION: isolated from rumenal fluid

<400> SEQUENCE: 121
acgcccuugu cucagacgag ggcacucguu aaaaagucug aaaagaauaa cugcagaacc    60
uguagcuaug gcugcuuaau uuaagggcaa cccuuggauc cgccuccauc ccgaaggggu    120
ggcauccgag ucgcaaaucg ggauaggaug gaucuuggca acgaggagua cauccgaaau    180
uugucgcugc uggcugaagc aucgccguuc ucuuugggc guggcaaggc aagauuaaau    240
ucagaggaua agcguguagu agcgagugag uagguguuuu uggacgcggg uucaaguccc    300

<210> SEQ ID NO 122
<211> LENGTH: 330
<212> TYPE: RNA
<213> ORGANISM: Pirellula staleyi

<400> SEQUENCE: 122
ccggauagcc ugaagcgaau acggcgugcc ugguugauc agauggccac guaaaaagcu     60
gaucacaaac uuaacugccg agagcaaucu cgcacuugcu gccuaacuaa acggaugcuu    120
ccgacugagg gcuuuagccg gagaggccca aaaguugguc accaaauccg gaccgccucg    180
ugccaugauc gaaacgcacg aggucaaaaa aguuucgauc uagugcaggg uguagccagc    240
agcuaggcga caaacugugc aaaaaaucaaa uuuucugcua cgcacguaga uguguucgug    300
aaaaugucuc gggacggggg uucaacuccc                                     330

<210> SEQ ID NO 123
<211> LENGTH: 329
<212> TYPE: RNA
<213> ORGANISM: Planctomyces maris

<400> SEQUENCE: 123
cugguucacc guauguuaag guggcggugc cguggUugau caguuggcca cguaaaaagc    60
```

```
ugaucacaau cuaauugcaa acaagcaauu uucaauggcu gcuuaauaaa agcaaccccg    120
gcuuaggaau cucugucuga ggaguccgac agcuggucac aaaaucagac ugguaucaga    180 ucaaugugccg cuccgucuga uacgagauuc guggguggacu gguuccaac aggcucuguu   240
```

```
ucaaugccg cuccgucuga uacgagauuc guggguggacu gguuccaac aggcucuguu     240 uaucgugccc gaagaaacga gacucaaacg auaaaauaug caccguagag gcuuuagcug    300
aggguucaca ggacgcgggu ucaacuccc                                      329
```

<210> SEQ ID NO 124
<211> LENGTH: 318
<212> TYPE: RNA
<213> ORGANISM: Artificial
<220> FEATURE:
<223> OTHER INFORMATION: isolated from sludge

<400> SEQUENCE: 124

```
cagggaacca ggagguguga gaugcaugcc ggagacgcug uccgcuccgu uaucaagcag    60
cacaacaaaa uaauugcaaa caacaauuac uccuuagcag cguaagcagc uaacguucaa    120
ccucuccgga ccgccgggag gggauuuggg cgucgaaaca gcgcggacgc uccggauagg    180
acgcccauaa uauccggcua agaccauggg ucuggcucuc gcggucuga uugucuucca    240 ccgcgcgggc cgcgaucaaa gacaacuaag cauguaggu cuugcauggc cuguucuuug    300
gacgcggguu cgauuccc                                                  318
```

<210> SEQ ID NO 125
<211> LENGTH: 407
<212> TYPE: RNA
<213> ORGANISM: Porphyromonas gingivalis

<400> SEQUENCE: 125

```
ggggcugacc ggcuuugaca gcgugaugaa gcgguaugua agcauguagu gcguggggugg   60 cuugcacuau aaucucagac aucaaaaguu uaaauuggcga aaauaacuac gcucucgcug   120
cguaaucgaa gaauaguaga uuagacgcuu caucgccgcc aaaguggcag cgacgagaca    180
ucgcccgagc agcuuuuucc cgaaguagcc cgauggugcg gugcugacaa aucgggaacc    240
gcuacaggau gcuuccugcc uguggucaga ucgaacggaa gauaaggauc gugcauuggg    300
ucguuucagc cuccgcucgc ucacgaaaau uccaacugaa acuaaacaug uagaaagcau    360
auugauucca uguuuggacg agguucaauu ccccuccagc uccacca                  407
```

<210> SEQ ID NO 126
<211> LENGTH: 379
<212> TYPE: RNA
<213> ORGANISM: Bacteroides thetaiotaomicron

<400> SEQUENCE: 126

```
cagcgggcag aaaugguagg uaagcaugca gugggucggu aauuccacu uaaaucucag     60 uuaucaaaac uuuaucuggc gaaacuaauu acgcucuugc ugcuuaaucg aaucacagua    120
gauuagcuua auccaggcac uaggugccca ggagagacau cacucggaag cguuugcucc    180
gaagcauucc gguucagugg ugcaguaaca ucggggauag ucagaagcgg ccucgcguuu    240
uugaugaaac uuuagaggau aaggcaggaa uugauggcuu gguucugcu ccugcacgaa     300 aauuuaggca agauaagca uguagaaagc uuaugauuuc cucguuugga cgagggucca    360
acucccgcca gcuccacca                                                 379
```

<210> SEQ ID NO 127
<211> LENGTH: 404

```
<212> TYPE: RNA
<213> ORGANISM: Chlorobium tepidum

<400> SEQUENCE: 127
ggggaugaca ggcuaucgac aggauaggug ugagaugucg uugcacuccg aguuucagca    60
uggacggacu cguuaaacaa gucuauguac caauagaugc agacgauuau ucguaugcaa   120
uggcugccug auuagcacaa guuaauucag aagccaucgu ccugcgguga augcgcuuac   180
ucugaagccg ccggauggca uaacccgcgc uugagccuac ggguucgcgc aaguaagcuc   240
cguacauuca ugcccgaggg ggugugcggg uaaccaaucg ggauaagggg acgaacgcug   300
cuggcggugu aaucggacca cgaaaaacca accaccagag augagugugg uaacugcauc   360 gagcagguc cuggacgcgg guucaagucc cgccaucucc acca                    404

<210> SEQ ID NO 128
<211> LENGTH: 372
<212> TYPE: RNA
<213> ORGANISM: Chlorobium limicola

<400> SEQUENCE: 128
caggauacgu gugagaugug guugcacucc gaguuucagc auggacggac ucguuaaaca    60
agucuaugua ccauuagaug cagacgauua uucguaugca auggcugccu gauuagcaca   120
aguuaacuca gacgccaucg uccugcggug aaugcgcuua cucugaagcc gccggauggc   180
auaacccgcg cuugagccua cggguucgcg caaguaagcu ccguacauuc augcccgagg   240
ggcugugcgg guaauuucuc gggauaaggg gacgaacgcu gcuggcggug uaaucggccc   300
acgaaaaccc aaucaccaga gaugagugug gugacugcau cgagcagugu uuggacgcg   360 gguucaacuc cc                                                       372

<210> SEQ ID NO 129
<211> LENGTH: 420
<212> TYPE: RNA
<213> ORGANISM: Chlamydia trachomatis

<400> SEQUENCE: 129
ggggguguaa agguuucgac uuagaaauga agcguuaauu gcaugcggag ggcguuggcu    60
ggccuccuaa aaagccgaca aaacaauaaa ugccgaaccu aaggcugaau gcgaaauuau   120
cagcuucgcu gaucucgaag aucuaagagu agcugcuuaa uuagcaaagu uguuaccuaa   180 auacgggguga cccggugucc gcgagcucca ccagagguuu cgaaacacc gucauguauc   240 ugguuuagaac uuaagguccuu uaauucucga ggaaaugagu uugaaauuua augagagucg   300
uuagucucua uaggggguuc uagcugagga gacauaacgu auaguaccua ggaacuaagc   360
auguagaggu uagcgggag uuuacuaagg acgagaguuc gacucucucc accuccacca   420

<210> SEQ ID NO 130
<211> LENGTH: 421
<212> TYPE: RNA
<213> ORGANISM: Chlamydia mousep*

<400> SEQUENCE: 130
ggggguguaa agguuucgac uuagaaauga agcguuaauu gcaugcggag ggcguuggcu    60
ggccuccuaa aaagccgaca aaacaauaaa ugccgaaccu aaggcugaau gcgaaauuau   120
cagcuucgcu gaucuuaaug aucuaagagu ugcugcuuaa uuagcaaagu uguuaccuaa   180
guacugguaa cccggugucc gcgagcucca ccagagguuu ucgaaacgcc gucauuuauc   240
```

| | |
|---|---|
| ugguuagaau uagggccuuu uaacucucaa gggaacuaau uugaauuuua augagagucg | 300 |
| uuggucucua uagagguuuc uagcugagga gauauaacgu aaaauauucu agaaacuaag | 360 |
| cauguagagg uuagcgggga guuuacuaag gacgagaguu cgaaucucuc caccuccacc | 420 |
| a | 421 |

<210> SEQ ID NO 131
<211> LENGTH: 426
<212> TYPE: RNA
<213> ORGANISM: Chlamydia pneumoniae

<400> SEQUENCE: 131

| | |
|---|---|
| gggggguguau agguuucgac uugaaaauga aguguuaauu gcaugcggag ggcguuggcu | 60 |
| ggccuccuaa aaagccaaca aaacaauaaa ugccgaaccu aaggcugaau gcgaaauuau | 120 |
| uagcuuguuu gacucaguag aggaaagacu agcugcuuaa uuagcaaaag uguuagcua | 180 |
| gauaaucucu agguaacccg guaucugcga gcuccaccag aggcuugcaa aauaccguca | 240 |
| uuuaucuggu uggaacuuac uuucucuaau ucucaaggaa guucguucga gauuuugag | 300 |
| agucauuggc ugcuauagag gcuuucuagcu aagggagucc aauguaaaca auucuagaag | 360 |
| auaagcaugu agagguuagc agggaguuug ucaaggacga gaguucgagu cucuccaccu | 420 |
| ccacca | 426 |

<210> SEQ ID NO 132
<211> LENGTH: 328
<212> TYPE: RNA
<213> ORGANISM: Micrococcus luteus

<400> SEQUENCE: 132

| | |
|---|---|
| cggugugugu cgcgucggga aagcgggcc gaggaugcag agucaucucg ucaaacgcuc | 60 |
| ucugcaaacc aauaagugcc gaauccaagc gcacugacuu cgcucucgcu gccugaucag | 120 |
| ugaucgaguc cgucacccccg aggucgcugu cgccucggau cguggcguca gcuagauagc | 180 |
| cacugggcgu caccucgcc ggggucgug acgccgacau caauccggcu ggguccgggu | 240 |
| uggccgcccg ucugcgggac ggccaggacc gagcaacacc cacagcagac ugcgcccgga | 300 |
| gaagaccugg caacaccuca ucggacgc | 328 |

<210> SEQ ID NO 133
<211> LENGTH: 368
<212> TYPE: RNA
<213> ORGANISM: Mycobacterium leprae

<400> SEQUENCE: 133

| | |
|---|---|
| ggggcugaaa gguuucgacu ucgcgcaucg aaucaaggga agcgugccgg ugcaggcaag | 60 |
| agaccaccgu aagcgucguu gcagcaauau aagcgccgau ucauaugagc gcgacuaugc | 120 |
| ucucgcugcc uaagcgaugg cuagucuguc agaccggaaa cgcccucguc ccggagccug | 180 |
| gcaucagcua gagggaucua ccgaugggu cggucgcggg acucgucggg acaccaaccg | 240 |
| cgacuggggau cgucauccug gcuaguucgc gugaucagga gauccgagua gaggcauagc | 300 |
| gaacuacgca cggagaagcc uugagggaaa ugccguagga cccgggguucg auucccggca | 360 |
| gcuccacc | 368 |

<210> SEQ ID NO 134
<211> LENGTH: 360
<212> TYPE: RNA
<213> ORGANISM: Mycobacterium tuberculosis

<400> SEQUENCE: 134

| | |
|---|---|
| ggggcugaac gguuucgacu ucgcgcaucg aaucaaggga agcgugccgg ugcaggcaag | 60 |
| agaccaccgu aagcgucguu gcgaccaaau aagcgccgau ucacaucagc gcgacuacgc | 120 |
| ucucgcugcc uaagcgacgg cuagucuguc agaccgggaa cgcccucggc ccggacccug | 180 |
| gcaucagcua ccaccgauga guccggucgc gggacuccuc gggacaacca cagcgacugg | 240 |
| gaucgucauc ucggcuaguu cgcgugaccg ggagauccga gcagaggcau agcgaacugc | 300 |
| gcacggagaa gccuugaggg aaugccguag acccggguu cgauucccgg cagcuccacc | 360 |

<210> SEQ ID NO 135
<211> LENGTH: 373
<212> TYPE: RNA
<213> ORGANISM: Mycobacterium avium

<400> SEQUENCE: 135

| | |
|---|---|
| ggggcugaaa gguuucgacu ucgcgcaucg aaucaaggga agcgugccgg ugcaggcaac | 60 |
| ugaccaccgu aagcgucguu gcagauagau aagcgccgau ucacaucagc gcgacuacgc | 120 |
| ucucgcugcc uaagcgacag cuagucgagg gaucgucagc ccgggaacgc ccucgacccg | 180 |
| gagccuggcg ucagcuagag ggauccaccg augaguucgg ucgcgggacu caucgggaca | 240 |
| ccaacagcga cugggaucgu cauccuggcu uguucgcgug accaggagau ccgaguagag | 300 |
| gcauagcgaa cugcgcacgg agaagccuug agggaaugcc guaggacccg gguucgauuc | 360 |
| ccggcagcuc cac | 373 |

<210> SEQ ID NO 136
<211> LENGTH: 331
<212> TYPE: RNA
<213> ORGANISM: Corynebacterium xerosis

<400> SEQUENCE: 136

| | |
|---|---|
| cuucguacau ugagccaggg gaagcgugcc ggugaaggcu ggagaccacc gcaagcgucg | 60 |
| cagcaaccaa uuaagcgccg agaacucuca gcgcgacuac gcccucgcug ccuaagcagc | 120 |
| gaccgcgugu cugucagacc ggguaggccu cugauccgga cccuggcauc guuuaguggg | 180 |
| gcucgcucgc cgacuugguc gcaagggucg gcggggacac ucacuugcga cugggcccgu | 240 |
| cauccgguca uguucgacug aaccggaggg ccgagcagag accacgcgcg aacugcgcac | 300 |
| ggagaagccc uggcgaggug acggaggacc c | 331 |

<210> SEQ ID NO 137
<211> LENGTH: 354
<212> TYPE: RNA
<213> ORGANISM: Treponema pallidum

<400> SEQUENCE: 137

| | |
|---|---|
| ggggaugacu agguuucgac uagggaugug ggguguugcg cugcaggugg agugucgauc | 60 |
| uccugauucg gcgccuuuau aacugccaau ucgacaguu ucgacuacgc gcucgccgcg | 120 |
| uaaucgcggg ccuguguuug cgcugcucug agcgaacaua ucgcccgac gccaaacgga | 180 |
| gcuugcucuu acguugugca cggcggacgu aggggacuu uugucugugc uaagacucug | 240 |
| gcgcgugcgg ugcaggccua gcagaguccg acaaacgcag uacgcaccgc uaaaccugua | 300 |
| ggcgcgcagc acucgcucuu uaggacgggg guucgauucc ccccaucucc acca | 354 |

<210> SEQ ID NO 138

```
<211> LENGTH: 362
<212> TYPE: RNA
<213> ORGANISM: Borrelia burgdorferi

<400> SEQUENCE: 138
ggggauguuu uggauuugac ugaaaauguu aauauuguaa guugcaggca gagggaaucu      60
cuuaaaacuu cuaaaauaaa ugcaaaaaau aauaacuuua caagcucaaa ucuuguaaug     120
gcugcuuaag uuagcagagg guuuguuga auuuggcuuu gagguucacu uauacucuuu     180
ucgacaucaa agcuugcuua aaaauguuuu caaguugauu uuuagggacu uuuauacuug     240
agagcaauuu ggugguuugc uaguauuucc aaaccauauu gcuuaauaaa auacuagaua     300
agcuuguaga agcuuauagu auuauuuuua ggacgcgggu ucaauucccg ccaucuccac     360
ca                                                                    362

<210> SEQ ID NO 139
<211> LENGTH: 364
<212> TYPE: RNA
<213> ORGANISM: Borrelia garinii

<400> SEQUENCE: 139
ggggcugauu cuggauucga cugaaaaugc gaauauugua aguugcaggc agagggaauc      60
ucuuaaaacu ucuaaaauaa augcaaaaaa uaauaacuuu acaagcucaa accuuguaau     120
ggcugcuuaa guuagcaggg aguuucguug aauuggcuuu gagguucacu uauacucuuu     180
uucgauaucg aagcuugcuu aaaaauguuu ucaaguuaau uuuuagggac uuuuguacuu     240
gagagcaauu uggcgguuug cuaguauuuc caaaccauau ugcuuaagua aaaugcuaga     300
uaagcuugua gaagcuuaua auauuguuuu uaggacgcgg guucaauucc cgccaucucc     360
acca                                                                  364

<210> SEQ ID NO 140
<211> LENGTH: 363
<212> TYPE: RNA
<213> ORGANISM: Borrelia afzelii

<400> SEQUENCE: 140
ggggcugauu cuggauucga cugaaaaugc uaauauugua aguugcaagc agagggaauc      60
ucuuaaaacu ucuaaaauaa augcaaaaaa uaauaacuuu acaaguucaa accuuguaau     120
ggcugcuuaa guuagcagag aguuuuguug aauuggcuuu gagauucacu uauacucuuu     180
uuagacaucg aagcuugcuu aaaaauguuu ucaaguugau uuuuagggac uuuuauacuu     240
gagagcaauu uggcgguuug cuaguauuuc caaaccauau ugcuuaguaa aauacuagau     300
aagcuuguag aagcuuauag uauuguuuuu aggacgcggg uucaauuccc gccaucucca     360
cca                                                                   363

<210> SEQ ID NO 141
<211> LENGTH: 363
<212> TYPE: RNA
<213> ORGANISM: Borrelia crocidurae

<400> SEQUENCE: 141
ggggcugauu cuggauucga cuaagaacuu uaguagcaua aauggcaagc agagugaauc      60
ucuuaaaacu ucuuuaauaa augcaaaaaa uaauaacuuu acaaguucag aucuuguaau     120
ggcugcuuaa uuuagcagag aguuuuguug gauuugcuuu gagguucaa cuuauacucu     180 uuuagacauc aaaguaugcc uaaaaauguu ucaaguugau uuuuagggac cuuuaaacuu     240
```

```
gagaguaauu uggugguuug cuuguuuucc aagccuuauu gcuuuuucua aaaauuagcu      300
aagcuuguag auauuuauga uauuauuuuu uggacgcggg uucaauuccc gccaucucca      360
cca                                                                   363
```

```
<210> SEQ ID NO 142
<211> LENGTH: 365
<212> TYPE: RNA
<213> ORGANISM: Borrelia hermsii

<400> SEQUENCE: 142
ggggcugauu cuggauucga cuaaaaacuu uaguagcaua aauugcaagc agagggaauc      60
ucuuaaaacu ucuuuaauaa augcaagaaa uaauaacuuu acaaguucaa aucuuguaau     120
ggcugcuuaa auuagcagag aguucugcug gauuuugcuu ugagguucag cuuauacucu     180
uuuaagacau caaagcuugc uuaaaaauau uucaaguuga uuuuuaggga cuuuuaaauu     240
ugagaguaau uuggcgguuu gcuaguuuuu ccaaaccuua uuacuuaaag aaaacacuag     300
cuaagcuugu agauauuuau gauauuauuu uuaggacgcg gguucaauuc ccgccaucuc     360
cacca                                                                 365
```

```
<210> SEQ ID NO 143
<211> LENGTH: 330
<212> TYPE: RNA
<213> ORGANISM: Alcaligenes faecalis

<400> SEQUENCE: 143
cgggggucaa gaagcagcac agggcguguc gagcaccagu acgcucguaa auccacugga      60
aaacuauaaa cgccaacgac gagcguuucg cucuagccgc uuaaggcugg gccacugcac     120
uaauuugucu uuggguuuagg uaggcaacc uacagcagug uuauuuacaa agaaucgaau     180
cggucugcgc cacgaaguce gguucuaaaa cuuaggugau egecaaggaa aggeeuguca     240 auuggcauag uccaagguua aaacuuaaaa uuaauugacu acacauguag aacugucugu     300
ggacggcuug cggacggggg uucgauuccc                                      330
```

```
<210> SEQ ID NO 144
<211> LENGTH: 340
<212> TYPE: RNA
<213> ORGANISM: Alcaligenes eutrophus

<400> SEQUENCE: 144
cguggguuac aaagcagugg agggcauacc gaggacccgu caccucguua aucaauggga      60
augcaauaac ugcuaacgac gaacguuacg cacuggccgc uuaauugcgg ccguccucgc     120
acuggcucgc ugacgggcua gggucgcaag accacgcgag gucauuuacg ucagauaagc     180
uccggaaggg ucacgaagcc gggacgaaa accuagugac ucgccgucgu agagcguguu     240
cguccgcgau gcgccgguua aaucaaauga cagaacuaag uauguagaac ucucugggaa     300
gggcuuacgg acgcgggguc gauucccgcc ggcuccacca                           340
```

```
<210> SEQ ID NO 145
<211> LENGTH: 326
<212> TYPE: RNA
<213> ORGANISM: Ralstonia pickettii

<400> SEQUENCE: 145 cgggggguugc gaagcagcgg agggcauacc gaggacccgu caccucguua aucaauggga     60
```

```
augcaauaac ugcuaacgac gaacguuacg cacuggcagc cuaagggccg ccguccucgc    120
acuggcucgc ugacgggcua ggucgcaag accagcgagg ucauuuacgu cagauaagcu     180
uuaggugagu cacgggccua gagacgaaaa cuuagugaau cgccgucgua gagcguguuc    240
guccgcgaug cggcgguuaa aucaaaugac agaacuaagu auguagaacu cucuguggag    300
ggcuugcgga cgcggguucg auuccc                                         326

<210> SEQ ID NO 146
<211> LENGTH: 363
<212> TYPE: RNA
<213> ORGANISM: Neisseria gonorrhoeae

<400> SEQUENCE: 146
gggggcgacc uuguuucga cggggguugc gaagcagaug cgggcauacc ggggucucag      60
auucccguaa aacacugaau ucaaauaguc gcaaacgacg aaacuuacgc uuuagccgcu    120
uaaggcuagc cguugcagca gucggucaau gggcugugug gugaaagcca ccgcaacguc    180
aucuuacauu gacugguuuc cagccggguu acuuggcagg aaauaagacu uaagguaacu    240
gguuuccaaa aggccuguug gucggcauga uggaaauaag auuuucaaau agacacaacu    300
aaguauguag aacgcuuugu agaggacuuu cggacggggg uucgauuccc cccgccucca    360
cca                                                                  363

<210> SEQ ID NO 147
<211> LENGTH: 363
<212> TYPE: RNA
<213> ORGANISM: Neisseria meningitidis

<400> SEQUENCE: 147
gggggcgacc uuguuucga cggggguugc gaagcagaug cgggcauacc ggggucucag      60
auucccguaa aacacugaau ucaaauaguc gcaaacgacg aaacuuacgc uuuagccgcu    120
uaaggcuagc cguugcagca gucggucaau gggcugugug gcgaaagcca ccgcaacguc    180
aucuuacauu gacugguuuc cugccggguu auuggcagg aaaugagauu uaagguaacu     240
gguuuccaaa aggccuguug gucggcauga uggaaauaag auuuucaaau agacacaacu    300
aaguauguag aacgcuuugu agaggacuuu cggacggggg uucgauuccc cccgccucca    360
cca                                                                  363

<210> SEQ ID NO 148
<211> LENGTH: 333
<212> TYPE: RNA
<213> ORGANISM: Chromobacterium violaceum

<400> SEQUENCE: 148
cggggguugc gaagcagaug agggcauacc gggauuucag ucaccccgua aaacgcugaa     60
uuuauauagu cgcaaacgac gaaacuuacg cucuggcagc cuaacggccg ccagacacu    120 acaacgguuc gcagauggc cggggcguc aaacccugu agugcacuc uacaucugcu       180 agugcuguuc cggguuacuu gguucagugc gaaauaauag guaacucgcc aaaguccagc    240
cuguccgucg gcguggcaga gguuaaaucc aaaugacacg acuaaguaug uagaacucac    300
uguagaggac uuucggacgc ggguucaacu ccc                                 333

<210> SEQ ID NO 149
<211> LENGTH: 330
<212> TYPE: RNA
<213> ORGANISM: Nitrosomonas cryotolerans
```

<400> SEQUENCE: 149

| | | |
|---|---|---|
| cgugggnuugc aaagcagcgc agggcauacc gaggaccaga auaccucgua aauacaucug | 60 |
| gaaaaaaaua gucgcaaacg acgaaaacua cgcuuuagcc gcuuaauacg gcuagccucu | 120 |
| gcaccgaugg gccuuaacgu cgggucuggc aacagacagc agagucauua gcaaggaucg | 180 |
| cguucuguag ggucacuuua cagaacguua aacaauaggu gacucgccug ccaucagccc | 240 |
| gccagcuggc gguugucagg uuaaauuaaa gagcauggcu aaguauguag aacugucugu | 300 |
| agaggacuug cggacgcggg uucaacuccc | 330 |

<210> SEQ ID NO 150
<211> LENGTH: 331
<212> TYPE: RNA
<213> ORGANISM: Methylobacillus glycogenes

<400> SEQUENCE: 150

| | | |
|---|---|---|
| cgggggnuugc aaagcagcgc agggcauacc gaggccuagu caccucguaa auaaacuaga | 60 |
| acaaguauag ucgcaaacga cgaaacuuac gcucuagccg cuuaaucccg gcuggacgcu | 120 |
| gcaccgaagg gccucucggu cggguggggu aacccacagc agcgucauua agagaggauc | 180 |
| gugcgauauu ggguuacuua auaucguauu aaauccaagg uaacucgccu gcuguuugcu | 240 |
| ugcucguugg ugagcaucag guuaaaucaa acaacacagc uaaguaugua aacugucug | 300 |
| uggagggcuu gcggacgggg guucgauucc c | 331 |

<210> SEQ ID NO 151
<211> LENGTH: 375
<212> TYPE: RNA
<213> ORGANISM: Pseudomonas testosteroni

<400> SEQUENCE: 151

| | | |
|---|---|---|
| ggggccgauu cuggauucga cguggguucg ggaccggugc ggugcaugnc gagcuugagu | 60 |
| gacgcucgua aaucuccauu caaaaaacua acugcaaacg acgaacguuu cgcacucgcc | 120 |
| gcuuaauccg gugagccuug caacagcacg cuagugggcu gggcaagggg guagcaauac | 180 |
| cuccccggcug caagggaauu uucauuagcu ggcuggauac cgggcuucuu gguauuugc | 240 |
| gagauuuuag gaagcuggcu acccaagcag cgugugccug cggggunugg guggcgagau | 300 |
| uuaaaacaga gcacuaaaca guagaucug uccggcgaag gcuuacggac gcggguucaa | 360 |
| uucccgccgg cucca | 375 |

<210> SEQ ID NO 152
<211> LENGTH: 353
<212> TYPE: RNA
<213> ORGANISM: Variovorax paradoxus

<400> SEQUENCE: 152

| | | |
|---|---|---|
| cgugggnuucg gagucgcagc ggggcauguc gagcugaaug cgcucguaaa acagauucaa | 60 |
| acaaacuaac ugcaaacgac gaacguuucg cacucgcugc uuaauugcca gugagccuug | 120 |
| caacaguugg ccgaugggcu gggcaagggg gucuggagca auccgaccu cccggcugca | 180 |
| aggauaacua caugggcugg cuccgauccg gguaccuugg gucggggcga gaaaauaggg | 240 |
| uacuggcguc cgguuuagcg ugugacgucg cgacuccgga agcgagacuc aaaacagauc | 300 |
| acuaaacaug uagaacugcg cgaugaaggc uugcggacgg ggguucaacu ccc | 353 |

<210> SEQ ID NO 153

<211> LENGTH: 345
<212> TYPE: RNA
<213> ORGANISM: Hydrogenophaga palleroni

<400> SEQUENCE: 153
cguggguucg gacgcgcagc agggcauguc gagguucugu caccucguaa aucagcagaa     60
aaaaaccaac ugcaaacgac gaacguuucg cacucgccgc uuaaacaccg gugagccuug    120
caacagcagg ccgaugggcu gggcaagggg gucgcaagac cucccggcug caagguaauu    180
uacaucggcu gguucugcgu cgggcaccuu ggcgcaggau gagauucaag gaugcuggcu    240
ucccguuuag cgugccacug cgcgacucgg gcggcgagac ccaaaucaga cggcuacaca    300
uguagaacug cucgaaaaag gcuugcggac ggggguucaa cuccc                    345

<210> SEQ ID NO 154
<211> LENGTH: 387
<212> TYPE: RNA
<213> ORGANISM: Bordetella pertussis

<400> SEQUENCE: 154
ggggccgauc cggauucgac gugggucaug aaacagcuca gggcaugccg agcaccagua     60
agcucguuaa uccacuggaa cacuacaaac gccaacgacg agcgucucgc ucucgccgcu    120
uaagcgguga gccgcugcac ugaucugucc uuggguucagg cggggaagg caacuuccca    180 gggggcaacc ccgaaccgca gcagcgacau ucacaaggaa ucggccaccg cugggguccac    240 acggcguugg uuuaaauuac gugaaucgcc cuggucggc ccgucgaucg gcuaagucca    300
ggguuaaauc caaauagauc gacuaagcau guagaacugg uugcggaggg cuugcggacg    360 ggguucaau uccccggc uccacca                                          387

<210> SEQ ID NO 155
<211> LENGTH: 323
<212> TYPE: RNA
<213> ORGANISM: Legionella pneumophila

<400> SEQUENCE: 155
cguggguugc aaaaccggaa gugcaugccg agaaggagau cucucguaaa uaagacucaa     60
uuaaauauaa augcaaacga ugaaaacuuu gcugggggg aagcuaucgc ugccuaauaa    120
gcacuuuagu uaaaccauca cuguguacug gccaauaaac ccaguauccc guucgaccga    180
gcccgcuuau cgguaucgaa ucaacguca uaagagauaa gcuagcgucc uaaucuaucc    240
cggguuaugg cgcgaaacuc agggaaucgc uguguaucau ccugcccguc ggaggagcca    300
caguuaaauu caaaagacaa ggc                                            323

<210> SEQ ID NO 156
<211> LENGTH: 315
<212> TYPE: RNA
<213> ORGANISM: Chromatium vinosum

<400> SEQUENCE: 156
cgugggucgc gaaaccuaag gugcaugccg aggugcgguu gacccucguaa aacccuccgc     60 aaacuuauag uugccaacga cgacaacuac gcucucgcug cuuaaucccca gcgggccucu    120 gaccgucacu ugccugugg cggcggauuc caggguuac cucacacagg aucgugguga    180
cgggaguccg gaccugaucc acuaaaaccu aacggaaucg ccgacugauc gcccugcccu    240 ucggcggca gaaggcuaaa aacaauagag ugggcuaagc auguaggacc gagggcagag    300
ggcuugcgga cgcgg                                                     315

<210> SEQ ID NO 157
<211> LENGTH: 318
<212> TYPE: RNA
<213> ORGANISM: Dichelobacter nodosus

<400> SEQUENCE: 157

| | | | | | |
|---|---|---|---|---|---|
| cucgaggugc | augucgagaa | ugagagaauc | ucguuaaaua | cuuucaaaac | uuauaguugc | 60 |
| aaacgacgac | aacuacgcuu | uagcggcuua | auucccgcuu | ucgcuuaccu | agauuugucu | 120 |
| gugguuuac | cguaagcgac | auuaacacag | aaucgcuggu | uacgcgucc | gcuguuaauc | 180 |
| gguuaaauua | agcggaaucg | cuuguaaaau | gccugagcgu | uggcuguuua | ugaguuaaac | 240 |
| cuaauuaacu | gcucuaaaca | uguaguacca | aaaguuaagg | auucgcggac | ggggguucaa | 300 |
| auccccccgc | cuccacca | | | | | 318 |

<210> SEQ ID NO 158
<211> LENGTH: 354
<212> TYPE: RNA
<213> ORGANISM: Pseudomonas aeruginosa

<400> SEQUENCE: 158

| | | | | | |
|---|---|---|---|---|---|
| ggggccgauu | aggauucgac | gccgguaaca | aaacuugagg | ggcaugccga | gcugguagca | 60 |
| gaacucguaa | auucgcugcu | gcaaacuuau | aguugccaac | gacgacaacu | acgcucuagc | 120 |
| ugcuuaaugc | ggcuagacag | ucgcuagggg | augccuguaa | acccgaaacg | acugucagau | 180 |
| agaacaggau | cgccgccaag | uucgcuguag | acguaacgc | uaaaacucau | acagcucgcu | 240 |
| ccaagcaccc | ugccacucgg | gcggcgcgga | guuaacucag | uagagcuggc | uaagcaugua | 300 |
| gaaccgauag | cggagagcug | gcggacgggg | guucaaauccc | ccccggcucc | acca | 354 |

<210> SEQ ID NO 159
<211> LENGTH: 350
<212> TYPE: RNA
<213> ORGANISM: Pseudomonas fluorescens

<400> SEQUENCE: 159

| | | | | | |
|---|---|---|---|---|---|
| cgccgguugc | gaaccuuuag | gugcaugccg | aguugguaac | agaacucgua | aauccacugu | 60 |
| ugcaacuuuc | uuaguugcca | augacgaaac | cuacggggaa | uacgcucucg | cugcguaagc | 120 |
| agccuuagcc | cuucccuccu | gguaccuucg | gguccagcaa | ucaucagggg | augucuguaa | 180 |
| acccaaagug | auugucauau | agaacagaau | cgccgugcag | uacguugugg | acgaagcggc | 240 |
| uaaaacuuac | acaacucgcc | caaagcaccc | ugcccgucgg | gucgcugagg | guuaacuuaa | 300 |
| uagacacggc | uacgcaugua | guaccgacag | cagaguacug | gcggacgggg | | 350 |

<210> SEQ ID NO 160
<211> LENGTH: 323
<212> TYPE: RNA
<213> ORGANISM: Marinobacter hydrocarbonoclasticus

<400> SEQUENCE: 160

| | | | | | |
|---|---|---|---|---|---|
| cgccggugac | gaacccuugg | gugcaugccg | agauggcagc | gaaucucgua | aauccaaagc | 60 |
| ugcaacguaa | uagucgcaaa | cgacgaaaac | uacgcacugg | cggcguaagc | cguuccaguc | 120 |
| guccuggcug | aggcgccuau | aacucaguag | caacaucccca | ggacgucauc | gcuuauaggc | 180 |
| ugcuccguuc | accagagcuc | acuggugunc | ggcuagagauu | aaaagagcucg | ccucuugcac | 240 |
| ccugaccuuc | gggucgcuug | agguuaaauc | aauagaagga | cacuaagcau | guagaccuca | 300 |

```
aggccuagug cuggcggacg cgg                                              323
```

```
<210> SEQ ID NO 161
<211> LENGTH: 355
<212> TYPE: RNA
<213> ORGANISM: Shewanella putrefaciens

<400> SEQUENCE: 161
gggggcgauu cuggauucga caggauucac gaaacccugg gagcaugccg agggggcgguu      60 ggccucguaa aaagccgcaa aguuauaguu gcaaacgacg auaacuacgc ucuagccgcu     120
uaaugccgcu agccaucuac cacacgcuuu gcacaugggc aguggauuug auggucaucu     180
cacaucgugc uagcgaggga acccugucug ggggugaacc gcgaaacagu accggacuca     240
ccguguggga uccugucuuu cggaguucaa acgguuaaac aauagaaaga cuaagcaugu     300
agcgccuugg auguaagguu ucggacgcg gguucaaguc ccgccgccuc cacca           355
```

```
<210> SEQ ID NO 162
<211> LENGTH: 314
<212> TYPE: RNA
<213> ORGANISM: Pseudoalteromonas haloplanktis

<400> SEQUENCE: 162
cggaauucaa gaagcccgag gugcaugucg aggugcgguu ugccucguaa aaagccgca       60 auuuaaagua aucgcaaacg acgauaacua cucucuagca gcuuaggcug gcuagcgcuc    120
cuuccaugua uucuugugga cuggauuuug gagugucacc cuaacaccug aucgcgacgg    180
aaacccuggc cggggguugaa gcguuaaaac uaagcggccu cgccuuuauc uaccguguuu    240
guccgggauu uaaagguuaa uuaaaugaca auacuaaaca guaguaccg acggucgagg     300 cuuuucggac gggg                                                      314
```

```
<210> SEQ ID NO 163
<211> LENGTH: 316
<212> TYPE: RNA
<213> ORGANISM: Aeromonas salmonicida

<400> SEQUENCE: 163
caagauucac gaaacccaag gugcaugccg aggugcggua ggccucguua acaaaccgca      60
aaaaaauagu cgcaaacgac gaaaacuacg cacuagcagc uuaauaaccu gcauagagcc    120
cuucuacccu agcuugccug guccuaggg aaucggaagg ucauccuuca caggaucgug    180
uggaaguccu gcucggggcg gaagcauuaa aaccaaucga gcuagucaau ucguggcgug    240
ucucuccgca gcggguuggc gaauguaaag agugacuaag cauguaguac cgaggaugua    300
guaauuuugg acgggg                                                    316
```

```
<210> SEQ ID NO 164
<211> LENGTH: 363
<212> TYPE: RNA
<213> ORGANISM: Salmonella typhimurium

<400> SEQUENCE: 164
ggggcugauu cuggauucga cggauuugc gaaacccaag gugcaugccg agggggcgguu      60 ggccucguaa aaagccgcaa aaaauaguc gcaaacgacg aaaccuacgc uuuagcagcu    120
uaauaaccug cuuagagccc ucucucccua gccuccgcuc uuaggacggg gaucaagaga    180
ggucaaaccc aaaagagauc gcgcggaugc ccugccuggg guugaagcgu uaaaacgaau    240
caggcuaguc ugguagugc gugucccgucc gcaggugcca ggcgaaugua aagacugacu    300
```

```
aagcauguag uaccgaggau guaggaauuu cggacgcggg uucaacuccc gccagcucca    360
cca                                                                  363
```

```
<210> SEQ ID NO 165
<211> LENGTH: 363
<212> TYPE: RNA
<213> ORGANISM: Escherichia coli

<400> SEQUENCE: 165
ggggcugauu cuggauucga cgggauuugc gaaacccaag gugcaugccg aggggcgguu     60
ggccucguaa aaagccgcaa aaaauagucg caaacgacga aaacuacgcu uuagcagcuu    120
aauaaccugc uuagagcccu cucucccuag ccuccgcucu uaggacgggg aucaagagag    180
gucaaaccca aaagagaucg cguggaagcc cugccugggg uugaagcguu aaaacuuaau    240
caggcuaguu uguuagugge guguccgucc gcagcuggca agcgaaugua aagacugacu    300
aagcauguag uaccgaggau guaggaauuu cggacgcggg uucaacuccc gccagcucca    360
cca                                                                  363
```

```
<210> SEQ ID NO 166
<211> LENGTH: 364
<212> TYPE: RNA
<213> ORGANISM: Yersinia pestis

<400> SEQUENCE: 166
ggggcugauu cuggauucga cgggauucgc gaaacccaag gugcaugccg aggugcggug     60
gccucguaaa aaccgcaaa aaaauaaguu gcaaacgacg aaaacuacgc acuagcagcu    120
uauuaaccug cuuagagccc ucucuccuua gccuccgcuc uuaggacggg gaucaagaga    180
ggucaaaccu aaaagagcuc gugugggaaac cuugccuggg guggaagcau aaaacuaau    240
caggauaguu ugucaguagc guguccaucc gcagcuggcc ggcgaaugua augauuggac    300
uaagcaugua gugccgacgg uguaguaauu ucggacgggg guucaaauco ccccagcucc    360
acca                                                                 364
```

```
<210> SEQ ID NO 167
<211> LENGTH: 367
<212> TYPE: RNA
<213> ORGANISM: Vibrio cholerae

<400> SEQUENCE: 167
ggggcugauu caggauucga cgggaauuuu gcagucugag gugcaugccg aggugcggua     60
ggccucguua acaaaccgca aaaaaauagu cgcaaacgac gaaaacuacg cacuagcagc    120
uuaauacccu gcucagagcc cuuccucccu agcuuccgcu uguaagacgg ggaaaucagg    180
aaggucaaac caaucaagc uggcguggau uccccaccu gagggaugaa gcgcgagauc    240
uaauucaggu uagccauucg uuagcguguc gguucgcagg cgguggugaa auuaaagauc    300
gacuaagcau guaguaccaa agaugaaugg uuuucggacg gggguucaac uccccccagc    360
uccacca                                                             367
```

```
<210> SEQ ID NO 168
<211> LENGTH: 366
<212> TYPE: RNA
<213> ORGANISM: Haemophilus influenzae

<400> SEQUENCE: 168
```

```
gggcugauu cuggauucga cgggauuagc gaagcccaag gugcacgucg aggugcggua      60
ggccucguaa auaaaccgca aaaaaauacu cgcaaacgac gaacaauacg cuuuagcagc    120
uuaauaaccu gcauuuagcc uucgcgcucc agcuuccgcu cguaagacgg ggauaacgcg    180
gagucaaacc aaaacgagau cgugugguag ccaccguuug aggaucgaag cacuaaauug   240
aaucaaacua gcuuaaguuu agcgugucug uccgcaugcu uaagugaaau uaaagacgag    300
acuaaacgug uaguacugaa gguagaguaa uuucggacgg ggguucaacu cccccagcu    360 ccacca                                                               366
```

<210> SEQ ID NO 169
<211> LENGTH: 366
<212> TYPE: RNA
<213> ORGANISM: Haemophilus actinomycetemcomitans

<400> SEQUENCE: 169

```
gggcugauu cuggauucga cgggauuagc gaagcccgaa gugcacgucg aggugcggua     60
ggccucguaa auaaaccgca aaaaauagu cgcaaacgac gaacaauacg cuuuagcagc    120
uuaauaaccu gccuuuagcc uucgcucccc agcuuccgcu cguaagacgg ggauaaagcg    180
gagucaaacc aaaacgagau cguguggaag ccaccguuug aggaucgaag cauuaaauua    240
aaucaaagua gcuuaauugu cgcguguccg ucagcaggau uaagugaauu uaaagaccgg    300
acuaaacgug uagugcuaac ggcagaggaa uuucggacgg ggguucaacu cccccagcu    360 ccacca                                                               366
```

<210> SEQ ID NO 170
<211> LENGTH: 354
<212> TYPE: RNA
<213> ORGANISM: Desulfovibrio desulfuricans

<400> SEQUENCE: 170

```
cggggacgug gaagccguag cggcaggucg aggcgccgcu ggccucguaa aaagcggcac     60
aaaaguaauu gccaacaacg auuacgacua cgcuuacgcu gccuaauaac agcgaggcaa    120
ugaccguuua acgucgcgc cgaucagggc caugccugau aacccugauu cacuuaucag    180
gcuggcgaaa accggcucuc gccggggugu uucgcgagga guuuaccggc gggauuccug    240
cguugugccu ggucagggc caacagcgcg gugaaauaca uacuugaccu aaaccuguag    300
augcuucgug uggaauguuc ucggacgggg guucaaaucc ccccggcucc acca           354
```

<210> SEQ ID NO 171
<211> LENGTH: 366
<212> TYPE: RNA
<213> ORGANISM: Myxococcus xanthus

<400> SEQUENCE: 171

```
gggggcggaa aggauucgac gggggcauug aaguucgaga cgcgugccga gcuugucagg    60
uagcucguaa auucaacccg gcaaagacac aaaagccaac gacaacguug agcucgcgcu    120
ggcugccuaa aaacagccca uagucgcggu uccccccgcc cucggccgu ggguuggga    180 cagaccguca uaaugcaggc uggcugccga gggugccugg acccgaggug gcgagaucuu    240
cccaggaccg gcucgaguaa ucccguccgu gggagccuca gggacguagc aaaucgcgga    300
cuacgcacgu agggucgaag agcggacggc uuucggacgc gggucgauu cccgccgccu    360 ccacca                                                               366
```

-continued

<210> SEQ ID NO 172
<211> LENGTH: 346
<212> TYPE: RNA
<213> ORGANISM: Bdellovibrio bacteriovirus

<400> SEQUENCE: 172

| | | | | | |
|---|---|---|---|---|---|
| ggggcggaa | aggauucgac | gggggugcug | aagcauaagg | agcauaccgg | ggcggaugag | 60 |
| gaccucguua | aaaacgucca | cuuuguaauu | ggcaacgauu | acgcacuugc | agcuuaauua | 120 |
| agcagcacga | ucaaccuugu | ggugguuccg | cacuuggauu | gaucgucauu | uagggaccuc | 180 |
| ggcguguugg | guuucucca | gcagacaugc | uuaaauuuac | uggggagag | gucuuaggga | 240 |
| uuuugucugu | ggaagcccga | ggaccaaucu | aaaacacuga | cuaaguaugu | agcgccuuau | 300 |
| cguggaucau | uugcggacgg | ggguucgauu | cccgccgccu | ccacca | | 346 |

<210> SEQ ID NO 173
<211> LENGTH: 386
<212> TYPE: RNA
<213> ORGANISM: Helicobacter pylori

<400> SEQUENCE: 173

| | | | | | |
|---|---|---|---|---|---|
| ggggcugacu | uggauuucga | cagauuucuu | gucgcacaga | uagcaugcca | agcgcugcuu | 60 |
| guaaaacagc | aacaaaaaua | acuguaaaca | acacagauua | cgcuccagcu | uacgcuaaag | 120 |
| cugcgugagu | uaaucuccuu | uuggagcugg | acgauuaga | auuucuagcg | uuuuaaucgc | 180 |
| uccauaaccu | uaagcuagac | gcuuuuaaaa | ggugguucgc | cuuuuaaacu | aagaaacaag | 240 |
| aacucuugaa | acuaucucaa | gguuuuagaa | aguuggacca | gagcuaguuu | uaaggcuaaa | 300 |
| aaaccaacca | auuuucuaag | cauuguagaa | guuuguguuu | agggcaagau | uuuuggacug | 360 |
| ggguucgauu | ccccacagcu | ccacca | | | | 386 |

<210> SEQ ID NO 174
<211> LENGTH: 359
<212> TYPE: RNA
<213> ORGANISM: Campylobacter jejuni

<400> SEQUENCE: 174

| | | | | | |
|---|---|---|---|---|---|
| gggagcgacu | uggcuucgac | aggaguaagu | cugcuuagau | ggcaugucgc | uuugggcaaa | 60 |
| gcguaaaaag | cccaaauaaa | auuaaacgca | aacaacguua | aauucgcucc | ugcuuacgcu | 120 |
| aaagcugcgu | aaguucaguu | gagccugaaa | uuuaagucau | acuaucuagc | uuaauuuucg | 180 |
| gucauuuuug | auaguguagc | cuugcguuug | acaagcguug | aggugaaaua | aagucuuagc | 240 |
| cuugcuuuug | aguuuggaa | gaugagcgaa | guagggugaa | guagucaucu | uugcuaagca | 300 |
| uguagagguc | uuugugggau | uauuuuugga | cagggguucg | auucccccucg | cuuccacca | 359 |

<210> SEQ ID NO 175
<211> LENGTH: 355
<212> TYPE: RNA
<213> ORGANISM: Sulfurospirillum deleyianum

<400> SEQUENCE: 175

| | | | | | |
|---|---|---|---|---|---|
| caggaguagu | uuuagcuuau | ggcugcaugu | cgggagugag | ggucuuccgu | uacacaaccu | 60 |
| ucaaacaaua | acugcuaaca | acaguaacua | ucguccugcu | uacgcgcuag | cugcguaagu | 120 |
| uuaacaaaua | auggacugcu | cuccccuuug | augcuaucuu | aggaggucuu | ggagaguauc | 180 |
| auagauuuga | uagcuauauu | acaugaacgc | cuuuacaugu | aaugaaguua | aaggcucguu | 240 |

-continued

```
uucguaguuu ucugauuguu guacgaagca aaauuaaaca cuaucaacaa uaucuaagca     300
uguagacguc auagguggcu auuuuuggac uggguucaa cucccgccag cucca          355
```

EUBACTERIAL TMRNA SEQUENCES AND USES THEREOF

CROSS-REFERENCE TO RELATED APPLICATIONS

The present application is a national stage filing under 35 U.S.C. §371 of PCT/US00/08988 filed on 6 Apr. 2000. The present application is also related to and claims priority under 35 U.S.C. §119(e) to U.S. provisional patent application Ser. No. 60/128,058 filed on 7 Apr. 1999.

BACKGROUND OF THE INVENTION

The present invention is directed to eubacterial tmDNA sequences and the corresponding tmRNA sequences. The present invention is further directed to alignments of eubacterial tmDNA sequences and use of the sequences and sequence alignments for the development of antibacterial drugs. The present invention is also directed to the use of the sequences for the development of diagnostic assays.

The publications and other materials used herein to illuminate the background of the invention or provide additional details respecting the practice are incorporated by reference, and for convenience are respectively grouped in the appended List of References.

Eubacterial tmRNAs (10Sa RNAs) are unique since they function, at least in *E. coli*, both as tRNA and as mRNA (for a review, see Muto et al., 1998). These ~360±10% nucleotide RNAs are charged with alanine at their 3'-ends (Komine et al., 1994; Ushida et al., 1994) and also have a short reading frame coding for 9 to 27 amino acids depending on the bacterial species. *E. coli* tmRNA mediates recycling of ribosomes stalled at the end of terminatorless mRNAs; via a trans-translation process (Tu et al., 1995; Keiler et al., 1996; Himeno et al., 1997). In *E. coli*, this amino acid tag is co-translationally added to polypeptides synthesized from mRNAs lacking a termination codon, and the added 11 amino acid C-terminal tag makes the protein a target for specific proteolysis (Keiler et al., 1996).

Structural analyses based on phylogenetic (Felden, et al., 1996; Williams and Bartel, 1996) and probing (Felden et al., 1997; Hickerson et al., 1998) data have led to a compact secondary structure model encompassing 6 helices and 4 pseudoknots. tmRNAs have some structural similarities with canonical tRNAs, especially with tRNA acceptor branches. *E. coli* tmRNA contains two modified nucleosides, 5-methyluridine and pseudouridine, located in the tRNA-like domain of the molecule, in a seven-nucleotide loop mimicking the conserved sequence of T loops in canonical tRNAs (Felden et al., 1998).

Fifty-three tmRNA sequences are now known from both experimental data and Blast searches on sequenced genomes (summarized in Williams, 1999; Wower and Zwieb, 1999). These sequences cover only 10 phyla, less than one third of the known bacterial taxa. It is desired to determine additional tmRNA sequences and to use the tmRNA sequences for drug development.

SUMMARY OF THE INVENTION

The present invention relates to eubacterial tmDNA sequences and the corresponding tmRNA sequences. The present invention further relates to alignments of eubacterial tmDNA sequences and use of the sequences and sequence alignments for the development of antibacterial drugs.

In one aspect of the present invention, an extensive phylogenetic analysis was performed. Fifty-eight new tmDNA sequences including members from nine additional phyla were determined. Remarkably, tmDNA sequences could be amplified from all species tested apart from those in the alpha-Proteobacteria. This aspect of the invention allowed a more systematical study of the structure and overall distribution of tmRNA within eubacteria.

In a second aspect of the invention, alignments are made with the newly isolated tmDNA sequences and previously disclosed tmRNA sequences.

In a third aspect of the invention, the alignments of the tmRNA sequences allow the identification of targets for development of antibacterial drugs.

In a fourth aspect of the invention, the novel tmDNA or tmRNA sequences of the present invention are used to develop diagnostic assays, such as amplification-based assays, for the bacterial species disclosed herein.

BRIEF DESCRIPTION OF THE FIGURES

FIGS. 1A–1B show the effect of the annealing temperature (FIG. 1A) and magnesium concentration (FIG. 1B) on amplifying eubacterial tmRNA genes from genomic DNAs using PCR. A: Varying the annealing temperature from 50° to 70° C. during the PCR amplification of *Thermus aquaticus* (1). B; Varying the magnesium concentration to amplify tmDNA genes from *Thermus aquaticus* (1), negative effect of increasing the magnesium concentration), *Acholeplasma laidlawii* (2), positive effect of increasing the magnesium concentration, the upper band is the tmDNA gene) and from *Mycoplasma salivarium* (3), no discernible effect of magnesium ions in that concentration range). The arrows point toward the 4 novel tmDNA genes that have been sequenced.

FIGS. 3A, 3B and 3C show the sequence alignment, structural domains and structural features for the tmRNA of several species of Firmicutes. The tmRNA sequences are set forth in SEQ ID NOs:67–87.

FIGS. 4A and 4B show the sequence alignment, structural domains and structural features for the tmRNA of several species of Thermophiles. The tmRNA sequences are set forth in SEQ ID NOs:88–99.

Figure 7D:
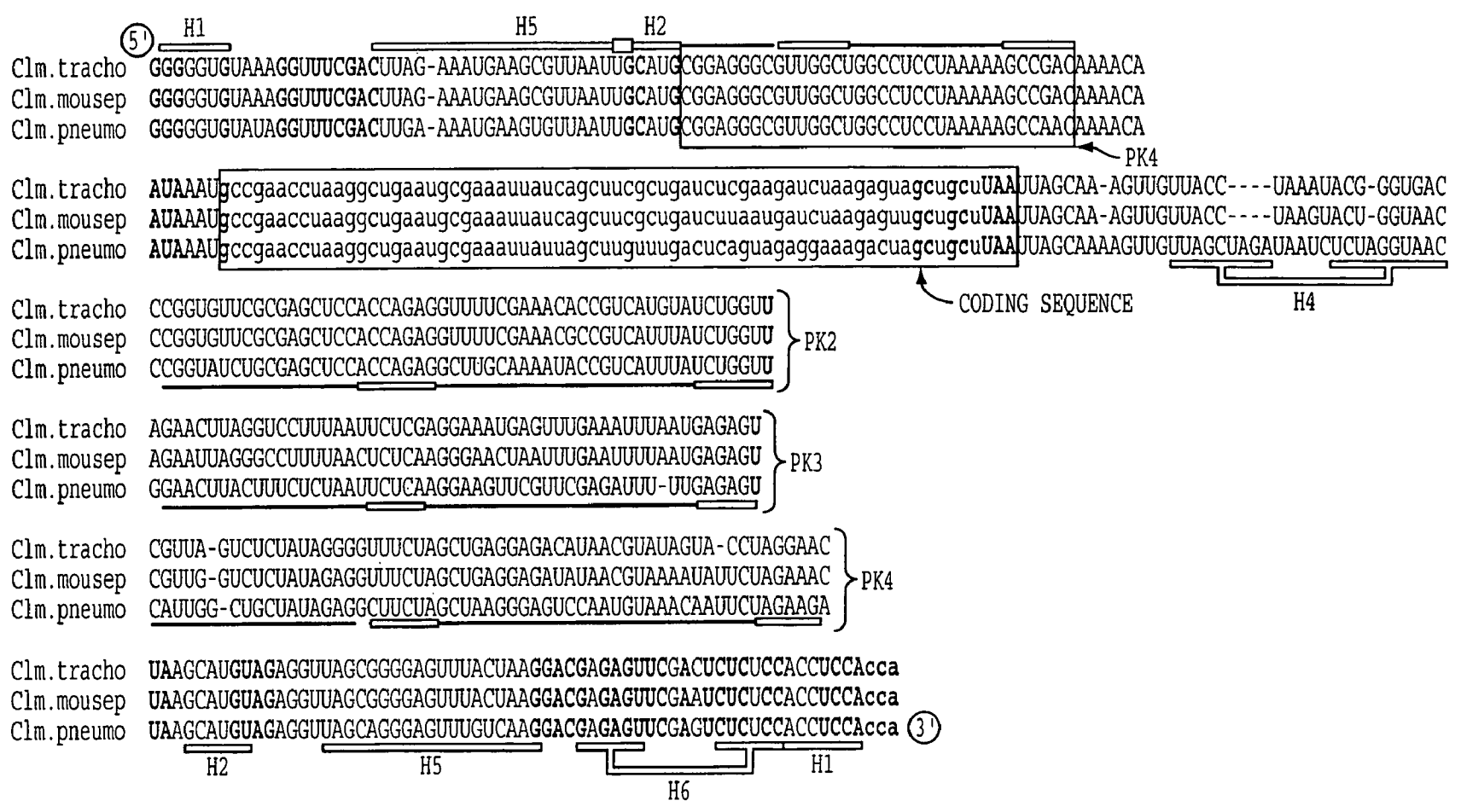

FIGS. 7A-1, 7A-2, 7B, 7C and 7D show the sequence alignment, structural domains and structural features for the tmRNA of several species of Mesophiles (7A-1, 7A-2, 7C, 7D) and environmental sludge (7B). The tmRNA sequences of the Mesophiles are set forth in SEQ ID NOs:118–123 and 125–128, and the tmRNA sequence of the environmental sludge is set forth in SEQ ID NO:124.

FIGS. 9A and 9B show the sequence alignment, structural domains and structural features for the tmRNA of several species of Pourpres beta. The tmRNA sequences are set forth in SEQ ID NOs:143–154.

FIGS. 10A, 10B and 10C show the sequence alignment, structural domains and structural features for the tmRNA of several species of Pourpres gamma. The tmRNA sequences are set forth in SEQ ID NOs:155–169.

DETAILED DESCRIPTION OF THE INVENTION

Figure 2:
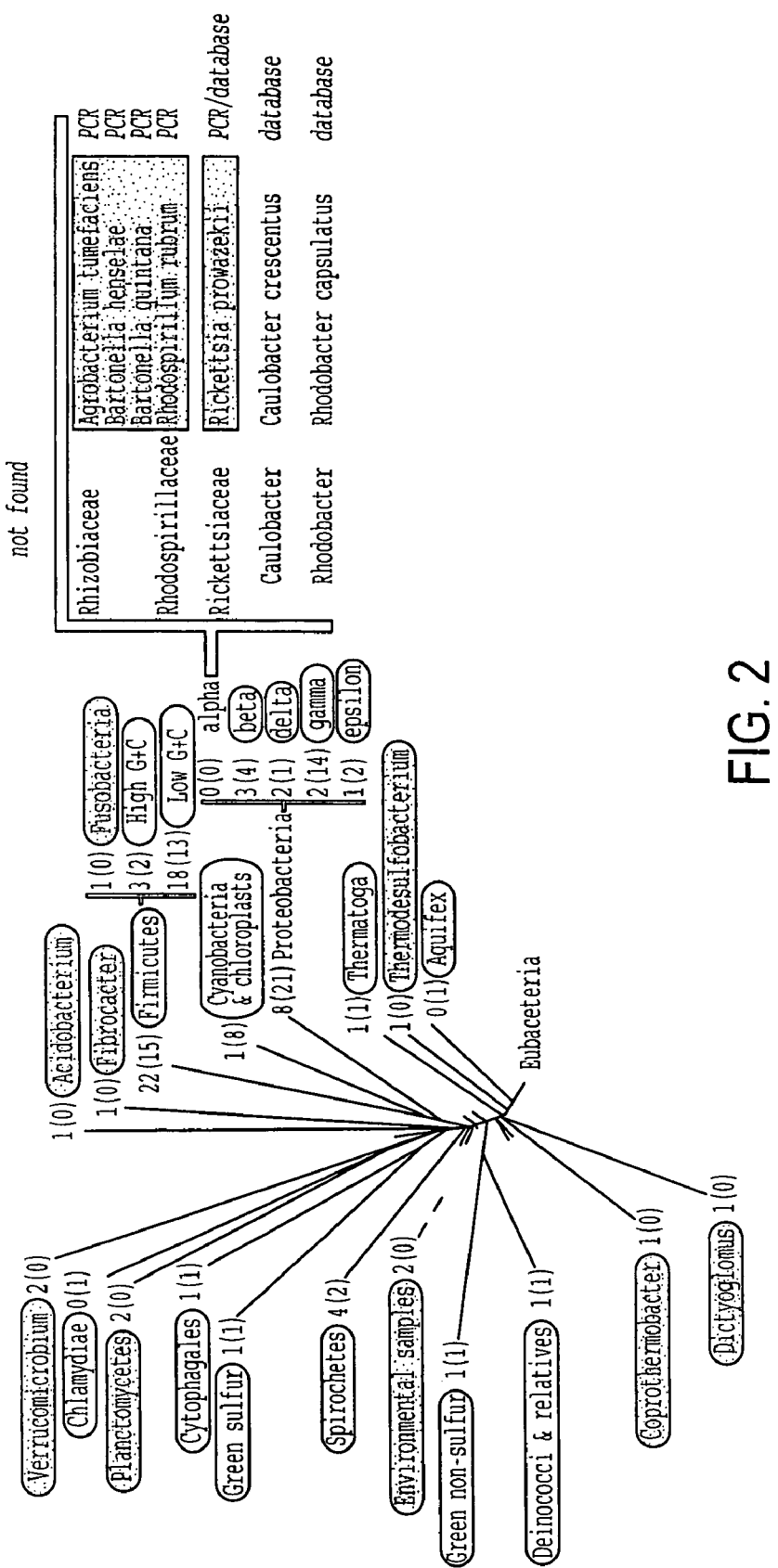
FIG. 2 shows the distribution of tmDNA sequences within eubacterial genomes. The circled phyla or subgroups contain tmDNA sequences and those shaded are new members of this category. The numbers shown close to each phylum are the 51 tmDNA sequences that have are disclosed herein and the numbers in parenthesis are the 53 tmDNA sequences that were previously known (summarized in Williams, 1999; Wower and Zwieb, 1999). The environmental samples are indicated with a dashed line as their connection to the tree is unknown. The 5 alpha-Proteobacteria in which tmDNA sequences were not detected by PCR analysis are labeled "PCR" and the 3 analyzed by Blast search of the complete, or nearly complete, sequenced genomes are labeled "database".
Figure 3A:
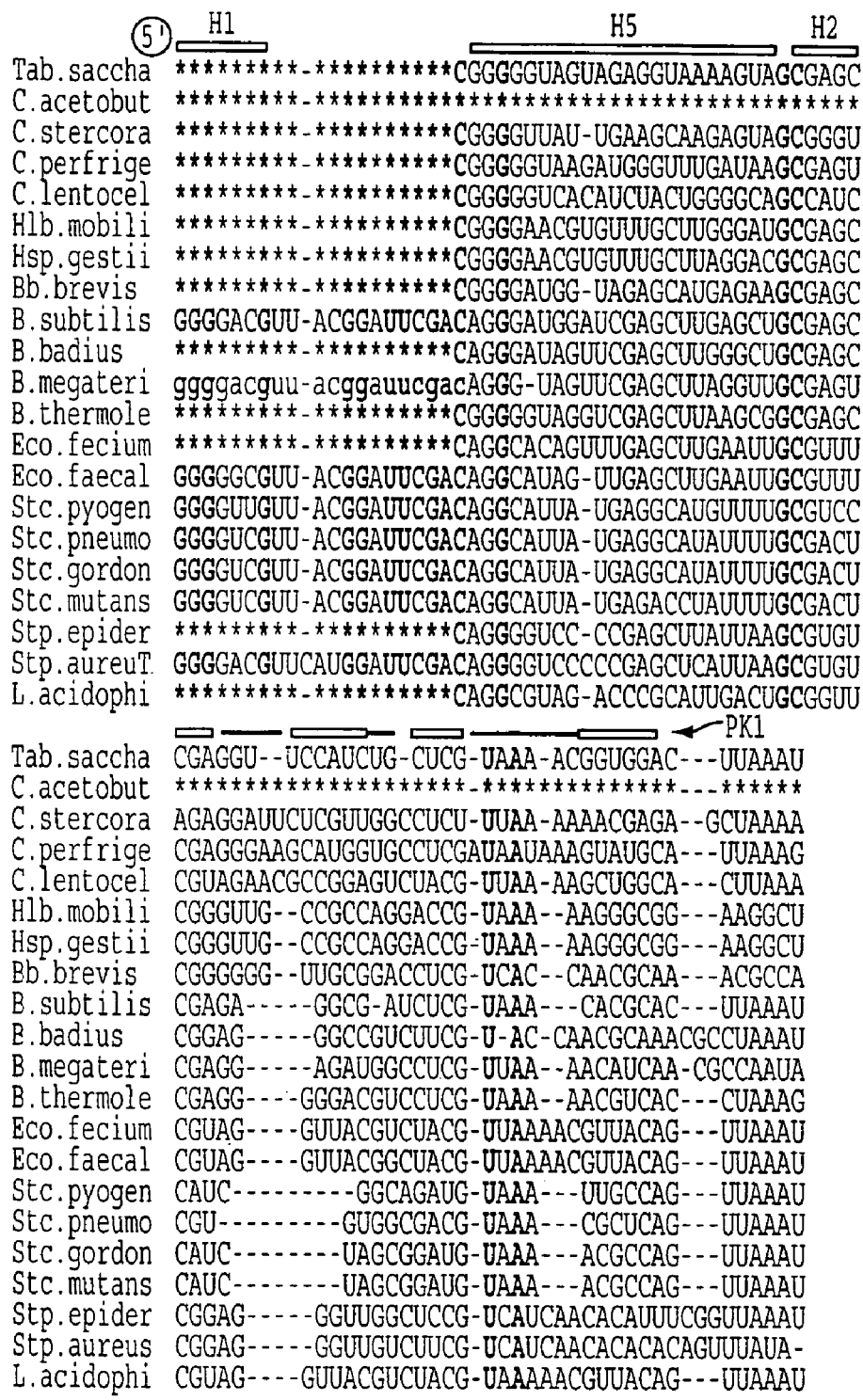
Figure 3C:
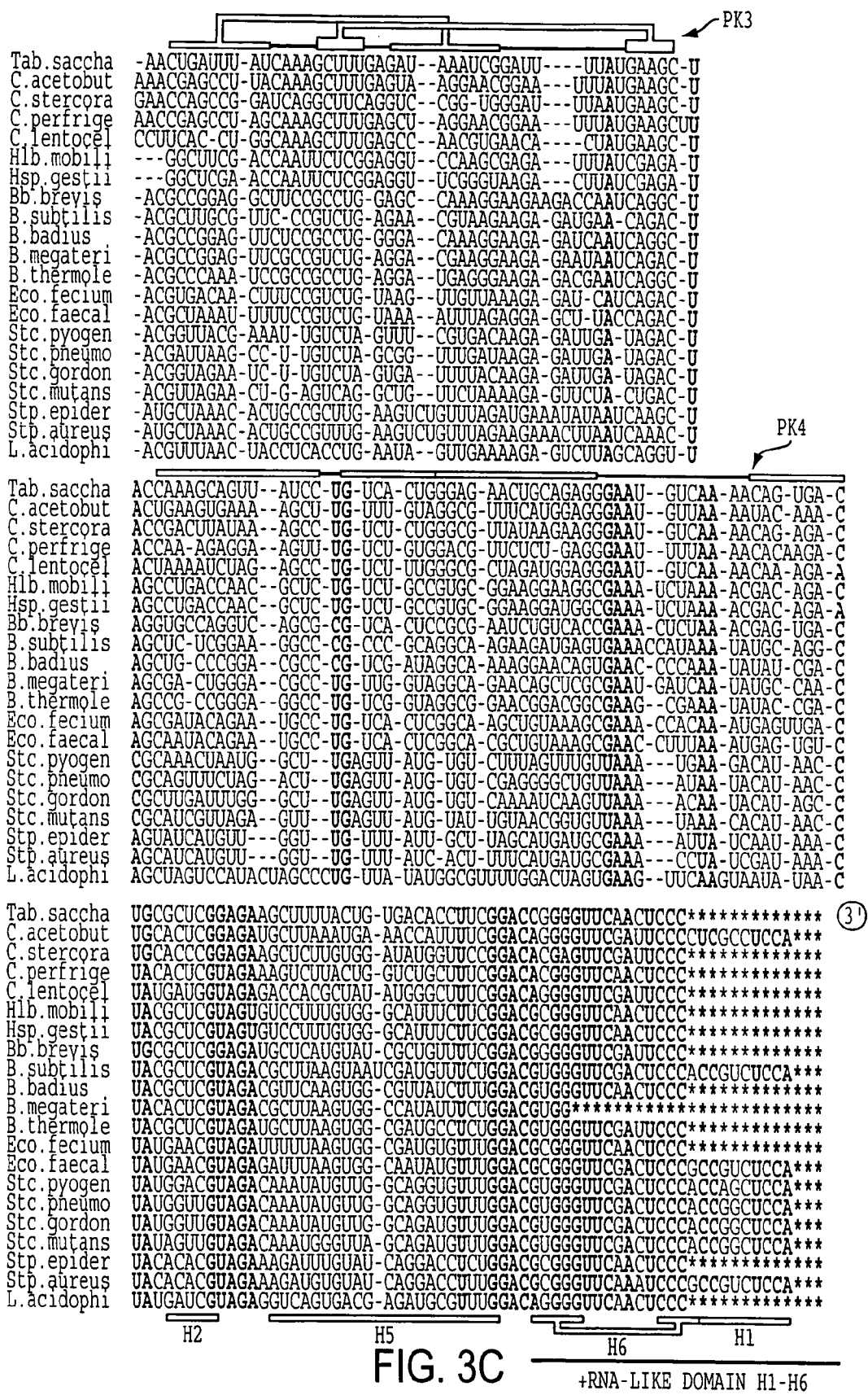
Figure 5A:
FIGS. 5A and 5B show the sequence alignment, structural domains and structural features for the tmRNA of several species of Cyanobacteries (5A) and chloroplasts (5B). The tmRNA sequences of the Cyanobacteries are set forth in SEQ ID NOs:100–103, and the tmRNA sequences of the chloroplasts are set forth in SEQ ID NOs:104–108.
Figure 5B:
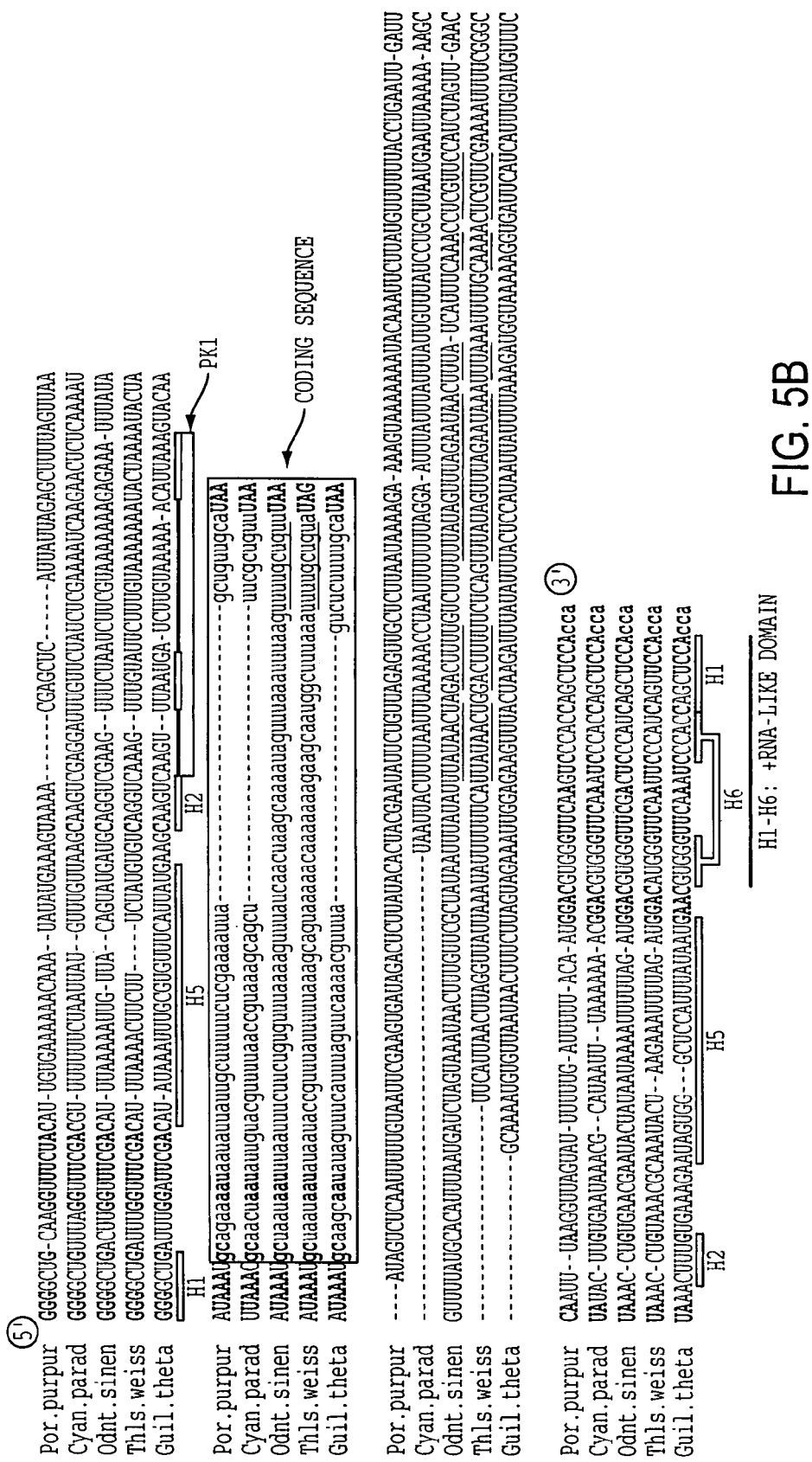
Figure 6A:
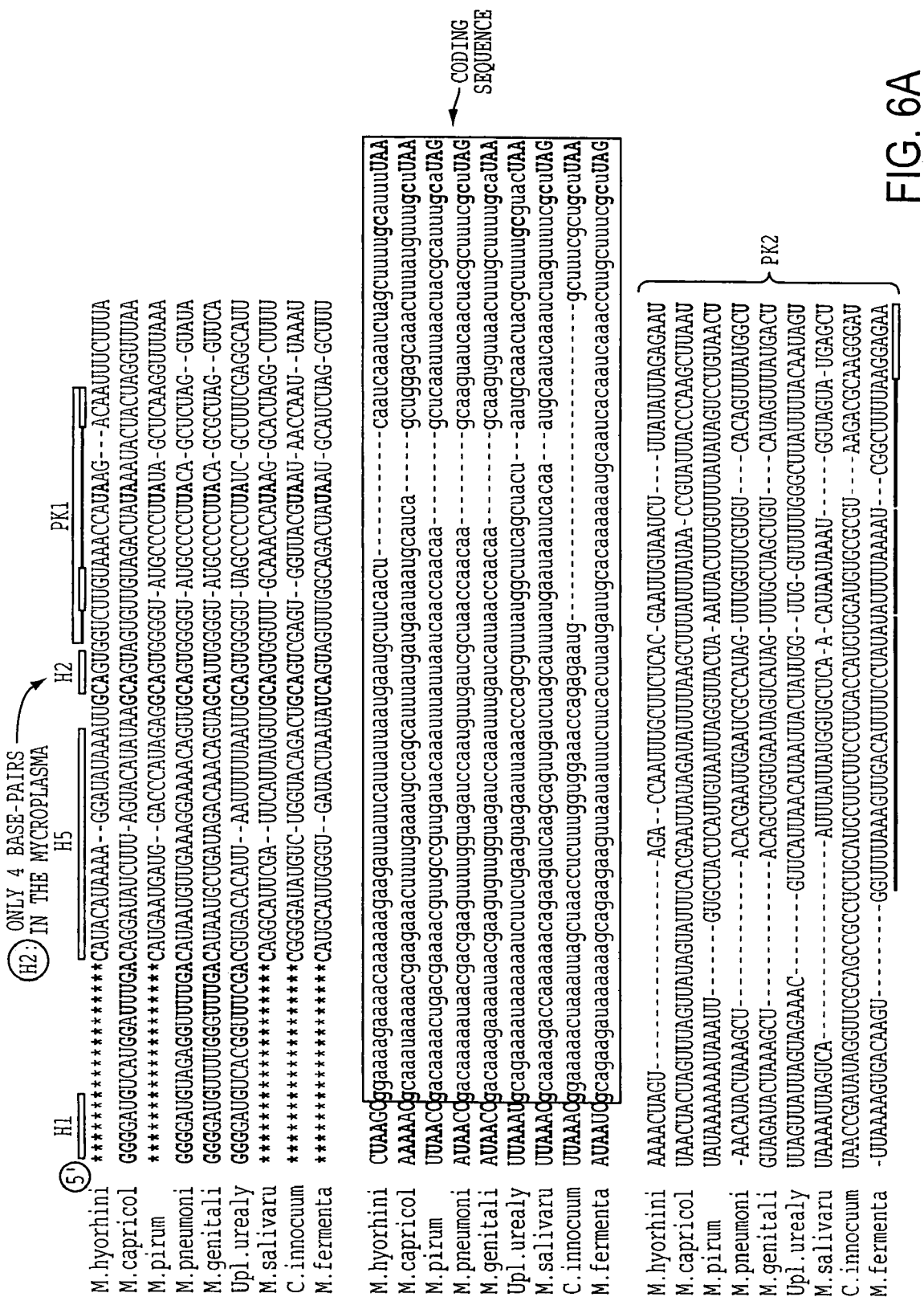
FIGS. 6A and 6B show the sequence alignment, structural domains and structural features for the tmRNA of several species of Mycoplasmes. The tmRNA sequences are set forth in SEQ ID NOs:109–117.
Figure 6B:
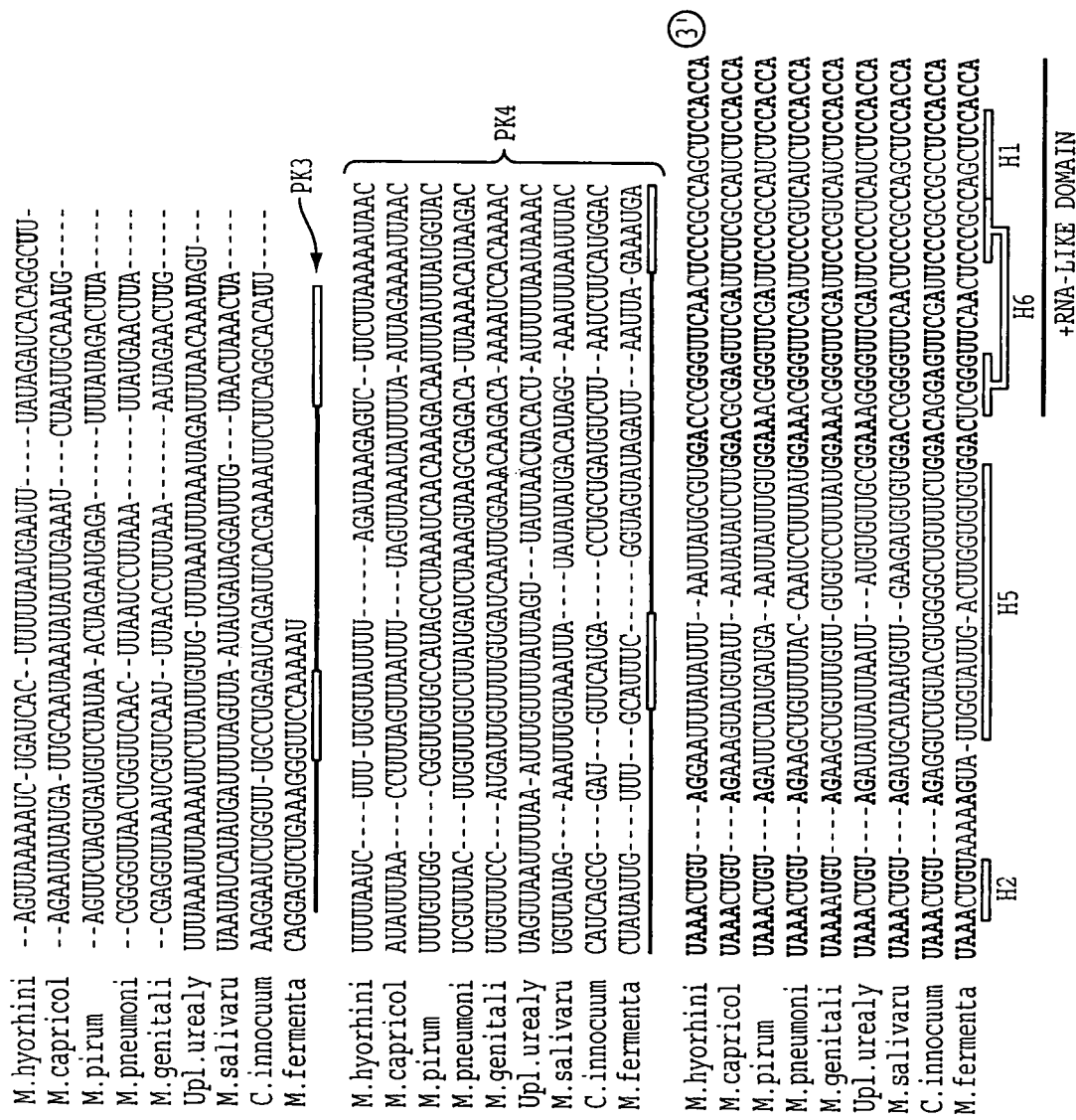

The present invention is directed to eubacterial tmDNA sequences and the corresponding tmRNA sequences. The present invention is further directed to alignments of eubacterial tmDNA sequences and use of the sequences and sequence alignments for the development of antibacterial drugs.

The novel eubacterial tmDNA sequences determined in accordance with the present invention are set forth in Tables 1–58, below. The alignment of tmRNA sequences is shown in FIGS. 3A–11B, which also show the structural domains and structural features of the tmRNA. The present invention also includes the tmRNA sequences set forth in these figures to the extent they differ from the sequences set forth in Tables 1–58.

The sequences, especially as identified by the sequence alignment, represent targets for the development of drugs which may be broadly applicable to many kinds of bacteria, or may be broadly applicable only to a particular genera of phylum of bacteria, or may be specifically applicable to a single species of bacteria. Thus, the present invention is further directed to the development of drugs for the therapeutic treatment of bacteria, generically or specifically. Suitable drugs are developed on the basis of the tmRNA sequences as described herein.

For all the novel tmRNA sequences, as well as with the ones that are already known, there are systematically several structural domains that are always found. These domains can be used as targets for the development of drugs which may be genera specific or which may be eubacteria specific. These domains are either RNA helices which can be sometimes interrupted by bulges or pseudoknots. The RNA helices which are always present are H1, H2, H5 and H6. Helices H1 and H6 are found in all canonical transfer RNAs. Thus, H1 and H6 are not good targets for drug development because drugs that would target them will also interfere with the biology of the individual that has a given disease. Consequently, very good candidates for development of drugs for targeting as many bacteria as possible are helices H2 and H5. Moreover, helices H2 and H5 are critical for the folding of all these tmRNA since both of them connect the two ends of the molecule together. Disruption of either H2 or H5 with a specific drug would lead to inactive tmRNA molecules in vivo. Similarly, pseudoknots PK1, PK2 and PK3 are always found in the bacterial tmRNAs. Since these pseudoknots are not found in all canonical transfer RNAs, they can also be targeted with specific drugs. Disruption of either PK1 or PK2 or PK3 with a specific drug would lead to inactive tmRNA molecules in vivo.

In addition to developing drugs which broadly target many bacteria, drugs are developed which are more genera specific. For trying to target specifically a given bacteria or a complete phylum, the coding sequence (shown in all the alignments) is a very good candidate. Indeed, this region of the RNA is very accessible for DNA antisense binding (such as shown for *Escherichia coli*; Matveeva et al., 1997), and thus, is also available for interaction with other drugs. Moreover, the coding sequence is a critical functional domain of the molecule in its quality-control mechanism in cells.

Interestingly, some structural domains are present only in a given bacterial phyla and could be targeted for discovering a drug that will be specific of a phylum, but not of the others. For example:

(1) in the cyanobacteria, the fourth pseudoknot PK4 is made of two smaller pseudoknots called PK4a and PK4b;

(2) in the mycoplasma, helix H2 is made of only 4 base-pairs instead of 5 in the other species;

(3) for two sequences of chlorobium as well as *Bacteroides thetaiotaomicron* and ppm gingiv., there is an additional domain just downstream of the coding sequence that is unique to them;

(4) there is always a stem-loop in the coding sequence of the actinobacteria (Felden et al., 1999); and (5) all the beta proteobacteria possess a sequence insertion in pseudoknot PK2 (shown in the alignment).

The novel sequences described herein, when aligned, show that specific structural domains within tmRNA are strictly conserved, as for example pseudoknot PK1 is located upstream (at the 5'-side) of the coding sequence. As previously disclosed, this pseudoknot is a target for future anti-bacterial drugs. Moreover, recent data have shown that this PK1 pseudoknot, among all the four pseudoknots within tmRNA gene sequences (sometimes there's only 2 or 3 detectable pseudoknots, depending upon the sequences), is the only one that its correct folding is essential for the biological activity of tmRNA (Nameki et al., 1999; Nameki et al., 2000).

It has recently been discovered that even the alpha-proteobacteria possess tmRNA genes. These genes are permuted and are made in two parts, connected via a processed linker. These tmRNA gene sequences from alpha-proteobacteria were not found in the course of the present invention because usual PCR methods could not amplify them.

Recent reports have shown that whereas the gene encoding tmRNA is non-essential in *E. coli* (does not kill the bacteria when disrupted), it is indeed essential in *Neisseria gonorrheae* (Huang et al., 2000). Also, tmRNA is directly involved in *Salmonella typhymurium* pathogenticity (Julio et al., 2000).

In summary, tmRNA genes are present in all eubacterial genomes, with no exceptions, but are not present in any genomes from archebacteria or eukaryotes, with the exception of some chloroplasts. The very specific location of tmRNA genes within one of the three main kingdoms of life make them ideal targets for the design of novel antibiotics that will, in principle, interfere very weakly with human biochemistry, compared to usual antibiotics. For a recent review about designing novel antibiotics, see Breithaupt (1999).

The present invention is also directed to diagnostic assays and kits for the detection of bacterial infection, particularly infections caused by bacterial agents disclosed herein. In one embodiment, the coding sequence of each bacterial species is used to design specific primers for use in amplification-based diagnostic assays for infectious diseases. Specific primers are designed in accordance with well known techniques, and such design is readily done by a skilled artisan. Amplification-based diagnostic assays are performed in accordance with conventional techniques well known to skilled artisans. Examples of amplification-based assays include, but are not limited to, polymerase chain reaction (PCR) amplification, strand displacement amplification (SDA), ligase chain reaction (LCR) amplification, nucleic acid sequence based amplification (3SR or NASBA) and amplification methods based on the use of Q-beta replicase.

Drugs which target the sequences described herein are active agents can be formulated in pharmaceutical compositions, which are prepared according to conventional pharmaceutical compounding techniques (*Remington's*, 1990). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may dissolved in a pharmaceutical carrier and administered as either a solution of a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in an therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences* (18).

Alternatively, targeting therapies may be used to deliver the active agent more specifically to certain types of cell, by the use of targeting systems such as antibodies or cell-specific ligands. Targeting may be desirable for a variety of reasons, e.g. if the agent is unacceptably toxic, or would otherwise require too high a dosage, or otherwise be unable to enter the target cells.

Antisense active agents can also be delivered by techniques described in U.S. Pat. Nos. 5,811,088; 5,861,290 and 5,767,102.

EXAMPLES

The present invention is further detailed in the following Examples, which are offered by way of illustration and are not intended to limit the invention in any manner. Standard techniques well known in the art or the techniques specifically described below are utilized.

Example 1

Materials and Methods

1. Extraction of Genomic DNA

Bacterial genomic DNAs were prepared from ~10 mg freeze-dried cells provided from ATCC (American Type Culture Collection, Virginia, USA). Cell pellets were resuspended in 750 μL of lysis buffer (50 mM Tris (pH 8.0), 50 mM EDTA and 20% sucrose). 150 μL of a 10 mg/mL solution of lysozyme was mixed and let stand at room temperature for 15 min. 150 μL of 1% SDS was added and let stand at room temperature for 15 minutes. Four to five phenol/chloroform extractions were performed, until the sample was clear and there was no interphase. Two to five μL of a 10 mg/mL solution of RNase DNase-free was added and incubated at room temperature for 30 minutes. After a phenol/chloroform extraction of the enzyme, the genomic DNA was precipitated with 1/10 volume of 3M NaOAc (pH 5.5) and 1 volume isopropanol, and stored at −20° C. for 2 hours. After centrifugation, the genomic DNAs were washed with 70% ethanol, vacuum-dried and diluted in sterile water to a final concentration of 10 ng/μL.

2. Primer Sets for PCR Reactions

The following primer sets were used during the PCR:

primer set A (based on *E. coli* tmRNA termini):

5'-GGG GCT GAT TCT GGA TTC GAC-3' (SEQ ID NO:1) and

5'-TGG AGC TGG CGG GAG TTG AAC-3' (SEQ ID NO:2);

primer set B (based on *T. neapolitana* tmRNA termini):

5'-GGG GGC GGA AAG GAT TCG ACG-3' (SEQ ID NO:3) and

5'-TGG AGG CGG CGG GAA TCG AAC-3' (SEQ ID NO:4);
primer set C (based on *M. pneumoniae* tmRNA termini):
5'-GGG GAT GTC ATG GTT TTG ACA-3' (SEQ ID NO:5) and
5'-TGG AGA TGG CGG GAA TCG AAC-3' (SEQ ID NO:6); and
primer set D (based on *C. tepidum* tmRNA termini):
5'-GGG GAT GAC AGG CTA TCG ACA-3' (SEQ ID NO:7) and
5'-TGG AGA TGG CGG GAC TTG AAC-3' (SEQ ID NO:8).

3. PCR Reaction

Sequences of tmRNA genes were obtained by polymerase chain reaction (PCR) in 25 μL using 40 ng of genomic DNA per reaction. The following general scheme was utilized for all of the sequences:
 (a) 94° C. to 96° C. for 4 min. (first denaturation of genomic DNAs, done only once); then
 (b) 35 to 40 PCR cycles with 2.5 to 5 Units of Taq DNA polymerase in a 25 μL reaction volume, according to the following scheme (40 ng of genomic DNAs/PCR reaction):
  1. denature at 94° to –96° C. for 25 to 30 sec;
  2. anneal at 44° to 55° C. for 20 to 30 sec; and
  3. extension at 72° C. for 10 sec.

The magnesium conc. was optimized for each phyla from 3.5 to 13.5 mM.

4. Elution of Amplified DNAs

The various PCR-amplified tmDNA bands were gel purified (5% PAGE), stained (ethidium bromide staining), cut using a sterile razor blade, and shaken over-night (passive elution, using a vibrator) in a 350 μl solution containing 10 mM Tris-HCl buffer (pH 8.1). The following day, the PCR amplified tmDNAs were ethanol precipitated, washed in 70% ETOH, vacuum dried and the DNA pellets were dissoved in 18 μl of RNase-DNase free sterile water.

5. DNA Sequencing

Six μL of amplified DNAs were added to 3.2 picomoles of the primer that was used in the PCR. To verify the novel tmDNA sequences, each of the two primers were used independently to sequence each of the two PCR-amplified DNA strands. Some tmDNAs were already engineered at their 5'-ends with a T7 promoter, to be able to transcribe directly the tmDNAs into tmRNAs by in vitro transcription.

Dye terminator sequencing was achieved at the DNA sequencing facility of the Human Genetics Institute. In addition to novel tmRNA sequences that are not available publicly, several tmDNA sequences that were already known have been verified and several sequencing mistakes have been found and corrected (especially for *Alcaligenes eutrophus* tmRNA).

Example 2

Amplification Reactions for Eubacterial tmDNA

Eubacterial tmDNA was amplified by PCR in accordance with Example 1, using the following conditions.

Acidobacterium:
 Primer Set B; Annealing temp. during PCR: 53° C. for 20 sec; $Mg^{2+}$ conc.: 4.5 mM.

Coprothermobacter:
 Primer Set B; Annealing temp. during PCR: 55° C. for 30 sec; $Mg^{2+}$ conc.: 5.5 mM.

Cytophagales:
 Primer Set A; Annealing temp. during PCR: 46° C. for 30 sec; $Mg^{2+}$ conc.: 4.5 mM.

Dictyoglomus:
 Primer set B; Annealing temp. during PCR: 55° C. for 30 sec; $Mg^{2+}$ conc.: 4.5 mM.

Environmental Samples:
 Sludge DNA
  Primer set C; Annealing temp. during PCR: 51° C. for 20 sec; $Mg^{2+}$ conc.: 13.5 mM.
 Rumenal Fluid DNA
  Primer set D; Annealing temp. during PCR: 50° C. for 30 sec; $Mg^{2+}$ conc.: 9.5 mM.

Fibrobacter:
 Primer set A; Annealing temp. during PCR: 51° C.; $Mg^{2+}$ conc.: 3.5 mM.

Firmicutes:
 Fusobacteria:
  Primer set A; Annealing temp. during PCR: 52° C.; $Mg^{2+}$ conc.: 5.5 mM.
 High G-C:
  Primer set A; Annealing temp. during PCR: 50–55° C.; $Mg^{2+}$ conc.: 4.5 mM.
 Low G-C:
  Primer sets A or B; Annealing temp. during PCR: 52° C.; $Mg^{2+}$ conc.: 5.5 to 7.5 mM.
 Mycoplasmes:
  Primer set A; Annealing temp. during PCR: 52° C.; $Mg^{2+}$ conc.: 3.5 to 5.5 mM.

Green Non-Sulfur:
 Primer sets A or B; Annealing temp. during PCR: 46 to 52° C.; $Mg^{2+}$ conc.: 4.5 mM.
 Green Sulfur:
  Primer set A; Annealing temp. during PCR: 46° C.; $Mg^{2+}$ conc.: 4.5 mM.

Planctomycetales:
 Primer set A; Annealing temp. during PCR: 48 to 52° C.; $Mg^{2+}$ conc.: 7.5 mM.

Proteobacteria:
 Beta:
  Primer sets A and/or B; Annealing temp. during PCR: 50° C. for 25 sec; $Mg^{2+}$ conc.: 3.5 mM.
 Delta:
  Primer set B; Annealing temp. during PCR: 55° C.; $Mg^{2+}$ conc.: 3.5 to 4.5 mM.
 Epsilon:
  Primer set A; Annealing temp. during PCR: 46° C. for 30 sec; $Mg^{2+}$ conc.: 3.5 mM.
 Gamma:
  Primer set A; Annealing temp. during PCR: 44 C for 30 sec; $Mg^{2+}$ conc.: 5.5 mM.

Spirochetes:
 Primer set A; Annealing temp. during PCR: 52° C.; $Mg^{2+}$ conc.: 4.5 mM.

Thermodesulfobacterium:
 Primer set B; Annealing temp. during PCR: 55° C.; $Mg^{2+}$ conc.: 5.5 mM.

Thermotogales:
 Primer set B; Annealing temp. during PCR: 46° C.; $Mg^{2+}$ conc.: 7.5 mM.

Deinococcales:
 Primer set B; Annealing temp. during PCR: 52° C.; $Mg^{2+}$ conc.: 3.5 mM.

Verrucomicrobia:
 Primer set A; Annealing temp. during PCR: 53° C. for 25 sec; $Mg^{2+}$ conc.: 3.5 mM.

Example 3

Amplification of Eubacterial tmDNA

Figures 1, 7A:
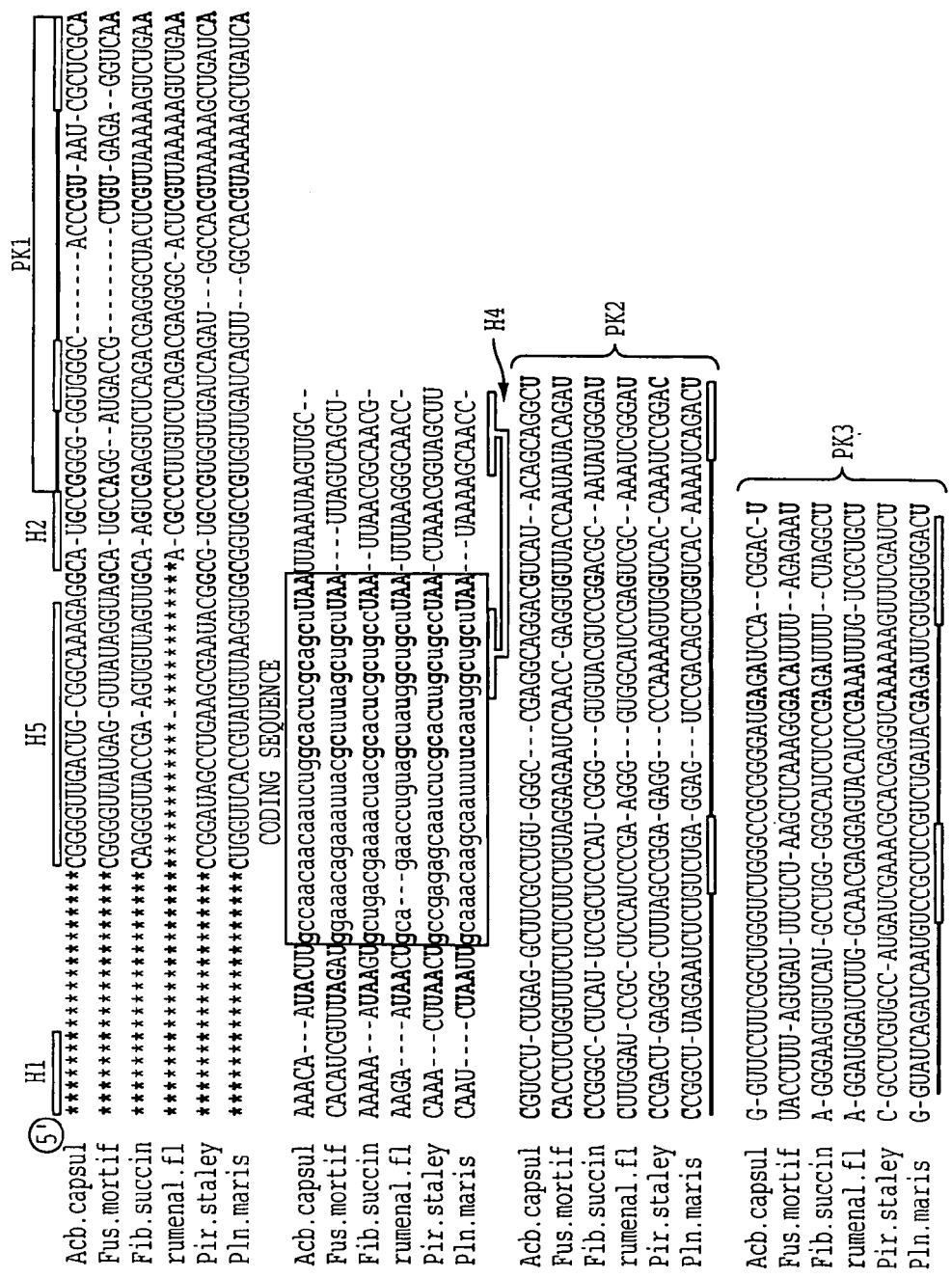
Figure 7C:
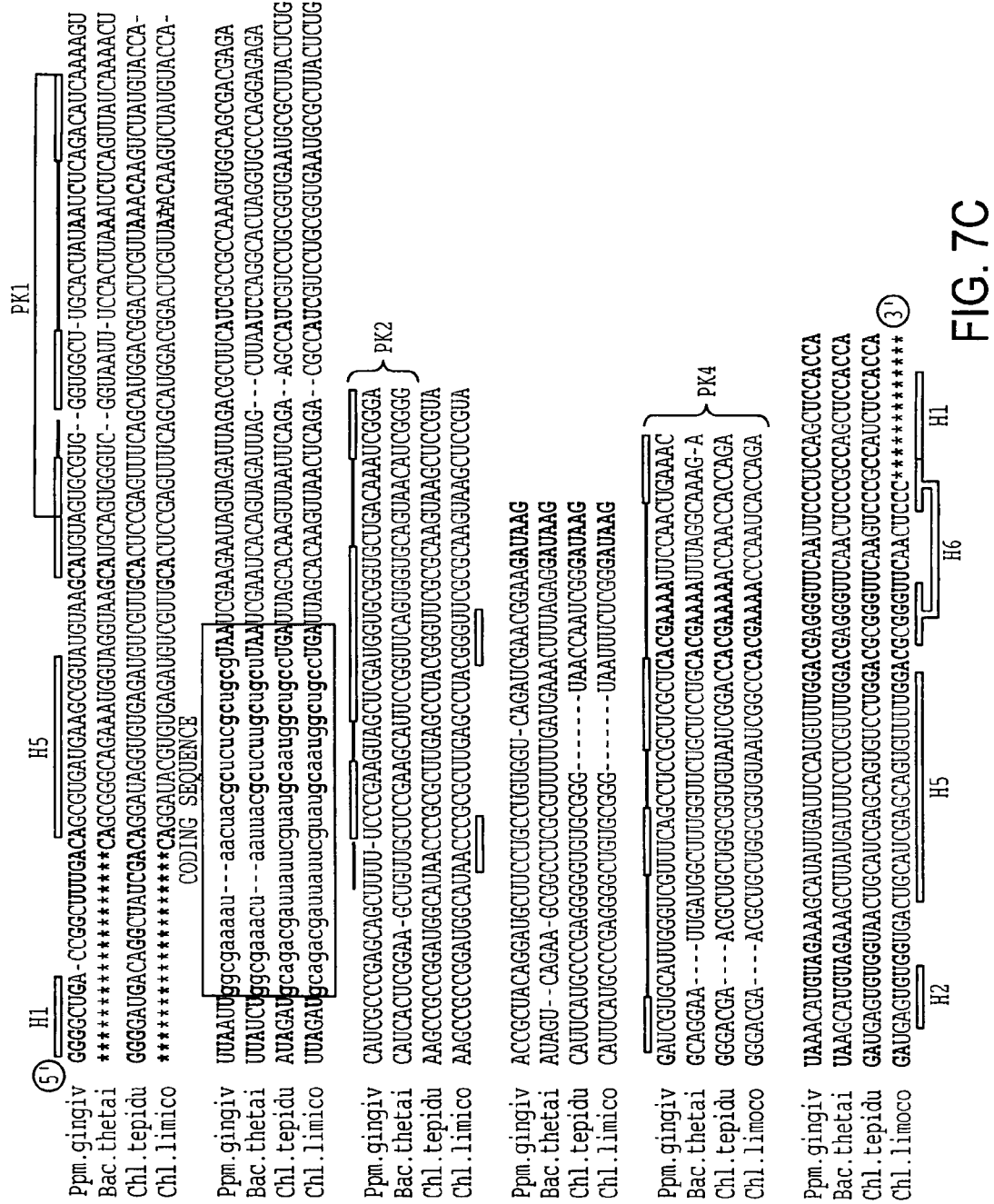
Figure 8A:
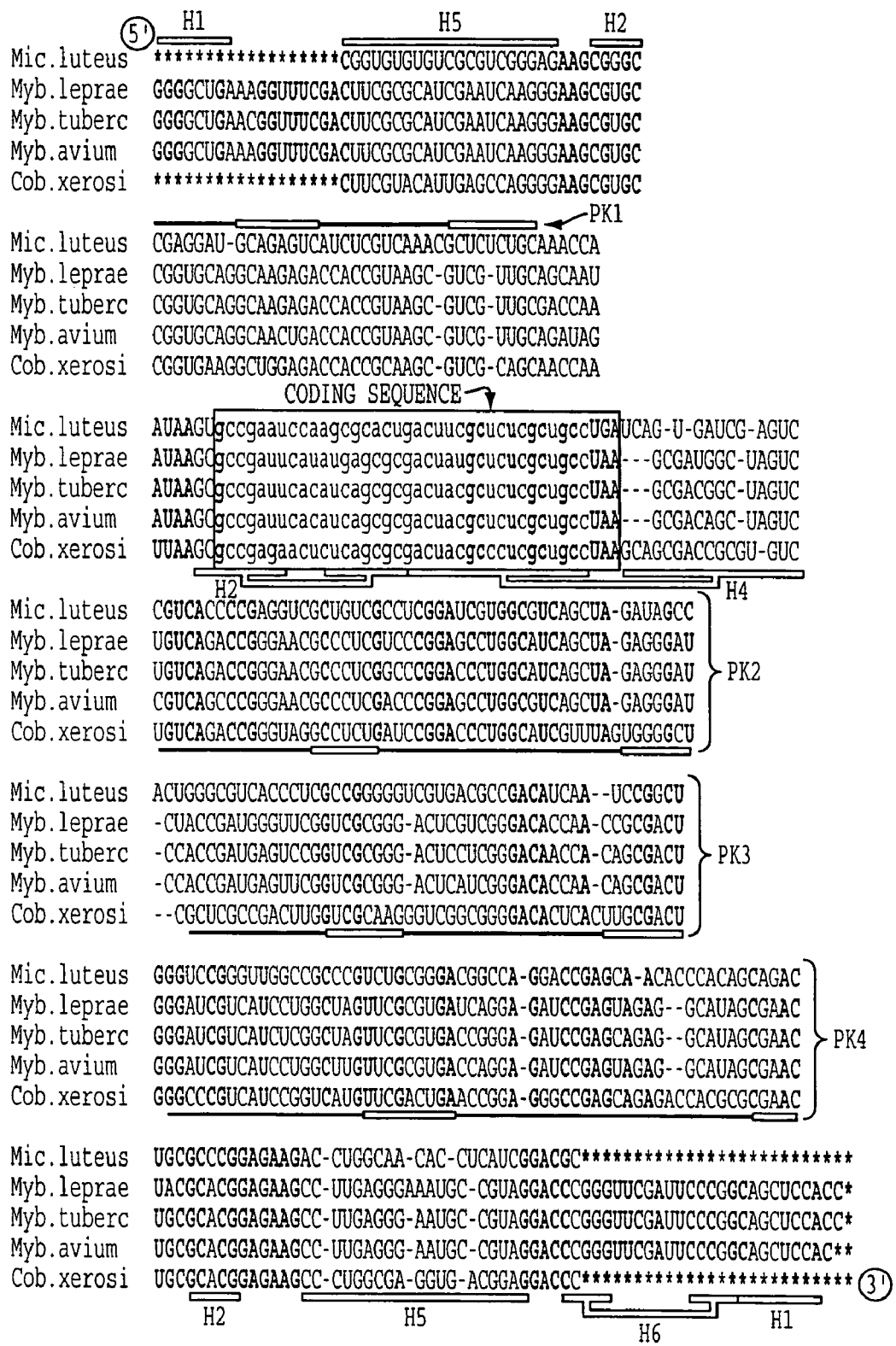
FIGS. 8A and 8B show the sequence alignment, structural domains and structural features for the tmRNA of several species of Actinobacteries (8A) and Spirochaetes (8B). The tmRNA sequences of the Actinobacteries are set forth in SEQ ID NOs:132–136, and the tmRNA sequences of the Spirochaetes are set forth in SEQ ID NOs:137–142.
Figure 8B:
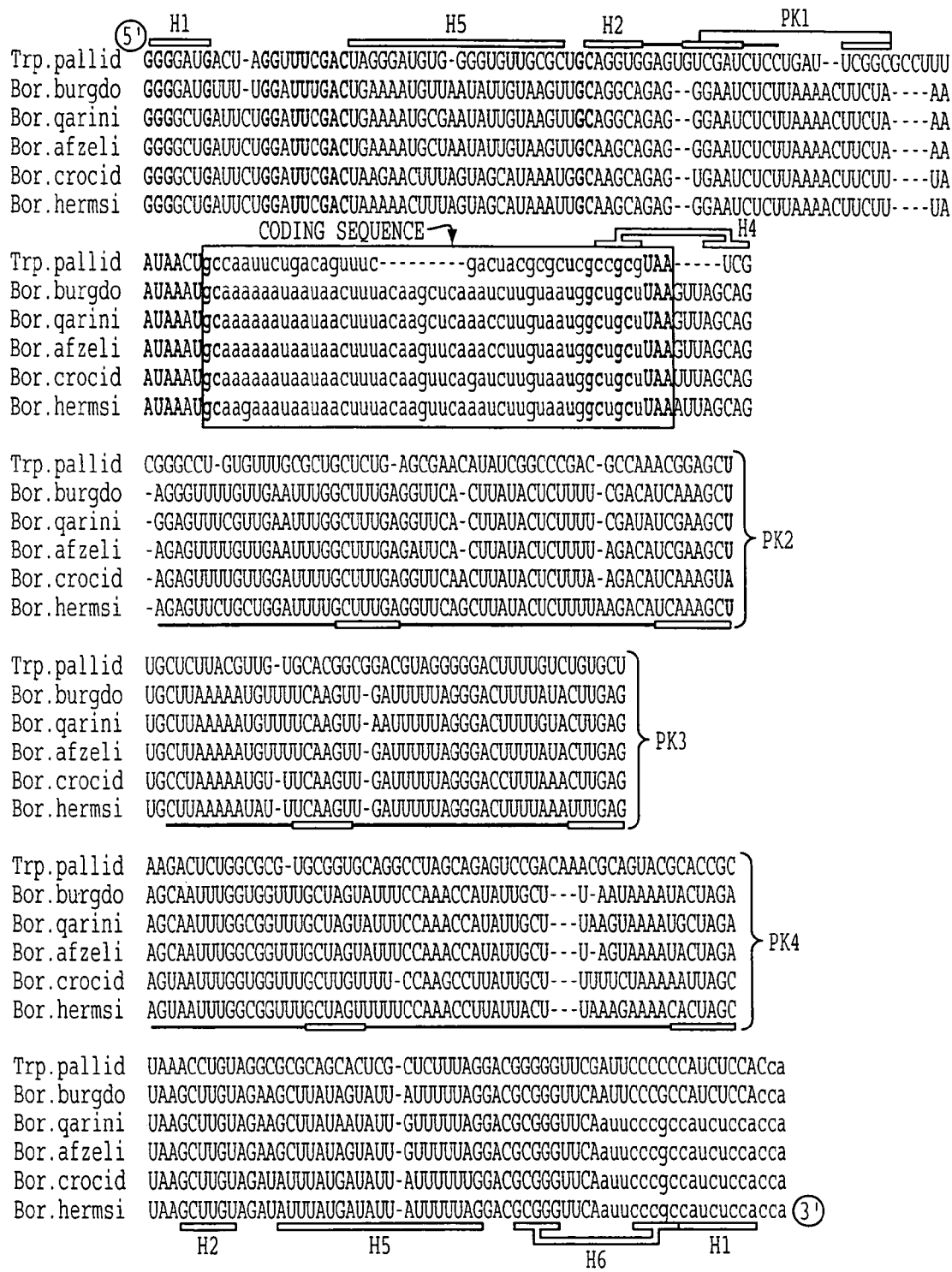
Figure 9A:
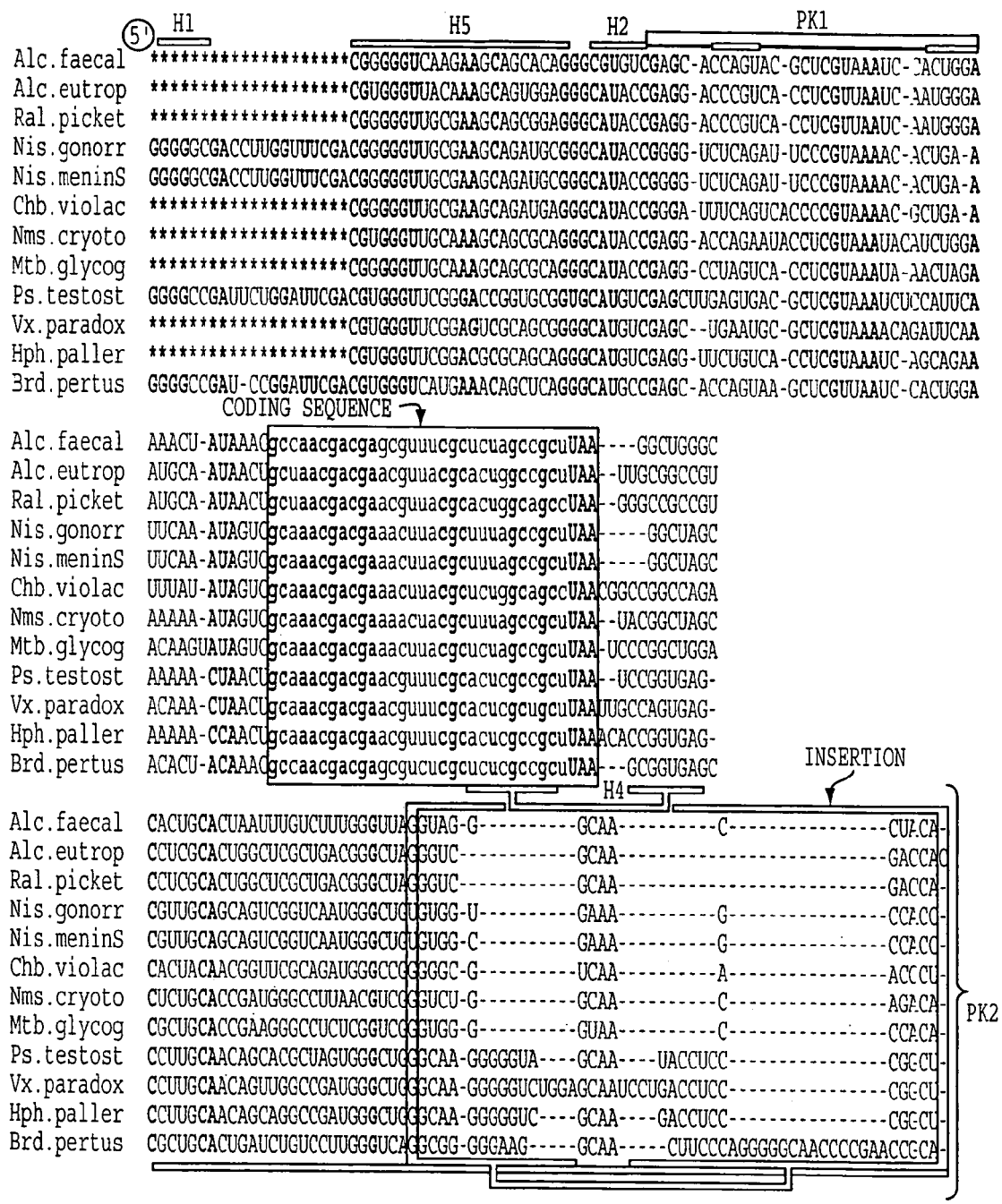
Figure 11A:
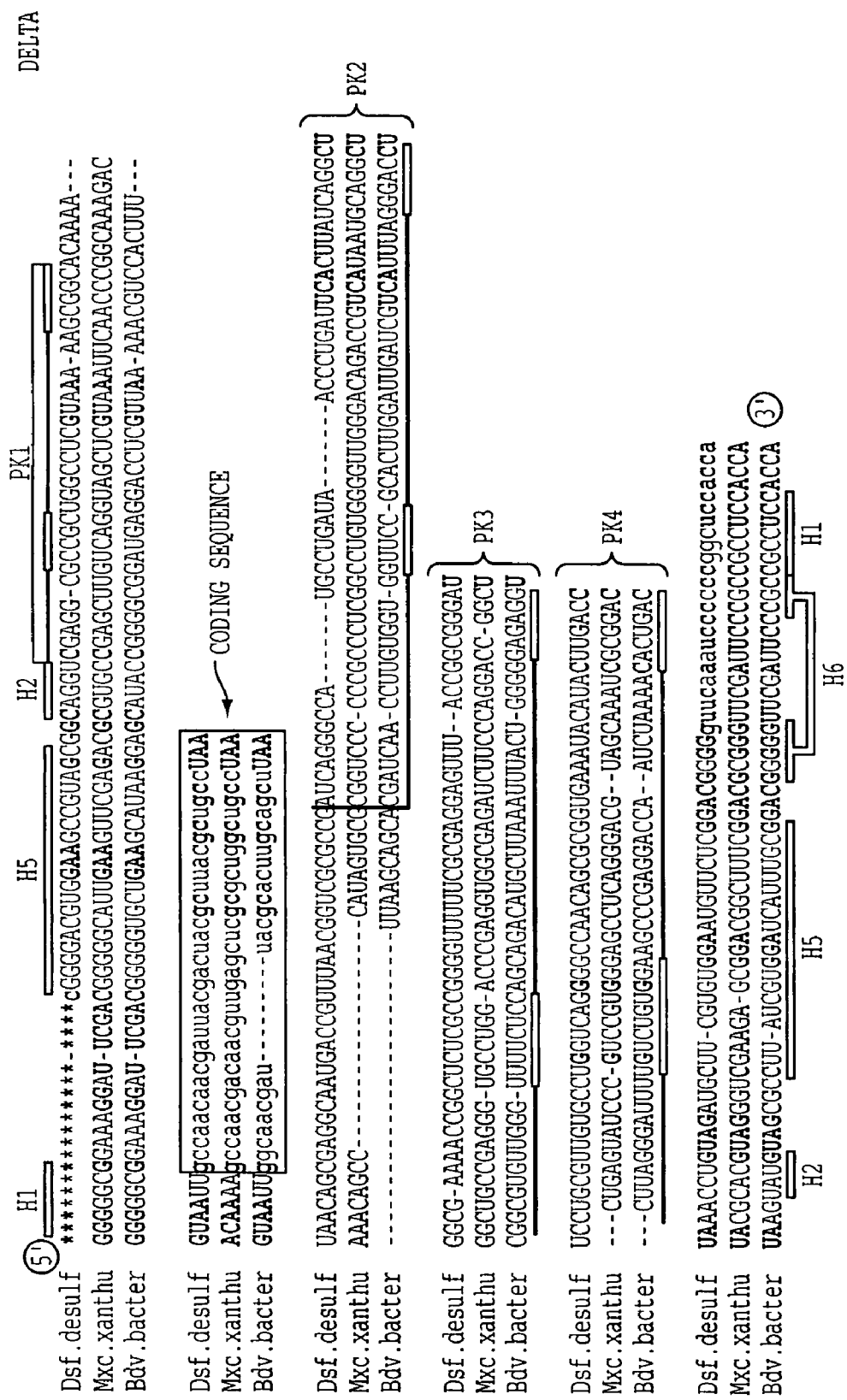
FIGS. 11A and 11B show the sequence alignment, structural domains and structural features for the tmRNA of several species of Pourpres delta (11A) and Pourpres epsilon (11B). The tmRNA sequences of the Pourpres delta are set forth in SEQ ID NOs:170–172, and the tmRNA sequences of the Pourpres epsilon are set forth in SEQ ID NOs: 173–175.
Figure 11B:
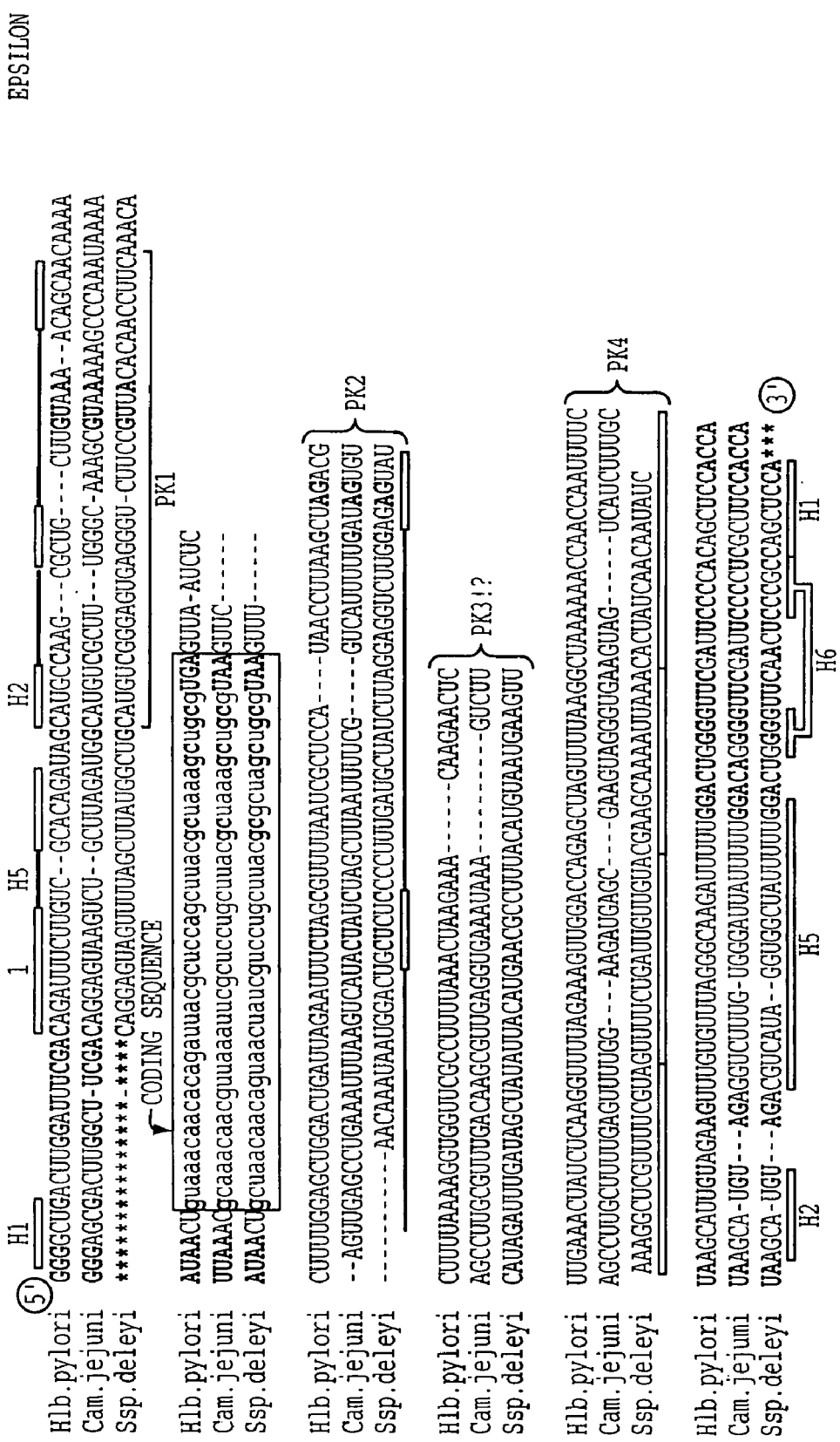

Specific PCR amplification of tmRNA genes was achieved for both thermophilic and mesophilic eubacterial tmRNA genes. For the novel tmDNA genes found in thermophiles, both the magnesium concentration and the annealing temperature (FIG. 1A) were optimized. As shown in FIG. 1A, a specific amplification of *Thermus aquaticus* tmDNA was observed with an annealing temperature around 50° C., whereas at higher temperatures there is a gradual decrease in the amount of amplified tmDNA. For mesophiles, the magnesium concentration during PCR was critical (FIG. 1B), but the annealing temperature could vary from 44° C. to 60° C. without significant effects on the amplification. FIG. 1B shows various effects of increasing the magnesium concentration on the PCR amplification of three novel eubacterial tmDNA genes. Increasing magnesium concentration from 3.5 mM to 5.5 mM has either a negative (FIG. 1B, panel 1), a positive (FIG. 1B, panel 2) or no effect on specifically amplifying eubacterial tmDNA genes.

According to these procedures, tmRNA genes from many eubacteria including known human pathogens were amplified. The PCR was facilitated by sequence conservation at both 5' and 3' ends and was performed as described (Williams and Bartel, 1996), with modifications. This study was initiated to collect further sequences from eubacterial tmDNA genes, as well as to test experimentally whether tmDNA genes could be found in all bacterial phyla or subgroups. 51 new tmDNA sequences were determined (FIG. 2), including sequences from members of 8 additional phyla and 1 subgroup (shaded boxes in FIG. 2). The 58 new tmDNA sequences are set forth in Tables 1–58. This brings coverage to a total of 104 sequences in 19 bacterial phyla. Interestingly, tmDNA sequences could be amplified from all species tested apart from those in the alpha-Proteobacteria. Five genomic DNAs from alpha-Proteobacteria (*Agrobacterium tumefaciens, Bartonella henselae, Bartonella quintana, Rhodospirillum rubrum* and *Rickettsia prowazekii*) were extensively checked using various oligonucleotides, annealing temperatures and magnesium concentrations. No specific amplified tmDNA sequences were detected in this subgroup. Moreover, no putative tmDNA sequences could be identified (results herein and Williams, 1999) by Blast searches on the 1 fully sequenced (*Rickettsia prowazekii*) and 2 nearly completed (*Caulobacter crescentus* and *Rhodobacter capsulatus*) alpha-proteobacterial genomes (FIG. 2).

It cannot be ruled out that tmDNA sequences may have largely diverged in the alpha-proteobacterial sub-group compared to other bacterial phyla, and that both PCR methods and Blast searches are missing the relevant sequences. While tmRNA is dispensable in *E. coli* (Ando et al., 1996), it is striking that it has been found in all bacteria tested other than the alpha-Proteobacteria. The alpha-Proteobacteria have undergone reductive evolution. This has been more intensive in one of the two sub-classes than in the other (Gray and Spencer, 1996), but tmRNA sequences have not been found even in the sub-class with the larger genome. Based on sequence comparison, the alpha-Proteobacteria and mitochondria are evolutionary relatives (Yang et al., 1985; Andersson et al., 1998). The drastic downsizing in what has become mitochondrial genomes means that it is not reasonable to draw inferences on the relationship between alpha-Proteobacteria and mitochondria based on their mutual apparent absence of tmRNA. It is nevertheless, of interest, that at least some chloroplasts and cyanelle genomes have tmDNA sequences, and the cyanobacteria, with which they are evolutionary related, also have tmRNA.

TABLE 1 tmDNA Sequence for *Acidobacterium capsulatum* (Acidobacterium)

(SEQ ID NO:9)

GGGGGCGGAAAGGATTCGACGGGGTTGACTGCGGCAAAGAGGCATGCCGGGGGTGGGCACCCG

TAATCGCTCGCAAAACAATACTTGCCAACAACAATCTGGCACTCGCAGCTTAATTAAATAAGTT

GCCGTCCTCTGAGGCTTCGCCTGTGGGCCGAGGCAGGACGTCATACAGCAGGCTGGTTCCTTCG

GCTGGGTCTGGGCCGCGGGGATGAGATCCACGGACTAGCATTCTGCGTATCTTGTCGCTTCTAA

GCGCAGAGTGCGAAACCTAAAGGAATGCGACTGAGCATGGAGTCTCTTTTCTGACACCAATTTC

GGACGCGGGTTCGATTCCCGCCGCCTCCACCA

TABLE 2 tmDNA Sequence for *Coprothermobacter proteolyticus* (60 degrees)

(SEQ ID NO:10)

GGGGGCGGAAAGGATTCGACGGGGAGTCGGAGCCTTGAGCTGCAGGCAGGGTTGGCTGCCACAC

CTTAAAAAGGGTAGCAAGGCAAAAATAAATGCCGAACCAGAATTTGCACTAGCTGCTTAATGTA

AGCAGCCGCTCTCCAAACTGAGGCTGCATAAGTTTGGAAGAGCGTCAACCCATGCAGCGGCTCT

TABLE 2-continued tmDNA Sequence for *Coprothermobacter proteolyticus* (60 degrees)

TAAGCAGTGGCACCAGCTGTTTAAGGGTGAAAAGAGTGGTGCTGGGCAGTGCGGTTGGGCTTCC

TGGGCTGCACTGTCGAGACTTCACAGGAGGGCTAAGCCTGTAGACGCGAAAGGTGGCGGCTCGT

CGGACGCGGGTTCGATTCCCGCCGCCTCCACCA

TABLE 3 tmDNA Sequence for *Bacteroides thetaiotaomicron* (bacteroides/flavobacterium)

(SEQ ID NO:11)

GGGGCTGATTCTGGATTCGACAGCGGGCAGAAATGGTAGGTAAGCATGCAGTGGGTCGGTAATT

TCCACTTAAATCTCAGTTATCAAAACTTTATCTGGCGAAACTAATTACGCTCTTGCTGCTTAAT

CGAATCACAGTAGATTAGCTTAATCCAGGCACTAGGTGCCAGGACGAGACATCACTCGGAAGCT

GTTGCTCCGAAGCATTCCGGTTCAGTGGTGCAGTAACATCGGGGATAGTCAGAAGCGGCCTCGC

GTTTTTGATGAAACTTTAGAGGATAAGGCAGGAATTGATGGCTTTGGTTCTGCTCCTGCACGAA

AATTTAGGCAAAGATAAGCATGTAGAAAGCTTATGATTTCCTCGTTTGGACGAGGGTTCAACTC

CCGCCAGCTCCACCA

TABLE 4 tmDNA Sequence for *Dictyoglomus thermophilum* (70 degrees)

(SEQ ID NO:12)

GGGGCTGATTCTGGATTCGACAGGGAGTACAAGGATCAAAAGCTGCAAGCCGAGGTGCCGTTAC

CTCGTAAAACAACGGCAAAAAAGAAGTGCCAACACAAATTTAGCATTAGCTGCTTAATTTAGCA

GCTACGCTCTTCTAACCCGGGCTGGCAGGGTTAGAAGGGTGTCATAATGAGCCAGCTGCCCCTT

CCGACTCCCCTAAGGAAGGGAAAGATGTAGGGGATAGGTGCTTACAGAATCCTGCGGGAGGGAG

TCTGTAAGTGCCGAAAAGTTAAAACTCCCGCTAAGCTTGTAGAGGCTTTTGATTCTTGCTCTCT

GGACGCGGGTTCAACTCCCGCCAGCTCCACCA

TABLE 5 tmDNA Sequence for Environmental Sample from Rumenal Fluid (SEQ ID NO:13)

ACGCCCTTGTCTCAGACGAGGGCACTCGTTAAAAAGTCTGAAAAGAATAACTGCAGAACCTGTA

GCTATGGCTGCTTAATTTAAGGGCAACCCTTGGATCCGCCTCCATCCCGAAGGGGTGGCATCCG

AGTCGCAAATCGGGATAGGATGGATCTTGGCAACGAGGAGTACATCCGAAATTTGTCGCTGCTG

GCTGAAGCATCGCCGTTCCTCTTTGGGCGTGGCAAGGCAAGATTAAATTCAGAGGATAAGCGTG

TAGTAGCGAGTGAGTAGGTGTTTTTGGACGCGGGTTCAAGTCCCGCCATCTCCACCA

TABLE 6 tmDNA Sequence for Environmental Sample from Sludge (SEQ ID NO:14)

GGGGATGTCATGGTTTTGACAGGGAACCAGGAGGTGTGAGATGCATGCCGGAGACGCTGTCCGC

TCCGTTATCAAGCAGCAAACAAAACTAATTGCAAACAACAATTACTCCTTAGCAGCGTAAGCAG

CTAACGTTCAACCTCTCCGGACCGCCGGGAGGGGATTTGGGCGTCGAAACAGCGCGGACGCTCC

TABLE 6-continued tmDNA Sequence for Environmental Sample from Sludge

GGATAGGACGCCCATAATATCCGGCTAAGACCATGGGTCTGGCTCTCGCGGGTCTGATTGTCTT

CCACCGCGCGGGCCGCGATCAAAGACAACTAAGCATGTAGGTTCTTGCATGGCCTGTTCTTTGG

ACGCGGGTTCGATTCCCGCCATCTCCACCA

TABLE 7 tmDNA Sequence for *Fibrobacter succinogenes* (*Fibrobacter*)

(SEQ ID NO:15)
GGGGCTGATTCTGGATTCGACAGGGTTACCGAAGTGTTAGTTGCAAGTCGAGGTCTCAGACGAG

GGCTACTCGTTAAAAAGTCTGAAAAAAAATAAGTGCTGACGAAAACTACGCACTCGCTGCCTAA

TTAACGGCAACGCCGGGCCTCATTCCGCTCCCATCGGGGTGTACGTCCGGACGCAATATGGGAT

AGGGAAGTGTCATGCCTGGGGGCATCTCCCGAGATTTTCTAGGCTGGTCAAACTCCGCGCCGAC

CTTCTTGGGCGTGGATAAGACGAGATCTTAAATTCGAAGGGAACACTTGTAGGAACGTACATGG

ACGTGATTTTGGACAGGGGTTCAACTCCCGCCAGCTCCA

TABLE 8 tmDNA Sequence for *Fusobacterium mortiferum*

(SEQ ID NO:16)
GGGGCTGATTCTGGATTCGACGGGGTTATGAGGTTATAGGTAGCATGCCAGGATGACCGCTGTG

AGAGGTCAACACATCGTTTAGATGGAAACAGAAATTACGCTTTAGCTGCTTAATTAGTCAGCTC

ACCTCTGGTTTCTCTCTTCTGTAGGAGAATCCAACCGAGGTGTTACCAATATACAGATTACCTT

TAGTGATTTCTCTAAGCTCAAAGGGACATTTTAGAGAATAGCTTCAGTTAGCCCTGTCTGCGGG

AGTGATTGTTGCGAAATAAAATAGTAGACTAAGCATTGTAGAAGCCTATGGCGCTGGTAGTTTC

GGACACGGGTTCAACTCCCGCCAGCTCCAA

TABLE 9 tmDNA Sequence for *Corynebacterium xerosis* (gram +, high G-C content)

(SEQ ID NO:17)
GGGGCTGATTCTGGATTCGACTTCGTACATTGAGCCAGGGGAAGCGTGCCGGTGAAGGCTGGAG

ACCACCGCAAGCGTCGCAGCAACCAATTAAGCGCCGAGAACTCTCAGCGCGACTACGCCCTCGC

TGCCTAAGCAGCGACCGCGTGTCTGTCAGACCGGGTAGGCCTCTGATCCGGACCCTGGCATCGT

TTAGTGGGGCTCGCTCGCCGACTTGGTCGCAAGGGTCGGCGGGGACACTCACTTGCGACTGGGC

CCGTCATCCGGTCATGTTCGACTGAACCGGAGGGCCGAGCAGAGACCACGCGCGAACTGCGCAC

GGAGAAGCCCTGGCGAGGTGACGGAGGACCCGGGTTCAACTCCCGCCAGCTCCACCA

TABLE 10 tmDNA Sequence for *Micrococcus luteus* (parfait)

(SEQ ID NO:18)
GGGGCTATTCTGGATTCGACGGTGTGTGTCGCGTCGGGAGAAGCGGGCCGAGGATGCAGAGTCA

TCTCGTCAAACGCTCTCTGCAAACCAATAAGTGCCGAATCCAAGCGCACTGACTTCGCTCTCGC

TGCCTGATCAGTGATCGAGTCCGTCACCCCGAGGTCGCTGTCGCCTCGGATCGTGGCGTCAGCT

TABLE 10-continued tmDNA Sequence for *Micrococcus luteus* (parfait)

AGATAGCCACTGGGCGTCACCCTCGCCGGGGGTCGTGACGCCGACATCAATCCGGCTGGGTCCG

GGTTGGCCGCCCGTCTGCGGGACGGCCAGGACCGAGCAACACCCACAGCAGACTGCGCCCGGAG

AAGACCTGGCAACACCTCATCGGACGCGGGTTCAACTCCCGCANTCCCACCA

TABLE 11 tmDNA Sequence for *Mycobacterium smegmatis*

(SEQ ID NO:19)
TCATCTCGGCTTGTTCGCGTGACCGGGAGATCCGAGTAGAGACATAGCGAACTGCGCACGGAGA

GGGGCTGATTCCTGGATTCGACTTCGAGCATCGAATCCAGGGAAGCGTGCCGGTGCAGGCAAGA

GACCACCGTAAGCGTCGTTGCAACCAATTAAGCGCCGATTCCAATCAGCGCGACTACGCCCTCG

CTGCCTAAGCGACGGCTGGTCTGTCAGACCGGGAGTGCCCTCGGCCCGGATCCTGGCATCAGCT

AGAGGGACCCACCCACGGGTTCGGTCGCGGGACCTGTGGGACATCAAACAGCGACTGGGATCG

AGCCTCGAGGACATGCCGTAGGACCCGGGTTCAACTCCCGCCAGCTCCACCA

TABLE 12 tmDNA Sequence for *Bacillus badius*

(SEQ ID NO:20)
GGGGGTGATTCTGGATTCGACAGGGATAGTTCGAGCTTGGGCTGCGAGCCGGAGGGCCGTCTTC

GTACCAACGCAAACGCCTAAATATAACTGGCAAAAAAGATTTAGCTTTAGCTGCCTAATATAGG

TTCAGCTGCTCCTCCCGCTATCGTCCATGTAGTCGGGTAAGGGGTCCAAACTTAGTGGACTACG

CCGGAGTTCTCCGCCTGGGGACAAAGGAAGAGATCAATCAGGCTAGCTGCCCGGACGCCCGTCG

ATAGGCAAAAGGAACAGTGAACCCCAAATATATCGACTACGCTCGTAGACGTTCAAGTGGCGTT

ATCTTTGGACGTGGGTTCAACTCCCGCCAGCTCCA

TABLE 13 tmDNA Sequence for *Bacillus brevis*

(SEQ ID NO:21)
GGGGGCGGAAAGGATTCGACGGGGATGGTAGAGCATGAGAAGCGAGCCGGGGGGTTGCGGACCT

CGTCACCAACGCAAACGCCATTAACTGGCAACAAACAACTTTCTCTCGCTGCTTAATAACCAGT

GAGGCTCTCCCACTGCATCGGCCCGTGTGCCGTGGATAGGGCTCAACTTTAACGGGCTACGCCG

GAGGCTTCCGCCTGGAGCCAAAGGAAGAAGACCAATCAGGCTAGGTGCCAGGTCAGCGCGTCAC

TCCGCGAATCTGTCACCGAAACTCTAAACGAGTGACTGCGCTCGGAGATGCTCATGTATCGCTG

TTTTCGGACGGGGGTTCGATTCCCGCCGCCTCACCCA

TABLE 14 tmDNA Sequence for *Bacillus thermoleovorans* (50—60 degres)

(SEQ ID NO:22)
GGGGGCGGAAAGGATTCGACGGGGGTAGGTCGAGCTTAAGCGGCGAGCCGAGGGGGACGTCCTC

GTAAAAACGTCACCTAAAGATAACTGGCAAACAAAACTACGCTTTAGCTGCCTAATTGCTGCAG

CTAGCTCCTCCCGCCATCGCCCGCGTGGCGTTCGAGGGGCTCATATGGAGCGGGCTACGCCCAA

TABLE 14-continued

| tmDNA Sequence for *Bacillus thermoleovorans* (50–60 degres) |
|---|
| ATCCGCCGCCTGAGGATGAGGGAAGAGACGAATCAGGCTAGCCGCCGGGAGGCCTGTCGGTAGG |
| CGGAACGGACGGCGAAGCGAAATATACCGACTACGCTCGTAGATGCTTAAGTGGCGATGCCTCT |
| GGACGTGGGTTCGATTCCCGCCGCCTCCCCACCA |

TABLE 15

| tmDNA Sequence for *Clostridium innocuum* |
|---|
| (SEQ ID NO:23) |
| GGGGGCGGAAAGGATTCGACGGGGATATGTCTGGTACAGACTGCAGTCGAGTGGTTACGTAATA |
| ACCAATTAAATTTAAACGGAAAAACTAAATTAGCTAACCTCTTTGGTGGAAACCAGAGAATGGC |
| TTTCGCTGCTTAATAACCGATATAGGTTCGCAGCCGCCTCTGCATGCTTCTTCCTTGACCATGT |
| GGATGTGCGCGTAAGACGCAAGGGATAAGGAATCTGGTTTGCCTGAGATCAGATTCACGAAAAT |
| TCTTCAGGCACATTCATCAGCGGATGTTCATGACCTGCTGATGTCTTAATCTTCATGGACTAAA |
| CTGTAGAGGTCTGTACGTGGGGCTGTTTCTGGACAGGAGTTCGATTCCCGCCGCCTCACCACCA |

TABLE 16

| tmDNA Sequence for *Clostridium lentocellum* |
|---|
| (SEQ ID NO: 24) |
| GGGGGCGGAAAGGATTCGACGGGGGTCACATCTACTGGGGCAGCCATCCGTAGAACGCCGGAGT |
| CTACGTTAAAAGCTGGCACTTAAAGTAAACGCTGAAGATAATTTAGCAATCGCTGCCTAATTAA |
| GGCGCAGTCCTCCTAGGTCTTCCGCAGCCTAGATCAGGGCTTCGACTCGCGGATCCTTCACCTG |
| GCAAAGCTTTGAGCCAACGTGAACACTATGAAGCTACTAAAATCTAGAGCCTGTCTTTGGGCGC |
| TAGATGGAGGGAATGTCAAAACAAAGAATATGATGGTAGAGACCACGCTATATGGGCTTTCGGA |
| CAGGGGTTCGATTCCCGCCGCCTTCACCA |

TABLE 17

| tmDNA Sequence for *Clostridium perfringens* |
|---|
| (SEQ ID NO: 25) |
| GGGGCTGATTCTGGATTCGACGGGGGTAAGATGGGTTTGATAAGCGAGTCGAGGGAAGCATGGT |
| GCCTCGATAATAAAGTATGCATTAAAGATAAACGCAGAAGATAATTTTGCATTAGCAGCTTAAT |
| TTAGCGCTGCTCATCCTTCCTCAATTGCCCACGGTTGAGAGTAAGGGTGTCATTTAAAAGTGGG |
| GAACCGAGCCTAGCAAAGCTTTGAGCTAGGAACGGAATTTATGAAGCTTACCAAAGAGGAAGTT |
| TGTCTGTGGACGTTCTCTGAGGGAATTTTAAAACACAAGACTACACTCGTAGAAAGTCTTACTG |
| GTCTGCTTTCGGACACGGGTTCAACTCCCGCCACTCCA |

TABLE 18

| tmDNA Sequence for *Clostridium stercorarium* |
|---|
| (SEQ ID NO: 26) |
| GGGGGCGGAAAGGATTCGACGGGGTTATTGAAGCAAGAGTAGCGGGTAGAGGATTCTCGTTGGC |
| CTCTTTAAAAAACGAGAGCTAAAAATAAACGCAAACAACGATAACTACGCTTTAGCTGCTGCGT |
| AAGTAACACGCAGCCCGTCGGCCCCGGGGTTCCTGCGCCTCGGGATACCGGCGTCATCAAGGCA |

TABLE 18-continued tmDNA Sequence for *Clostridium stercorarium*

GGGAACCAGCCGGATCAGGCTTCAGGTCCGGTGGGATTTAATGAAGCTACCGACTTATAAAGCC

TGTCTCTGGGCGTTATAAGAAGGGAATGTCAAAACAGAGACTGCACCCGGAGAAGCTCTTGTGG

ATATGGTTCCGGACACGAGTTCGATTCCCGCCGCCTCCACCA

TABLE 19 tmDNA Sequence for *Enterococcus faecium* (sp.)

(SEQ ID NO: 27)
GGGGCTGATTATGGATTCGACAGGATNGTTGAGCTTGAATTGCGTTTCGTAGGTTACGGCTACG

TTAAAACGTTACAGTTAAATATAACTGCTAAAAACGAAAACAATTCTTTCGCTTTAGCTGCCTA

AAAACCAGCTAGCGAAGATCCTCCCGGCATCGCCCATGTGCTCGGGTCAGGGTCCTAATCGAAG

TGGGATACGCTAAATTTTTCCGTCTGTAAAATTTAGAGGAGCTTACCAGACTAGCAATACAAGA

ATGCCTGTCACTCGGCACGCTGTAAAGCGAACCTTTAAATGAGTGTCTATGAACGTAGAGATTT

AAGTGGGAATATGTTTTGGACGCGGGTTCAACTCCCGCCAGCTCCACCA

TABLE 20 tmDNA Sequence for *Heliobacillus mobilis* (photosyn/gram +)

(SEQ ID NO: 28)
GGGGCTGATTCTGGATTCGACGGGGAACGTGTTTGCTTGGGATGCGAGCCGGGTTGCCGCCAGG

ACCGTAAAAAGGGCGGAAGGCTTTAATTGCCGAAGATAACTACGCTTTAGCTGCTTAATTGCAG

TCTAACCTCTTCTCCTCTGTGCTCTCGGTGAGGATGTAAGGGGTCATTTAAGAGAGCTGGCTTC

GACCAATTCTCGGAGGTCCAAGCGAGATTTATCGAGATAGCCTGACCAACGCTCTGTCTGCCGT

GCGGAAGGAAGGCGAAATCTAAAACGACAGACTACGCTCGTAGTGTCCTTTGTGGGCATTTCTT

CGGACGCGGGTTCAACTCCCGCCAGCTCCACCA

TABLE 21 tmDNA Sequence for *Heliospirillum gestii*

(SEQ ID NO: 29)
GGGGCTGATTCTGGATTCGACGGGGAACGTGTTTGCTTAGGACGCGAGCCGGGTTGCCGCCAGG

ACCGTAAAAAGGGCGGAAGGCTTTAATTGCCGAAGATAACTACGCTTTAGCTGCTTAATTGCAG

TCTAACCTCTTCTCCTCTGTGCTCTCGGTGAGGATGTAAGGGGTCATTTAAGAGAGCTGGCTCG

AACCAATTCTCGGAGGTTCGGGTAAGACTTATCGAGATAGCCTGACCAACGCTCTGTCTGCCGT

GCGGAAGGATGGCGAAATCTAAAACGACAGAATACGCTCGTAGTGTCCTTTGTGGGCATTTCTT

CGGACGCGGGTTCAACTCCCGCCAGCTCCACCA

TABLE 22 tmDNA Sequence for *Lactobacillus acidophilus*

(SEQ ID NO: 30)
GGGGCTGATTCTGGATTCGACAGGCGTAGACCCGCATTGACTGCGGTTCGTAGGTTACGTCTAC

GTAAAAACGTTACAGTTAAATATAACTGCAAATAACAAAAATTCTTACGCATTAGCTGCTTAAT

TTAGCGCATGCGTTGCTCTTTGTCGGTTTACTCGTGGCTGACACTGAGTATCAACTTAGCGAGT

TABLE 22-continued tmDNA Sequence for *Lactobacillus acidophilus*

TACGTTTAACTACCTCACCTGAATAGTTGAAAAGAGTCTTAGCAGGTTAGCTAGTCCATACTAG

CCCTGTTATATGGCGTTTTGGACTAGTGAAGTTCAAGTAATATAACTATGATCGTAGAGGTCAG

TGACGAGATGCGTTTGGACAGCGGGTTCAACTCCCGCCAGCTCCACCA

TABLE 23 tmDNA Sequence for *Staphylococcus epidermidis*

(SEQ ID NO: 31)
GGGGCTGATTCTGCATTCGACAGGGGTCCCCGAGCTTATTAAGCGTGTGGAGGGTTGGCTCCGT

CATCAACACATTTCGGTTAAATATAACTGACAAATCAAACAATAATTTCGCAGTAGCTGCGTAA

TAGCCACTGCATCGCCTAACAGCATCTCCTACGTGCTGTTAACGCGATTCAACCCTAGTAGGAT

ATGCTAAACACTGCCGCTTGAAGTCTGTTTAGATGAAATATAATCAAGCTAGTATCATGTTGGT

TGTTTATTGCTTAGCATGATGCGAAAATTATCAATAAACTACACACGTAGAAAGATTTGTATCA

GGACCTCTGGACGCGGGTTCAACTCCCGCCAGCTCCACCA

TABLE 24 tmDNA Sequence for *Streptococcus faecium*

(SEQ ID NO: 32)
GGGGCTGATTCTGGATTCGACAGGCACAGTTTGAGCTTGAATTGCGTTTCGTAGGTTACGTCTA

CGTTAAAACGTTACAGTTAAATATAACTGCTAAAAACGAAAACAACTCTTACGCTTTAGCTGCC

TAAAAACAGTTAGCGTAGATCCTCTCGGCATCGCCCATGTGCTCGAGTAAGGGTCTCAAATTTA

GTGGGATACGTGACAACTTTCCGTCTGTAAGTTGTTAAAGAGATCATCAGACTAGCGATACAGA

ATGCCTGTCACTCGGCAAGCTGTAAAGCGAAACCACAAATGAGTTGACTATGAACGTAGATTTT

TAAGTGGCGATGTGTTTGGACGCGGGTTCAACTCCCGCCGTTCCACCA

TABLE 25 tmDNA Sequence for *Thermoanaerobacterium saccharolyticum* (Bacillus/clostridium)

(SEQ ID NO: 33)
GGGGTAGTAGAGGTAAAAGTAGCGAGCCGAGGTTCCATCTGCTCGTAAAACGGTGGACTTAAAT

ATAAACGCAAACGATAATTTAGCTTACGCTGCTTAATTACAAGCAGCCGTTCAACCTTTGATTC

CCACATCAAAGGATTGGGCGTCGATTTAGTGGGGAACTGATTTATCAAAGCTTTGAGATAAATC

GGATTTTATGAAGCTACCAAAGCAGTTATCCTGTCACTGGGAGAACTGCAGAGGGAATGTCAAA

ACAGTGACTGCGCTCGGAGAAGCTTTTACTGTGACACCTTCGGACCGGGGTTCAACTCCCGCCA

GCTCCACCA

TABLE 26 tmDNA Sequence for *Mycoplasma fermentans*

(SEQ ID NO: 34)
GGGGCTGATTCTGGATTCGACATGCATTGGGTGATACTAATATCAGTAGTTTGGCAGACTATAA

TGCATCTAGGCTTTATAATCGCAGAAGATAAAAAAGCAGAAGAAGTTAATATTTCTTCACTTAT

TABLE 26-continued tmDNA Sequence for *Mycoplasma fermentans*

GATTGCACAAAAAATGCAATCACAATCAAACCTTGCTTTCGCTTAGTTAAAAGTGACAAGTGGT

TTTAAAGTTGACATTTTCCTATATATTTTAAAATCGGCTTTTAAGGAGAACAGGAGTCTGAAAG

GGTTCCAAAAATCTATATTGTTTGCATTTCGGTAGTATAGATTAATTAGAAATGATAAACTGTA

AAAAGTATTGGTATTGACTTGGTGTGTGGACTCGGGTTCAACTCCCGCCAGCTCCACCA

TABLE 27 tmDNA Sequence for *Mycoplasma hyorhinis*

(SEQ ID NO: 35)
GGGGCTGATTCTGGATTCGACATACATAAAAGGATATAAATTGCAGTGGTCTTGTAAACCATAA

GACAATTTCTTTACTAAGCGGAAAAGAAAACAAAAAAGAAGATTATTCATTATTAATGAATGCT

TCAACTCAATCAAATCTAGCTTTTGCATTTTAAAAAACTAGTAGACCAATTTGCTTCTCACGAA

TTGTAATCTTTATATTAGAGAATAGTTAAAAATCTGATCACTTTTTAATGAATTTATAGATCAC

AGGCTTTTTTAATCTTTTTGTTATTTTAGATAAAGAGTCTTCTTAAAAATAACTAAACTGTAGG

AATTTATATTTAATTATGCGTGGACCCGGGTTCAACTCCCGCCAGCTCCACCA

TABLE 28 tmDNA Sequence for *Mycoplasma pirum*

(SEQ ID NO: 36)
GGGGAGTCATGGTTTTGACATGAATGATGGACCCATAGAGGCAGTGGGGTATGCCCCTTATAGC

TCAAGGTTTAAATTAACCGACAAAACTGACGAAAACGTTGCCGTTGATACAAATTTATTAATCA

ACCAACAAGCTCAATTTAACTACGCATTTGCATAGTATAAAAAAATAAATTGTGCTACTCATTG

TAATTAGGTTACTAAATTACTTTGTTTTATATAGTCCTGTAACTAGTTCTAGTGATGTCTATAA

ACTAGAATGAGATTTATAGACTTATTTGTTGGCGGTTGTGCCATAGCCTAAATCAACAAAGACA

ATTTATTTATGGTACTAAACTGTAGATTCTATGATGAAATTATTTGTGGAAACGGGTTCGATTC

CCGCCATCTCCACCA

TABLE 29 tmDNA Sequence for *Mycoplasma salivarium*

(SEQ ID NO: 37)
GGGGCTGATTCTGGATTCGACAGGCATTCGATTCATTATGTTGCAGTGGTTTGCAAACCATAAG

GCACTAGGCTTTTTTAAACGCAAAAGACCAAAAAACAGAAGATCAAGCAGTTGATCTAGCATTT

ATGAATAATTCACAAATGCAATCAAATCTAGTTTTCGCTTAGTAAAATTAGTCAATTTATTATG

GTGCTCAACATAATAAATGGTAGTATGAGCTTAATATCATATGATTTTAGTTAATATGATAGGA

TTTGTAACTAAACTATGTTATAGAAATTTGTAAATTATATATATGACATAGGAAATTTAATTTA

CTAAACTGTAGATGCATAATGTTGAAGATGTGTGGACCGGGGTTCAACTCCCGCCAGCTCCACCA

TABLE 30 tmDNA Sequence for *Herpetosiphon aurantiacus*

(SEQ ID NO: 38)
GGGGGCGGAAAGGATTCGACGGGGAGGGCCAATCGTAAGTGGCAAGCCGAGACGCTGAGCCTCG

TTAAATCGGCAACGCCATTAACTGGCAAAAACACTTTCCGCGCTCCTGTAGCGCTTGCTGCCTA

TABLE 30-continued tmDNA Sequence for *Herpetosiphon aurantiacus*

ATTAAGGCAACACGTCTCTACTAGCCTCAGCCCGATGGGCTTGTAGCGGCGACACTTAGTCGGG

TCGCTCCCCTAGTTATGTCTGTGGGCTAGGGGCTAAGATTAACAGGCTGGTCGTGGCCCGCTTT

GTCTATCGGGTGGTGCACCGATAAGATTTAATCAATAGACTACGCTTGTAGATGCTTGCGGTTT

AACTTTTTGGACGCGGGTTCGATTCCCGCCGCCTCACCACCA

TABLE 31 tmDNA Sequence for *Thermomicrobium roseum*
(352 nts, temp. 70 degrees, green non sulfur)

GGGGCTGATTCTGGATTCGACAGGGCCGTAGGTGCGAGGATTGCAGGTCGAGGTCGCCCACGAA

CTCGTAAAAAGGGGCAGCCAAGTAACTGGCGAGCGCGAACTCGCTCTGGCTGCGTAATTCACGC

AGCCACGTCTGCCCGGACCCTTCCCTGGTGGGTTCGGAGCGGGCGCCGCAAGACCGGGGTGCCC

CTGGCCCAAGCGCCGGTGCGGGCCAGGTCAAGCGTGATCCGGCTCGGCTGACCGGGATCCTGTC

GGTGGGAGCCTGGCAGCGACAGTAGAACACCGACTAAGCCTGTAGCATATCCTCGGCTGAACGC

TCTGGACGCGGGTTCAACTCCCGCCAGCTCCACCA (SEQ ID NO:39)

TABLE 32 tmDNA Sequence for *Chlorobium limicola*

GGGGCTGATTCTGGATTCGACAGGATACGTGTGAGATGTCGTTGCACTCCGAGTTTCAGCATGG

ACGGACTCGTTAAACAAGTCTATGTACCATTAGATGCAGACGATTATTCGTATGCAATGGCTGC

CTGATTAGCACAAGTTAACTCAGACGCCATCGTCCTGCGGTGAATGCGCTTACTCTGAAGCCGC

CGGATGGCATAACCCGCGCTTGAGCCTACGGGTTCGCGCAAGTAAGCTCCGTACATTCATGCCC

GAGGGGCTGTGCGGGTAATTTCTCGGGATAAGGGGACGAACGCTGCTGGCGGTGTAATCGGCCC

ACGAAAACCCAATCACCAGAGATGAGTGTGGTGACTGCATCGAGCAGTGTTTTGGACGCGGGTT

CAACTCCCGCCAGCTCCACCA (SEQ ID NO:40)

TABLE 33 tmDNA Sequence for *Pirellula staleyi (planctomyces)*

GGGGCTGATTCTGGATTCGACCGGATAGCCTGAAGCGAATACGGCGTGCCGTGGTTGATCAGAT

GGCCACGTAAAAAGCTGATCACAAACTTAACTGCCGAGAGCAATCTCGCACTTGCTGCCTAACT

AAACGGTAGCTTCCGACTGAGGGCTTTAGCCGGAGAGGCCCAAAAGTTGGTCACCAAATCCGGA

CCGCCTCGTGCCATGATCGAAACGCACGAGGTCAAAAAAGTTTCGATCTAGTGCAGGGTGTAGC

CAGCAGCTAGGCGACAAACTGTGCAAAAATCAAATTTTCTGCTACGCACGTAGATGTGTTCGTG

AAAATGTCTCGGGACGGGGGTTCAACTCCCGCCACTCCACCA (SEQ ID NO:41)

TABLE 34 tmDNA Sequence for *Planctomyces limnophilus*

GGGGCTGATTCTGGATTCGACAACCTCTCAAGAGGAGCGTGGCCACTATGGGACTCGATTATGT

TGAATTCGTCATGGATCTTGAAGAGACCTTCGACATCAAACTGGATGACAAACATTTTTCAGCA

GTCAAAACACCACGCGATTTGGCAATCATTATTCGGGATCAATTAGCTGCTGAAGGCAGAATCT

TABLE 34-continued tmDNA Sequence for *Planctomyces limnophilus*

GGGATGAATCGAATGCTTTTCGCAAAATCTCGAATTTGAATTGGACGATGTTGCCCGAGTTCCG

GATGTGGACTCAAATCAAAAGCTCTCTACCAGTTTCTTTTCACCGACTGCGTCCCAGCACCCGT

CTCGTTCAACTCCCGCCANTCCACCA (SEQ ID NO:42)

TABLE 35 tmDNA Sequence for *Planctomyces maris*

GGGGCTGATTCTGGATTCGACTGGTTCACCGTATGTTAAGGTGGCGGTGCCGTGGTTGATCAGT

TGGCCACGTAAAAAGCTGATCACAATCTAATTGCAAACAAGCAATTTTCAATGGCTGCTTAATA

AAAGCAACCCCGGCTTAGGAATCTCTGTCTGAGGAGTCCGACAGCTGGTCACAAAATCAGACTG

GTATCAGATCAATGTCCGCTCCGTCTGATACGAGATTCGTGGTGGACTGGTTTCCAACAGGCTC

TGTTTATCGTGCCCGAAGAAACGAGACTCAAACGATAAAATATGCACCGTAGAGGCTTTAGCTG

AGGGTTCACAGGACGCGGGTTCAACTCCCGCCAGCTCCACCA (SEQ ID NO:43)

TABLE 36 tmDNA Sequence for *Alcaligenes eutrophus*

GGGGTTGATTCTGGATTCGACGTGGGTTACAAAGCAGTGGAGGGCATACCGAGGACCCGTCACC

TCGTTAATCAATGGGAATGCAATAACTGCTAACGACGAACGTTACGCACTGGCCGCTTAATTGC

GGCCGTCCTCGCACTGGCTCGCTGACGGGCTAGGGTCGCAAGACCACGCGAGGTCATTTACGTC

AGATAAGCTCCGGAAGGGTCACGAAGCCGGGGACGAAAACCTAGTGACTCGCCGTCGTAGAGCG

TGTTCGTCCGCGATGCGCCGGTTAAATCAAATGACAGAACTAAGTATGTAGAACTCTCTGTGGA

GGGCTTACGGACGCGGGTTCAACTCCCGCCAGCTCCACCA (SEQ ID NO:44)

TABLE 37 tmDNA Sequence for *Alcaligenes faecalis* (beta proteobacteria)

GGGGGCGGAAAGGATTCGACGGGGGTCAAGAAGCAGCACAGGGCGTGTCGAGCACCAGTACGCT

CGTAAATCCACTGGAAAACTATAAACGCCAACGACGAGCGTTTCGCTCTAGCCGCTTAAGGCTG

GGCCACTGCACTAATTTGTCTTTGGGTTAGGTAGGGCAACCTACAGCAGTGTTATTTACAAAGA

ATCGAATCGGTCTGCGCCACGAAGTCCGGTTCTAAAACTTAGTGGATCGCCAAGGAAAGGCCTG

TCAATTGGCATAGTCCAAGGTTAAAACTTAAAATTAATTGACTACACATGTAGAACTGTCTGTG

GACGGCTTGCGGACGGGGGTTCGATTCCCGCCGCCTCCACCA (SEQ ID NO:45)

TABLE 38 tmDNA Sequence for *Chromobacterium violaceum* (beta-purple)

GGGGCTGATTCTGGATTCGACGGGGGTTGCGAAGCAGATGAGGGCATACCGGGATTTCAGTCAC

CCCGTAAAACGCTGAATTTATATAGTCGCAAACGACGAAACTTACGCTCTGGCAGCCTAACGGC

CGGCCAGACACTACAACGGTTCGCAGATGGGCCGGGGGCGTCAAAACCCTGTAGTGTCACTCTA

CATCTGCTAGTGCTGTTCCGGGTTACTTGGTTCAGTGCGAAATAATAGGTAACTCGCCAAAGTC

TABLE 38-continued tmDNA Sequence for *Chromobacterium violaceum* (beta-purple)

CAGCCTGTCCGTCGGCGTGGCAGAGGTTAAATCCAAATGACACGACTAAGTATGTAGAACTCAC

TGTAGAGGACTTTCGGACGCGGGTTCAACTCCCGCCAGCTCCACCA (SEQ ID NO:46)

TABLE 39 tmDNA Sequence for *Hydrogenophaga palleroni* (beta-purple)

GGGGCTGATTCTGGATTCGACGTGGGTTCGGACGCGCAGCAGGGCATGTCGAGGTTCTGTCACC

TCGTAAATCAGCAGAAAAAAACCAACTGCAAACGACGAACGTTTCGCACTCGCCGCTTAAACAC

CGGTGAGCCTTGCAACAGCAGGCCGATGGGCTGGGCAAGGGGTCGCAAGACCTCCCGGCTGCA

AGGTAATTTACATCGGCTGGTTCTGCGTCGGGCACCTTGGCGCAGGATGAGATTCAAGGATGCT

GGCTTCCCGTTTAGCGTGCCACTGCGCGACTCGGGCGGCGAGACCCAAATCAGACGGCTACACA

TGTAGAACTGCTCGAAAAAGGCTTGCGGACGGGGGTTCAACTCCCGCCAGCTCCACCA (SEQ ID NO:47)

TABLE 40 tmDNA Sequence for *Methylobacillus glycogenes* (beta-purple)

GGGGGCGGAAAGGATTCGACGGGGGTTGCAAAGCAGCGCAGGGCATACCGAGGCCTAGTCACCT

CGTAAATAAACTAGAACAAGTATAGTCGCAAACGACGAAACTTACGCTCTAGCCGCTTAATCCC

GGCTGGACGCTGCACCGAAGGGCCTCTCGGTCGGGTGGGGTAACCCACAGCAGCGTCATTAAGA

GAGGATCGTGCGATATTGGGTTACTTAATATCGTATTAAATCCAAGGTAACTCGCCTGCTGTTT

GCTTGCTCGTTGGTGAGCATCAGGTTAAATCAAACAACACAGCTAAGTATGTAGAACTGTCTGT

GGAGGGCTTGCGGACGGGGGTTCGATTCCCGCCGCCTCACCACCA (SEQ ID NO:48)

TABLE 41 tmDNA Sequence for *Nitrosomonas cryotolerans* (beta-purple)

GGGGCTGATTCTGGATTCGACGTGGGTTGCAAAGCAGCGCAGGGCATACCGAGGACCAGAATAC

CTCGTAAATACATCTGGAAAAAAATAGTCGCAAACGACGAAAACTACGCTTTAGCCGCTTAATA

CGGCTAGCCTCTGCACCGATGGGCCTTAACGTCGGGTCTGGCAACAGACAGCAGAGTCATTAGC

AAGGATCGCGTTCTGTAGGGTCACTTTACAGAACGTTAAACAATAGGTGACTCGCCTGCCATCA

GCCCGCCAGCTGGCGGTTGTCAGGTTAAATTAAAGAGCATGGCTAAGTATGTAGAACTGTCTGT

AGAGGACTTGCGGACGCGGGTTCAACTCCCGCCAGTCCACCA (SEQ ID NO:49)

TABLE 42 tmDNA Sequence for *Pseudomonas testosteroni*

GGGGCTGATTCTGGATTCGACGTGGGTTCGGGACCGGTGCGGTGCATGTCGAGCTTGAGTGACG

CTCGTAAATCTCCATTCAAAAAACTAACTGCAAACGACGAACGTTTCGCACTCGCCGCTTAATC

CGGTGAGCCTTGCAACAGCACGCTAGTGGGCTGGGCAAGGGGTAGCAATACCTCCCGGCTGCA

AGGGAATTTTCATTAGCTGGCTGGATACCGGGCTTCTTGGTATTTGGCGAGATTTTAGGAAGCT

GGCTACCCAAGCAGCGTGTGCCTGCGGGGTTTGGGTGGCGAGATTTAAAACAGAGCACTAAACA

TABLE 42-continued tmDNA Sequence for *Pseudomonas testosteroni*

TGTAGATCTGTCCGGCGAAGGCTTACGGACGCGGGTTCAACTCCCGCCAGCTCCACCA (SEQ ID NO:50)

TABLE 43 tmDNA Sequence for *Ralstonia pickettii* (Burkholderia)

GGGGGCGGAAAGGATTCGACGGGGGTTGCGAAGCAGCGGAGGGCATACCGAGGACCCGTCACCT

CGTTAATCAATGGGAATGCAATAACTGCTAACGACGAACGTTACGCACTGGCAGCCTAAGGGCC

GCCGTCCTCGCACTGGCTCGCTGACGGGCTAGGGTCGCAAGACCAGCGAGGTCATTTACGTCAG

ATAAGCTTTAGGTGAGTCACGGGCCTAGAGACGAAAACTTAGTGAATCGCCGTCGTAGAGCGTG

TTCGTCCGCGATGCGGCGGTTAAATCAAATGACAGAACTAAGTATGTAGAACTCTCTGTGGAGG

GCTTGCGGACGCGGGTTCGATTCCCGCCGCCTCACCACCA (SEQ ID NO:51)

TABLE 44 tmDNA Sequence for *Variovax paradoxus* (pseudomonas sp.)

GGGGCTGATTCTGGATTCGACGTGGGTTCGGAGTCGCAGCGGGGCATGTCGAGCTGAATGCGCT

CGTAAAACAGATTCAAACAAACTAACTGCAAACGACGAACGTTTCGCACTCGCTGCTTAATTGC

CAGTGAGCCTTGCAACAGTTGGCCGATGGGCTGGGCAAGGGGGTCTGGAGCAATCCTGACCTCC

CGGCTGCAAGGATAACTACATGGGCTGGCTCCGATCCGGGTACCTTGGGTCGGGGCGAGAAAAT

AGGGTACTGGCGTCCGGTTTAGCGTGTGACTGCGCGACTCCGGAAGCGAGACTCAAAACAGATC

ACTAAACATGTAGAACTGCGCGATGAAGGCTTGCGGACGGGGGTTCAACTCCCGCCAGCTCCACCA (SEQ ID NO:52)

TABLE 45 tmDNA Sequence for *Bdellovibrio bacteriovorus* (delta proteobacterie)

GGGGGCGGAAAGGATTCGACGGGGGTGCTGAAGCATAAGGAGCATACCGGGGCGGATGAGGACC

TCGTTAAAAACGTCCACTTTGTAATTGGCAACGATTACGCACTTGCAGCTTAATTAAGCAGCAC

GATCAACCTTGTGGTGGTTCCGCACTTGGATTGATCGTCATTTAGGGACCTCGGCGTGTTGGGT

TTTCTCCAGCAGACATGCTTAAATTTACTGGGGGAGAGGTCTTAGGGATTTTGTCTGTGGAAGC

CCGAGGACCAATCTAAAACACTGACTAAGTATGTAGCGCCTTATCGTGGATCATTTGCGGACGG

GGGTTCGATTCCCGCCGCCTCCACCA (SEQ ID NO:53)

TABLE 46 tmDNA Sequence for *Myxococcus xanthus* (delta proteobacterie)

(SEQ ID NO:54)
GGGGGCGGAAAGGATTCGACGGGGGCATTGAAGTTCGAGACGCGTGCCGAGCTTGTCAGGTAGC
TCGTAAATTCAACCCGGCAAAGACACAAAAGCCAACGACAACGTTGAGCTCGCGCTGGCTGCCT
AAAAACAGCCCATAGTGCGCGGTCCCCCCGCCCTCGGCCTGTGGGGTTGGGACAGACCGTCATA
ATGCAGGCTGGCTGCCGAGGGTGCCTGGACCCGAGGTGGCGAGATCTTCCCAGGACCGGCTCTG
AGTATCCCGTCCGTGGGAGCCTCAGGGACGTAGCAAATCGCGGACTACGCACGTAGGGTCGAAG
AGCGGACGGCTTTCGGACGCGGGTTCGATTCCCGCCGCCTCCACCA

TABLE 47 tmDNA Sequence for *Sulfurospirillum Deleyianum*

(SEQ ID NO:55)
GGGGCTGATTCTGGATTCGACAGGAGTAGTTTTAGCTTATGGCTGCATGTCGGGAGTGAGGGTC
TTCCGTTACACAACCTTCAAACAATAACTGCTAACAACAGTAACTATCGTCCTGCTTACGCGCT
AGCTGCGTAAGTTTAACAAATAATGGACTGCTCTCCCCTTTGATGCTATCTTAGGAGGTCTTGG
AGAGTATCATAGATTTGATAGCTATATTACATGAACGCCTTTACATGTAATGAAGTTAAAGGCT
CGTTTTGCGTAGTTTTCTGATTGTTGTACGAAGCAAAATTAAACACTATCAACAATATCTAAGC
ATGTAGACGTCATAGGTGGCTATTTTTGGACTGCGGGTTCAACTCCCGCCAGCTCCACCA

TABLE 48 tmDNA Sequence for *Chromatium vinosum*

(SEQ ID NO:56)
GGGGCTGATTCTGGATTCGACGTGGGTCGCGAAACCTAAGGTGCATGCCGAGGTGCGGTTGACC
TCGTAAAACCCTCCGCAAACTTATAGTTGCCAACGACGACAACTACGCTCTCGCTGCTTAATCC
CAGCGGGCCTCTGACCGTCACTTGCCTGTGGGCGGCGGATTCCAGGGGTAACCTCACACAGGAT
CGTGGTGACGGGAGTCCGGACCTGATCCACTAAAACCTAACGGAATCGCCGACTGATCGCCCTG
CCCTTCGGGCGGCAGAAGGCTAAAAACAATAGAGTGGGCTAAGCATGTAGGACCGAGGGCAGAG
GGCTTGCGGACGCGGGTTCAACTCCCGCCAGCTCCACCA

TABLE 49 tmDNA Sequence for *Pseudomonas fluorescens*
(gamma proteobacteria)

(SEQ ID NO:57)
GGGGCTGATTCTGGATTCGACGCCGGTTGCGAACCTTTAGGTGCATGCCGAGTTGGTAACAGAA
CTCGTAAATCCACTGTTGCAACTTTCTATAGTTGCCAATGACGAAACCTACGGGGAATACGCTC
TCGCTGCGTAAGCAGCCTTAGCCCTTCCCTCCTGGTACCTTCGGGTCCAGCAATCATCAGGGGA
TGTCTGTAAACCCAAAGTGATTGTCATATAGAACAGAATCGCCGTGCAGTACGTTGTGGACGAA
GCGGCTAAAACTTACACAACTCGCCCAAAGCACCCTGCCCGTCGGGTCGCTGAGGGTTAACTTA
ATAGACACGGCTACGCATGTAGTACCGACAGCAGAGTACTGGCGGACGCGGGTTCAACTCCCGC
CAGCTCCACCA

TABLE 50 tmDNA Sequence for *Borrelia afzeli*

(SEQ ID NO:58)
GGGGCTGATTCTGGATTCGACTGAAAATGCTAATATTGTAAGTTGCAAGCAGAGGGAATCTCTT
AAAACTTCTAAAATAAATGCAAAAAATAATAACTTTACAAGTTCAAACCTTGTAATGGCTGCTT
AAGTTAGCAGAGAGTTTTGTTGAATTTGGCTTTGAGATTCACTTATACTCTTTTAGACATCGAA
GCTTGCTTAAAAATGTTTTCAAGTTGATTTTTAGGGACTTTTATACTTGAGAGCAATTTGGCGG
TTTGCTAGTATTTCCAAACCATATTGCTTAGTAAAATACTAGATAAGCTTGTAGAAGCTTATAG
TATTGTTTTAGGACGCGGGTTCAACTCCCGCCAGTCCACCA

TABLE 51 tmDNA Sequence for *Borrelia crociduarae*

(SEQ ID NO:59)
GGGGCTGATTCTGGATTCGACTAAGAACTTTAGTAGCATAAATGGCAAGCAGAGTGAATCTCTT
AAAACTTCTTTAATAAATGCAAAAAATAATAACTTTACAAGTTCAGATCTTGTAATGGCTGCTT
AATTTAGCAGAGAGTTTTGTTGGATTTTGCTTTGAGGTTCAACTTATACTCTTTAAGACATCAA
AGTATGCCTAAAAATGTTTCAAGTTGATTTTTAGGGACCTTTAAACTTGAGAGTAATTTGGTGG
TTTGCTTGTTTTCCAAGCCTTATTGCTTTTTCTAAAAATTAGCTAAGCTTGTAGATATTTATGA
TATTATTTTTAGGACGCGGGTTCAACTCCCGCCAGTTCCACCA

TABLE 52 tmDNA Sequence for *Borrelia hermsii*

(SEQ ID NO:60)
GGGGCTGATTCTGGATTCGACTAAAAACTTTAGTAGCATAAATTGCAAGCAGAGGGAATCTCTT
AAAACTTCTTTAATAAATGCAAGAAATAATAACTTTACAAGTTCAAATCTTGTAATGGCTGCTT

TABLE 52-continued tmDNA Sequence for *Borrelia hermsii*

AAATTAGCAGAGAGTTCTGCTGGATTTTGCTTTGAGGTTCAGCTTATACTCTTTTAAGACATCA
AAGCTTGCTTAAAAATATTTCAAGTTGATTTTTAGGGACTTTTAAATTTGAGAGTAATTTGGCG
GTTTGCTAGTTTTTCCAAACCTTATTACTTAAAGAAAACACTAGCTAAGCTTGTAGATATTTAT
GATATTATTTTTAGGACGCGGGTTCAACTCCCGCCAGCTCCACCA

TABLE 53 tmDNA Sequence for *Borrelia garinii*

(SEQ ID NO:61)
GGGGCTGATTCTGGATTCGACTGAAAATGCGAATATTGTAAGTTGCAGGCAGAGGGAATCTCTT
AAAACTTCTAAAATAAATGCAAAAAATAATAACTTTACAAGCTCAAACCTTGTAATGGCTGCTT
AAGTTAGCAGGGAGTTTCGTTGAATTTGGCTTTGAGGTTCACTTATACTCTTTTCGATATCGAA
GCTTGCTTAAAAATGTTTTCAAGTTAATTTTTAGGGACTTTTGTACTTGAGAGCAATTTGGCGG
TTTGCTAGTATTTCCAAACCATATTGCTTAAGTAAAATGCTAGATAAGCTTGTAGAAGCTTATA
ATATTGTTTTTAGGACGCGGGTTCAACTCCCGCCAGTCCACCA

TABLE 54 tmDNA Sequence for *Thermodesulfobacterium commune* (70 degrees)

(SEQ ID NO:62)
GGGGGCGGAAAGGATTCGACGGGGATAGGTAGGATTAAACAGCAGGCCGTGGTCGCACCCAACC
ACGTTAAATAGGGTGCAAAAACACAACTGCCAACGAATACGCCTACGCTTTGGCAGCCTAAGCG
TGCTGCCACGCACCTTTAGACCTTGCCTGTGGGTCTAAAGGTGTGTGACCTAACAGGCTTTGGG
AGGCTTAATCGGTGGGGTTAAGCCTCCCGAGATTACATCCCACCTGGTAGGGTTGCTTGGTGCC
TGTGACAAGCACCCTACGAGATTTTCCCACAGGCTAAGCCTGTAGCGGTTTAATCTGAACTATC
TCCGGACGCGGGTTCGATTCCCGCCGCCTCCCCACCA

TABLE 55 tmDNA Sequence for *Thermotoga neapolitana* (Thermotogales)

(SEQ ID NO:63)
GGGGGCGGAAAGGATTCGACGGGGATGGAGTCCCCTGGGAAGCGAGCCGAGGTCCCCACCTCCT
CGTAAAAAAGGTGGGAACACGAATAAGTGCCAACGAACCTGTTGCTGTTGCCGCCTAATAGATA
GGCGGCCGTCCTCTCCGGAGTTGGCTGGGCTCCGGAAGAGGGCGTGAGGGATCCAGCCTACCGA
TCTGGGCTCCGCCTTCCGGCCCGGATCGGGAAGGTTCAGGAAGGCTGTGGGAAGCGACACCCTG
CCCGTGGGGGGTCCTTCCCGAGACACGAAACACGGGCTGCGCTCGGAGAAGCCCAGGGGCCTCC
ATCTTCNGACGCGGGTTCGATTCCCGCCACCTCCACCA

TABLE 56 tmDNA Sequence for *Deinococcus proteolyticus*

(SEQ ID NO:64)
GGGGGCGGAAAGGATTCGACGGGGGAACGGAAAGCGCTGCTGCGTGCCGAGGAGCCGTTGGCCT
CGTAAACAAACGGCAAAGCCATTAACTGGCGAAAATAACTACGCTCTCGCTGCTTAAGTGAGAC
AGTGACCACGTAGCCCCGCCTTTGGCGACGTGTGAACTGAGACAAAAGAAGGCTAGCTTAGGTG
AGGTTCCATAGCCAAAAGTGAAACCAAATGGAAATAAGGCGGACGGCAGCCTGTTTGCTGGCAG
CCCAGGCCCGACAATTTAAGAGCAGACTACGCACGTAGATGCACGCTGGATGGACCTTTGGACG
CGGGTTCGATTCCCGCCAGCTCCACCA

TABLE 57 tmDNA Sequence for *Prosthecobacter fusiformis* (verrucomicrobia)

(SEQ ID NO:65)
GGGGCTGATTCTGGATTCGACGGGGAGTACAAGGATCAAAAGCTGCAAGCCGAGGTGCCGTTAC
CTCGTAAAACAACGGCAAAAAAGAAGTGCCAACACAAATTTAGCATTAGCTGCTTAATTTAGCA
GCTACGCTCTTCTAACCCGGGCTGGCAGGGTTAGAAGGGTGTCATAATGAGCCAGCTGCCCCTT
CCGACTCCCCTAAGGAAGGGAAAGATGTAGGGGATAGGTGCTTACAGAATCCTGCGGGAGGGAG
TCTGTAAGTGCCGAAAAGTTAAAACTCCCGCTAAGCTTGTAGAGGCTTTTGATTCTTGCTCTCT
GGACGCGGGTTCAACTCCCGCCAGCTCCACCA

TABLE 58 tmDNA Sequence for *Verrucomicrobium spinosum* (verrucomicrobium)

(SEQ ID NO:66)
GGGNNNNATTTGGAATTCGCCGAATGCTAGAAGTGGAGGCTGCATGCCGCGGATGATTCGTTGG
CCGCTTTACCAATTCGGATCAAACAACTAAATGCGGACTCTAACGAGCTTGCCCTCGCCGCTTA
ATTGACGGTGACGTTCCTCCAGTGAAGTCTGTGAATTGGAGGAGCGACTACTTACAGGCTGCC
AAAAGAGCGGGCGACCGGCCCCAAGGCGAGATCTACAGGCCGCTGGATGGACGGCATCCTGGCA
GTAGGAGGCTGGACATCGAGATCAAATNATTGCCTGAGCATGGAGACGCTTTCATAAAGGNGTT
CGGACAGGG

Example 4

Alignment of tmRNA Sequences

The newly discovered tmRNA sequences and several known tmRNA sequences were aligned to identify target sites for drug development. The alignments of the sequences are shown in FIGS. 3A–11B. The nucleotides in the tmRNA sequences of these figures exist in several motifs (Felden et al., 1999). These motifs include nucleotides considered to be in RNA helices (Watson-Crick base-pairs GC or AU, or GU Wobble base-pairs). Nucleotides that are in in single stranded RNA domains, hence not base-paired. Some nucleotides in the single stranded domains are universally conserved nucleotides. Other nucleotides are the exceptions to a quasi-sequence conservation in the sequences alignment. Several nucleotides exist in well established non-canonical structural motifs in RNA structures; for example AG-GA pairs, AA pairs, etc. Some nucleotides are universally conserved Wobble GU base-pairs.

All the gene sequences have been decomposed in several structural domains that have been indicated with names at the top of each block of sequences. These domains are respectively from the 5'-end to the 3'-end of the sequences: H1, H5, H2, PK1, H4, PK2, PK3, PK4, H5 and H6. The bars delineate all the structural domains. H means helices and PK means pseudoknot. A pseudoknot is made of the pairing of parts of an RNA-loop with an upstream sequence. Consequently, two helices are made (shown in Felden et al., 1999) for all the 4 pseudoknots PK1 to PK4 for each sequence. Moreover, the tRNA-like domain as well as the coding sequence, namely the two functional units of the molecule, have also been indicated for each sequence.

The sequences, especially as identified by the sequence alignment, represent targets for the development of drugs which may be broadly applicable to many kinds of bacteria, or may be broadly applicable only to a particular genera of phylum of bacteria, or may be specifically applicable to a single species of bacteria.

Common Structural Features for Drug Targeting:

For all the novel tmRNA sequences, as well as with the ones that are already known, there are systematically several structural domains that are always found. These domains can be used as targets for the development of drugs which may be genera specific or which may be eubacteria specific. These domains are either RNA helices which can be sometimes interrupted by bulges or pseudoknots. The RNA helices which are always present are H1, H2, H5 and H6. Helices H1 and H6 are found in all canonical transfer RNAs. Thus, H1 and H6 are not good targets for drug development because drugs that would target them will also interfere with the biology of the individual that has a given disease. Consequently, very good candidates for development of drugs for targeting as many bacteria as possible are helices H2 and H5. Moreover, helices H2 and H5 are critical for the folding of all these tmRNA since both of them connect the two ends of the molecule together. Disruption of either H2 or H5 with a specific drug would lead to inactive tmRNA molecules in vivo. Similarly, pseudoknots PK1, PK2 and PK3 are always found in the bacterial tmRNAs. The PK1 structural domain is strictly conserved in the tmRNAs and is located upstream of the coding sequence. Since these pseudoknots are not found in all canonial transfer RNAs, they can also be targeted with specific drugs. Disruption of either PK1 or PK2 or PK3 with a specific drug would lead to inactive tmRNA molecules in vivo.

Specific Structural Features in Each Phylum that Could be Targeted by Drugs:

In addition to developing drugs which broadly target many bacteria, drugs are developed which are more genera specific. For trying to target specifically a given bacteria or a complete phylum, the coding sequence (shown in all the alignments) is a very good candidate. Indeed, this region of the RNA is very accessible for DNA antisense binding, which has been shown for *Escherichia coli*, and thus, is also available for interaction with other drugs. Moreover, this is a critical functional domain of the molecule in its quality-control mechanism in cells. In addition, this coding sequence would be the ideal target to use for designing specific PCR-based diagnostic assays for infection diseases.

Interestingly, some structural domains are present only in a given bacterial phyla and could be targeted for discovering a drug that will be specific of a phylum, but not of the others. For example:

(1) in the cyanobacteria, the fourth pseudoknot PK4 is made of two smaller pseudoknots called PK4a and PK4b;

(2) in the mycoplasma, helix H2 is made of only 4 base-pairs instead of 5 in the other species;

(3) for two sequences of chlorobium as well as *Bacteroides thetaiotaomicron* and ppm gingiv., there is an additional domain just downstream of the coding sequence that is unique to them;

(4) there is always a stem-loop in the coding sequence of the actinobacteria (Felden et al., 1999); and (5) all the beta proteobacteria possess a sequence insertion in pseudoknot PK2 (shown in the alignment).

The novel sequences described herein, when aligned, show that specific structural domains within tmRNA are strictly conserved, as for example pseudoknot PK1 is located upstream (at the 5'-side) of the coding sequence. As previously disclosed, this pseudoknot is a target for future anti-bacterial drugs. Moreover, recent data have shown that this PK1 pseudoknot, among all the four pseudoknots within tmRNA gene sequences (sometimes there's only 2 or 3 detectable pseudoknots, depending upon the sequences), is the only one that its correct folding is essential for the biological activity of tmRNA (Nameki et al., 1999; Nameki et al., 2000).

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Andersson, S. G. et al. (1998). *Nature* 396:133–140.
Ando, H. et al. (1996). *Genes & Genet. Syst.* 71:47–50.
Breithaupt, H. (1999). *Nature Biotechnol.* 17:1165–1169.
Felden, B. et al. (1996). *Biochimie* 78:979–983.
Felden, B. et al. (1997). *RNA* 3:89–103.
Felden, B. et al. (1998). *EMBO J.* 17:3188–3196.
Felden et al. (1999). *Biochim. Biophys. Acta* 1446:145–148.
Gray, M. W. and Spencer, D. F. (1996). In *Evolution of Microbial Life*, Cambridge University Press, pp. 109–126.
Hickerson, R. P. et al. (1998). *J. Mol. Biol.* 279:577–587.
Himeno, H. et al. (1997). *J. Mol. Biol.* 268:803–808.
Huang, C. et al. (2000). *EMBO J.* 19:1098–1107.
Julio, S. M et al. (2000). *J. Bacteriol.* 182:1558–1563.
Keiler, K. C. et al. (1996). *Science* 271:990–993.
Komine, Y. et al. (1994). *Proc. Natl. Acad. Sci. USA* 20:9223–9227.
Mateeva, O. et al. (1997). *Nucleic Acids Res.* 25:5010–5016.
Muto, A. et al. (1998). *Trends Biochem. Sci.* 1:25–29.
Nameki, N. et al. (1999). *J. Mol. Biol.* 286:733–744.
Nakemi, N. et al. (2000). *FEBS Lett.* 470:345–349.
*Remington's Pharmaceutical Sciences*, 18th Ed., Mack Publishing Co., Easton, Pa., 1990.
Tu, G. F. et al. (1995). *J. Biol. Chem.* 270:9322–9326.
Ushida, C. et al. (1994). *Nucleic Acids Res.* 16:3392–3396.
Williams, K. P. (1999). *Nucleic Acids Res.* 27:165–166.
Williams, K. P. and Bartel, D. P. (1996). *RNA* 2:1306–1310.
Wower, J. and Zwieb, C. (1999). *Nucleic Acids Res.* 27:167.
Yang, D. et al. (1985). *Proc. Natl. Acad. Sci. USA* 82:4443–4447.

The invention claimed is:

1. An isolated nucleic acid sequence selected from the group consisting of the tmDNA sequence for *Staphylococcus epidermidis* set forth in SEQ ID NO: 31, the complement of said tmDNA sequence, and the tmRNA sequence set forth in SEQ ID NO: 85.

2. A method for diagnosing the presence of *Staphylococcus epidermidis* comprising determining the presence of a bacterial nucleic acid sequence selected from the group consisting of the tmDNA sequence for *Staphylococcus epidermidis* set forth in SEQ ID NO: 31, the complement of said tmDNA sequence, and the tmRNA sequence set forth in SEQ ID NO: 85.

3. The method of claim 2 wherein the determination is made by performing an amplification-based assay.

4. The isolated nucleic acid sequence of claim 1, wherein the nucleic acid sequence is the tmDNA sequence for *Staphylococcus epidermidis* set forth in SEQ ID NO: 31.

5. The method of claim 2, wherein the bacterial nucleic acid sequence is the tmDNA sequence for *Staphylococcus epidermidis* set forth in SEQ ID NO: 31.

6. The method of claim 3, wherein the bacterial nucleic acid sequence is the tmDNA sequence for *Staphylococcus epidermidis* set forth in SEQ ID NO: 31.

* * * * *